(12) United States Patent
Noureldin et al.

(10) Patent No.: US 10,502,495 B2
(45) Date of Patent: Dec. 10, 2019

(54) SYSTEMS FOR RECOVERY AND RE-USE OF WASTE ENERGY IN CRUDE OIL REFINING FACILITY AND AROMATICS COMPLEX

(71) Applicant: Saudi Arabian Oil Company, Dhahran (SA)

(72) Inventors: Mahmoud Bahy Mahmoud Noureldin, Dhahran (SA); Hani Mohammed Al Saed, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/833,730

(22) Filed: Dec. 6, 2017

(65) Prior Publication Data
US 2018/0094863 A1     Apr. 5, 2018

Related U.S. Application Data

(63) Continuation of application No. 15/242,043, filed on Aug. 19, 2016, now Pat. No. 9,845,996.

(Continued)

(51) Int. Cl.
    *F28D 7/00*         (2006.01)
    *B01D 53/48*      (2006.01)
                (Continued)

(52) U.S. Cl.
    CPC ........... *F28D 7/0083* (2013.01); *B01D 3/007* (2013.01); *B01D 3/32* (2013.01); *B01D 51/10* (2013.01); *B01D 53/047* (2013.01); *B01D 53/1462* (2013.01); *B01D 53/185* (2013.01); *B01D 53/343* (2013.01); *B01D 53/48* (2013.01);

(Continued)

(58) Field of Classification Search
CPC ................................ F28D 7/00; F28D 7/0083
See application file for complete search history.

(56) References Cited

U.S. PATENT DOCUMENTS

| | | |
|---|---|---|
| 3,995,428 A | 12/1976 | Roberts |
| 4,109,469 A | 8/1978 | Carson |

(Continued)

FOREIGN PATENT DOCUMENTS

| | | |
|---|---|---|
| CN | 1844325 | 10/2006 |
| CN | 101424453 | 5/2009 |

(Continued)

OTHER PUBLICATIONS

Communication Pursuant to Article 94(3) EPC issued in European Application No. 16758058.8 dated Dec. 11, 2018, 4 pages.

(Continued)

*Primary Examiner* — Brian A McCaig
(74) *Attorney, Agent, or Firm* — Fish & Richardson P.C.

(57) ABSTRACT

Configurations and related processing schemes of inter-plants and hybrid, intra- and inter-plants' direct or indirect heating systems synthesized for grassroots medium grade crude oil semi-conversion refineries to increase energy efficiency from specific portions of low grade waste heat sources are described. Configurations and related processing schemes of inter-plants and hybrid, intra- and inter-plants' direct or indirect heating systems synthesized for integrated medium grade crude oil semi-conversion refineries and aromatics complex for increasing energy efficiency from specific portions of low grade waste sources are also described.

37 Claims, 46 Drawing Sheets

Related U.S. Application Data

(60) Provisional application No. 62/209,217, filed on Aug. 24, 2015, provisional application No. 62/209,147, filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| *C10G 47/00* | (2006.01) | |
| *C10G 65/00* | (2006.01) | |
| *C10G 69/00* | (2006.01) | |
| *C10G 45/02* | (2006.01) | |
| *C10G 35/04* | (2006.01) | |
| *C10L 3/10* | (2006.01) | |
| *C07C 7/08* | (2006.01) | |
| *C10G 65/12* | (2006.01) | |
| *C10G 33/06* | (2006.01) | |
| *B01D 3/00* | (2006.01) | |
| *B01D 3/32* | (2006.01) | |
| *B01D 51/10* | (2006.01) | |
| *B01D 53/047* | (2006.01) | |
| *B01D 53/14* | (2006.01) | |
| *B01D 53/18* | (2006.01) | |
| *B01D 53/34* | (2006.01) | |
| *B01D 53/86* | (2006.01) | |
| *B01D 53/96* | (2006.01) | |
| *C02F 1/58* | (2006.01) | |
| *C10G 45/44* | (2006.01) | |
| *F28F 9/26* | (2006.01) | |
| *F01D 17/14* | (2006.01) | |
| *F01K 3/18* | (2006.01) | |
| *F01K 13/02* | (2006.01) | |
| *H02K 7/18* | (2006.01) | |
| *F01K 25/06* | (2006.01) | |
| *F01K 25/08* | (2006.01) | |
| *F01K 27/02* | (2006.01) | |
| *F01K 13/00* | (2006.01) | |
| *F01K 23/06* | (2006.01) | |
| *C01B 3/24* | (2006.01) | |
| *C10G 45/00* | (2006.01) | |
| *C10K 3/04* | (2006.01) | |
| *F01K 27/00* | (2006.01) | |
| *C01B 3/34* | (2006.01) | |
| *C02F 101/10* | (2006.01) | |
| *C02F 101/16* | (2006.01) | |
| *C02F 103/18* | (2006.01) | |
| *C02F 103/36* | (2006.01) | |

(52) U.S. Cl.
CPC ......... *B01D 53/8603* (2013.01); *B01D 53/96* (2013.01); *C01B 3/24* (2013.01); *C01B 3/34* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0227* (2013.01); *C01B 2203/0233* (2013.01); *C01B 2203/0283* (2013.01); *C01B 2203/043* (2013.01); *C01B 2203/127* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01); *Y02P 20/129* (2015.11); *Y02P 30/10* (2015.11)

(56) References Cited

U.S. PATENT DOCUMENTS

| | | |
|---|---|---|
| 4,291,232 A | 9/1981 | Cardone |
| 4,471,619 A | 9/1984 | Nolley, Jr. |
| 4,512,155 A | 4/1985 | Sheinbaum |
| 4,792,390 A | 12/1988 | Staggs |
| 4,962,238 A | 10/1990 | Wolfe |
| 5,007,240 A | 4/1991 | Ishida |
| 5,164,070 A | 11/1992 | Munro |
| 5,240,476 A | 8/1993 | Hegarty |
| 5,497,624 A | 3/1996 | Amir |
| 6,733,636 B1 | 5/2004 | Heins |
| 8,046,999 B2 | 11/2011 | Doty |
| 9,328,634 B2 | 5/2016 | Ikegami |
| 9,562,201 B2 | 2/2017 | Noureldin |
| 9,851,153 B2 | 12/2017 | Noureldin |
| 2002/0023538 A1 | 2/2002 | Agarwal |
| 2003/0092952 A1 | 5/2003 | Netzer |
| 2003/0132138 A1 | 7/2003 | Mehra |
| 2004/0186332 A1 | 9/2004 | Kong |
| 2006/0010872 A1 | 1/2006 | Singh |
| 2008/0128134 A1 | 6/2008 | Mudunuri |
| 2008/0174115 A1 | 7/2008 | Lambirth |
| 2008/0257413 A1 | 10/2008 | Noureldin et al. |
| 2008/0289588 A1 | 11/2008 | Wees et al. |
| 2008/0314726 A1 | 12/2008 | Choros |
| 2009/0000299 A1 | 1/2009 | Ast |
| 2009/0000906 A1 | 1/2009 | Petri |
| 2009/0071652 A1 | 3/2009 | Vinegar |
| 2009/0225929 A1 | 9/2009 | Genta et al. |
| 2009/0287029 A1 | 11/2009 | Anumakonda et al. |
| 2009/0301087 A1 | 12/2009 | Borissov et al. |
| 2010/0146974 A1 | 6/2010 | Ast |
| 2010/0242476 A1 | 9/2010 | Ast |
| 2010/0263380 A1 | 10/2010 | Biederman |
| 2010/0319346 A1 | 12/2010 | Ast |
| 2010/0326076 A1 | 12/2010 | Ast |
| 2011/0016863 A1 | 1/2011 | Ernst |
| 2011/0072819 A1 | 3/2011 | Silva |
| 2011/0072820 A1 | 3/2011 | Finkenrath |
| 2011/0083437 A1 | 4/2011 | Ast |
| 2011/0158858 A1 | 6/2011 | Alves |
| 2012/0031096 A1 | 2/2012 | Acikgoz et al. |
| 2012/0047889 A1 | 3/2012 | Acikgoz et al. |
| 2012/0048718 A1 | 3/2012 | Werba |
| 2012/0085096 A1 | 4/2012 | Penton et al. |
| 2012/0131921 A1 | 5/2012 | Held |
| 2012/0279728 A1 | 11/2012 | Northrop |
| 2012/0279900 A1 | 11/2012 | Noureldin et al. |
| 2012/0285169 A1 | 11/2012 | Freund |
| 2012/0298552 A1 | 11/2012 | Koseoglu |
| 2013/0104546 A1 | 5/2013 | Goswami |
| 2013/0145763 A1 | 6/2013 | Mirmobin et al. |
| 2013/0165534 A1 | 6/2013 | McComish |
| 2013/0213040 A1 | 8/2013 | Goswami |
| 2013/0231909 A1 | 9/2013 | Noureldin |
| 2013/0238154 A1 | 9/2013 | Noureldin |
| 2013/0334060 A1 | 12/2013 | Koseoglu et al. |
| 2014/0090405 A1 | 4/2014 | Held et al. |
| 2014/0142364 A1 | 5/2014 | Io |

(56) References Cited

U.S. PATENT DOCUMENTS

| | | | |
|---|---|---|---|
| 2014/0260311 | A1 | 9/2014 | Berlowitz |
| 2015/0377079 | A1 | 12/2015 | Noureldin |
| 2016/0045841 | A1 | 2/2016 | Kaplan |
| 2017/0058206 | A1 | 3/2017 | Noureldin et al. |

FOREIGN PATENT DOCUMENTS

| | | |
|---|---|---|
| CN | 104560082 | 4/2015 |
| DE | 3731978 | 3/1988 |
| EP | 292391 | 11/1988 |
| EP | 949318 | 10/1999 |
| EP | 2516326 | 10/2012 |
| FR | 2990990 | 11/2013 |
| SU | 295317 | 10/1977 |
| WO | 97/21786 | 6/1997 |
| WO | 2004102082 | 11/2004 |
| WO | 2011090553 | 7/2011 |
| WO | 2012048132 | 4/2012 |
| WO | 2013055864 | 4/2013 |
| WO | 2014205163 | 12/2014 |

OTHER PUBLICATIONS

Feng Xu, D. Yogi Goswami and Sunil S. Bhagwat, "A combined power/cooling cycle," Energy, 25 (2000), 233-246.
D. Zheng, B. Chen, Y. Qi and H. Jin, "Thermodynamic analysis of a novel absorption power/cooling combined cycle," Applied Energy, 83 (2006), 311-323.
Meng Liu, and Na Zhang, "Proposal and analysis of a novel ammonia-water cycle for power and refrigeration cogeneration," Energy, 32 (2007), 961-970.
J.Wang, Y. Dai and L. Gao, "Parametric analysis and optimization for a combined power and refrigeration cycle," Applied Energy, 85 (2008), 1071-1085.
R.V. Padilla, G. Demirkaya, D. Yogi Goswami, E. Stefanakos, and M. A. Rahman, "Analysis of power and cooling cogeneration using ammonia-water mixture," Energy, 35 (2010), 4649-4657.
D. Ayou, J. C. Bruno, R. Saravanan and A. Coronas, "An Overview of Combined Absorption Power and Cooling Cycles," Renewable sustainable energy reviews, 21 (2013), 728-748.
J. Hua, Y. Chen, Y. Wang and A.P. Roskilly, "Thermodynamic analysis of ammonia-water power/chilling cogeneration cycle with low grade waste heat," Applied thermal engineering, 64 (2014), 483-490.
Hasan et al., "First and Second Law Analysis of a New Power and Refrigeration Thermodynamic Cycle using a Solar Heat Source," Pergamon, Solar Energy, vol. 73, No. 5, Nov. 1, 2002, pp. 385-393.
Stecco, "Kalina Cycles: Some Possible Applications and Comments," Proceedings of the American Power Conference, XP000609703, Jan. 1, 1993, vol. 1, pp. 196-201.
Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-228.
Sadrameli et al., "Optimum Operating Conditions for a Combined Power and Cooling Thermodynamic Cycle," Science Direct, Applied Energy, vol. 84, No. 3, Nov. 10, 2006, pp. 254-265.
Vidal, "Analysis of a Combined Power and Refrigeration Cycle by the Exergy Method," Science Direct, Energy 31, Dec. 1, 2006, pp. 3401-3414.
Schaschke, "A Dictionary of Chemical Engineering: Tatoray Process," Oxford, 2014, p. 371.
Marcilly, "Acido-Basic Catalysis: Applications to refining and Petrochemistry," IFP Publications, 2005, pp. 512-513.
Gary, "Petroleum Refining Technology and Economics: Figure 1.1 Refinery Flow Diagram," CRC Press, 5th ed., 2007, p. 3.
PCT International Search Report and Written Opinion of the International Searching Authority, PCT/US2016/027417, dated Jul. 6, 2016, 11 pages.
PCT International Search Report and Written Opinion of the International Searching Authority, PCT/US2016/027797, dated Oct. 19, 2016, 12 pages.
PCT International Search Report and Written Opinion of the International Searching Authority, PCT/US2016/027794, dated Oct. 19, 2016, 13 pages.
PCT International Search Report and Written Opinion of the International Searching Authority, PCT/US2016/030063, dated Oct. 19, 2016, 13 pages.
PCT International Search Report and Written Opinion of the International Searching Authority, PCT/US2016/030156, dated Oct. 19, 2016, 12 pages.
PCT International Search Report and Written Opinion of the International Searching Authority, PCT/US2016/048074, dated Nov. 9, 2016, 12 pages.
PCT International Search Report and Written Opinion of the International Searching Authority, PCT/US2016/048042, dated Nov. 9, 2016, 12 pages.
PCT International Search Report and Written Opinion of the International Searching Authority, PCT/US2016/048067, dated Nov. 15, 2016, 11 pages.
PCT International Search Report and Written Opinion of the International Searching Authority, PCT/US2016/048066, dated Nov. 15, 2016, 11 pages.
PCT International Search Report and Written Opinion of the International Searching Authority, PCT/US2016/048078, dated Nov. 15, 2016, 12 pages.
PCT International Search Report and Written Opinion of the International Searching Authority, PCT/US2016/048076, dated Nov. 15, 2016, 12 pages.
PCT International Search Report and Written Opinion of the International Searching Authority, PCT/US2016/048207, dated Nov. 21, 2016, 12 pages.
PCT International Search Report and Written Opinion of the International Searching Authority, PCT/US2016/048219, dated Nov. 21, 2016, 13 pages.
PCT International Search Report and Written Opinion of the International Searching Authority, PCT/US2016/048229, dated Nov. 21, 2016, 13 pages.
PCT International Search Report and Written Opinion of the International Searching Authority, PCT/US2016/048236, dated Nov. 21, 2016, 13 pages.
PCT International Search Report and Written Opinion of the International Searching Authority, PCT/US2016/027413, dated Nov. 22, 2016, 11 pages.
PCT International Search Report and Written Opinion of the International Searching Authority, PCT/US2016/048063, dated Nov. 23, 2016, 11 pages.
PCT International Search Report and Written Opinion of the International Searching Authority, PCT/US2016/048071, dated Nov. 23, 2016, 11 pages.
PCT International Search Report and Written Opinion of the International Searching Authority, PCT/US2016/048210, dated Dec. 22, 2016, 11 pages.
PCT International Search Report and Written Opinion of the International Searching Authority, PCT/US2016/048224, dated Dec. 22, 2016, 11 pages.
PCT International Search Report and Written Opinion of the International Searching Authority, PCT/US2016/048209, dated Dec. 22, 2016, 11 pages.
PCT International Search Report and Written Opinion of the International Searching Authority, PCT/US2016/048237, dated Dec. 22, 2016, 11 pages.
PCT International Search Report and Written Opinion of the International Searching Authority, PCT/US2016/048223, dated Dec. 22, 2016, 11 pages.
PCT International Search Report and Written Opinion of the International Searching Authority, PCT/US2016/048212, dated Dec. 22, 2016, 11 pages.
International Preliminary Report on Patentability in International Application No. PCT/US2016/048042, dated Mar. 8, 2018, 8 pages.
International Preliminary Report on Patentability in International Application No. PCT/US2016/048076, dated Mar. 8, 2018, 8 pages.

(56) References Cited

OTHER PUBLICATIONS

International Preliminary Report on Patentability in International Application No. PCT/US2016/048066, dated Mar. 8, 2018, 8 pages.
International Preliminary Report on Patentability in International Application No. PCT/US2016/048067, dated Mar. 8, 2018, 8 pages.
International Preliminary Report on Patentability in International Application No. PCT/US2016/048078, dated Mar. 8, 2018, 8 pages.
International Preliminary Report on Patentability in International Application No. PCT/US2016/048063, dated Mar. 8, 2018, 8 pages.
International Preliminary Report on Patentability in International Application No. PCT/US2016/048071, dated Mar. 8, 2018, 8 pages.

SYSTEMS FOR RECOVERY AND RE-USE OF WASTE ENERGY IN CRUDE OIL REFINING FACILITY AND AROMATICS COMPLEX

CROSS-REFERENCE TO RELATED APPLICATIONS

This application is a continuation application of and claims the benefit of priority to U.S. patent application Ser. No. 15/242,043, filed on Aug. 19, 2016, which claims priority under 35 U.S.C. § 119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to operating industrial facilities, for example, crude oil refining facilities or other industrial facilities that include operating plants that generate heat.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be reused, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to inter-plants and hybrid, intra- and inter-plants direct or indirect waste heat recovery schemes for integrated refining-petrochemical facilities' thermal energy reduction from waste energy in industrial facilities.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIGS. 1AA-1AF illustrate a fifth set of configurations and related scheme details for thermally integrating an acid gas removal plant and a sulfur recovery plant in the crude oil refining facility with an aromatics plant in the crude oil refining facility.

FIGS. 1AG-1AL illustrate a sixth set of configurations and related scheme details for thermally integrating an acid gas removal plant and a sour water stripper plant in the crude oil refining facility with an aromatics plant in the crude oil refining facility.

FIGS. 1AM-1AT illustrate configurations and related scheme details for thermally integrating an acid gas removal plant, a sour water stripper plant and a sulfur recovery plant in the crude oil facility with an aromatics plant in the crude oil refining facility.

DETAILED DESCRIPTION

Figure 1A:
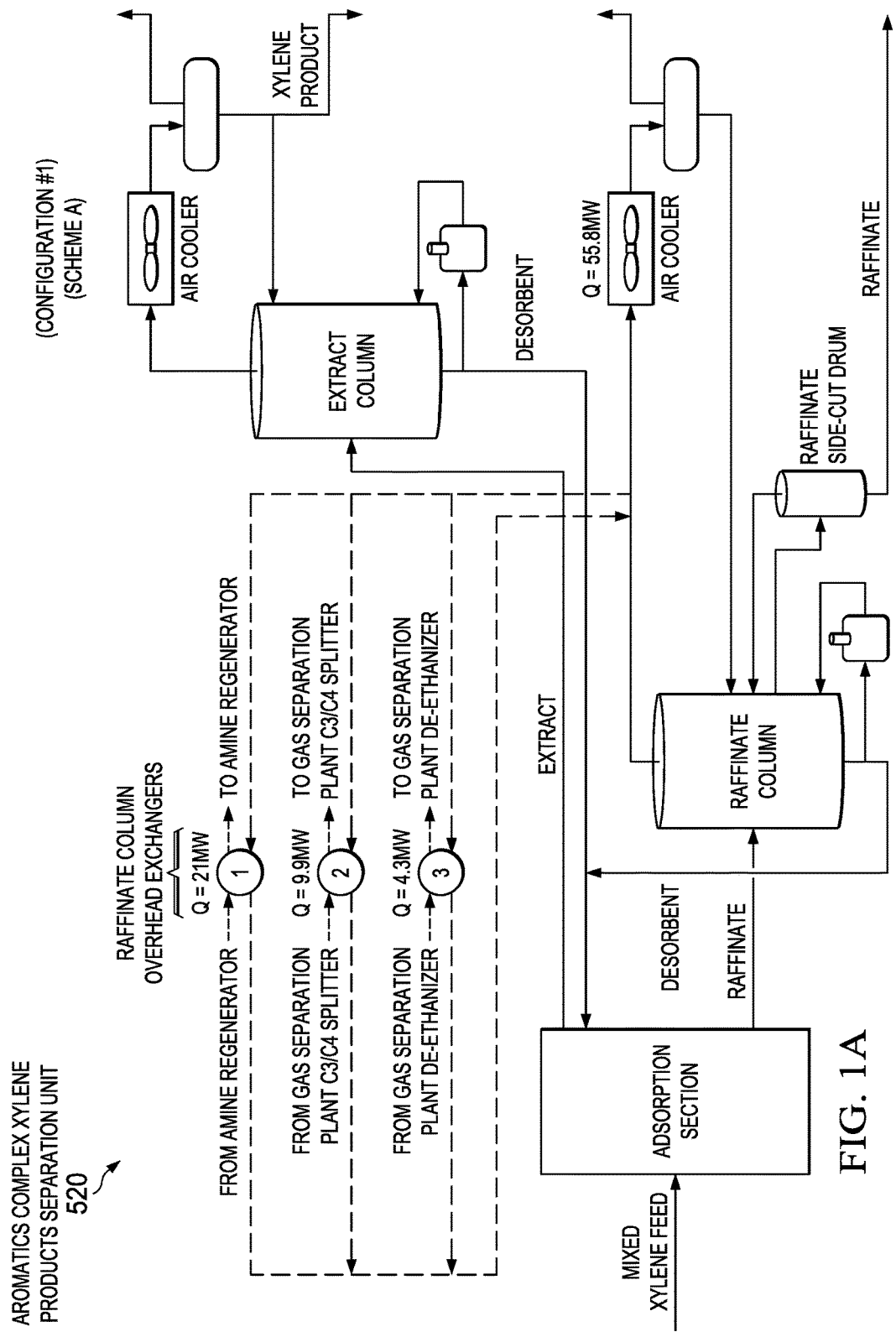
FIGS. 1A-1F illustrate a first set of configurations and related scheme details for thermally integrating refining sub-units of an aromatics plant in the crude oil refining facility and other plants in the crude oil refining facility.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM British Thermal Units per hour (Btu/hr) can be wasted to a network of air coolers extended along the crude oil and aromatics site. Some of the wasted heat can be reused to heat streams in refining sub-units of the crude oil refinery, thereby decreasing a quantity of heat that would otherwise need to be used to heat the streams. In this manner, a quantity of heat consumed by the crude oil refinery can decrease. In addition, a quantity of greenhouse gas (GHG) emission can also decrease. In some implementations, a reduction of about 34% in heating utility consumption and a reduction of about 20% in cooling utility consumption can be achieved without affecting an operational philosophy of the crude oil refinery.

The waste heat recovery and reuse techniques described here can be implemented in medium grade crude oil refining semi-conversion facilities and integrated medium grade crude oil refining semi-conversion oil refining and aromatics facilities. The implementations can result in energy efficient systems that can consume about 66% of the heating utility consumed by current state-of-the-art designs of existing and new crude oil refining facilities. The implementations can also result in decrease in pollution and in GHG emissions by about one-third relative to GHG emissions from current state-of-the-art designs of existing and new crude oil refining facilities.

In certain existing oil refining facilities, a stream in a plant (for example, a naphtha hydro-treating plant, a sour water stripper plant, or other plant) is heated using heat energy generated in a steam reboiler. In some implementations of the subject matter described here, the stream in the plant can be heated using waste heat carried by another stream in another plant (for example, a hydrocracking plant, a hydrotreating plant, a hydrogen plant, or other plant). By doing so, the heat energy generated in the steam reboiler can be decreased or eliminated. In other words, the steam reboiler need not be the only source of heat energy to heat the stream in the plant. The waste heat carried by the other stream in the other plant can either replace the heat energy generated in the steam reboiler or supplement the heat energy thereby decreasing a quantity of heat energy needed from the steam reboiler.

The subject matter described here can be implemented at different plants' specific operating modes and can be retrofitted without the need to change the network designs of existing heat exchanger designs in crude oil refineries. The minimum approach temperature used in the waste heat recovery and reuse processes can be as low as 3° C. In some implementations, higher minimum approach temperatures can be used in an initial phase at the expense of less waste heat/energy recovery, while relatively better energy saving is realized in a subsequent phase upon using the minimum approach temperature for the specific hot sources uses.

In sum, this disclosure describes several crude oil refinery-wide separation/distillation networks, configurations, and processing schemes for increasing energy efficiency of heating/cooling utilities. The increase in energy efficiency is realized by reusing all or part of waste heat, for example, low grade waste heat, carried by multiple, scattered low grade energy quality process streams.

Examples of Crude Oil Refinery Plants

1. Hydrogen Plant

Hydrogen is generally used in refineries for sulfur removal and quality improvement of hydrocarbon products. As sulfur restrictions on gasoline and diesel become stringent, the refining demand for hydrogen continues to grow. Two process schemes are employed in on-purpose hydrogen generation plants—conventional process and pressure swing adsorption (PSA) based process. Hydrogen production can include hydro-desulfurization, steam reforming, shift conversion and purification. The conventional process produces a medium-purity hydrogen, whereas the PSA-based process recovers and purifies the hydrogen to high purities, for example, purities greater than 99.9%.

2. Aromatics Complex

A typical aromatics complex includes a combination of process units for the production of basic petrochemical intermediates of benzene, toluene and xylenes (BTX) using the catalytic reforming of naphtha using continuous catalytic reformer (CCR) technology.

3. Gas Separation Plant

A gas separation plant includes a de-ethanizer and a de-propanizer, which are distillation columns used to isolate ethane and propane, respectively, in natural gas liquids (NGL) and light ends fractionation in gas plants and refineries. The de-ethanizer removes ethane from a mixture of propane, butane and other heavier components. An output of the de-ethanizer is fed to a de-propanizer to separate propane from the mixture.

4. Amine Regeneration Plant

Hydrogen sulfide and carbon dioxide are the most common contaminants present in natural gas and are present in relatively larger quantities than other contaminants which can adversely impact the natural gas processing facility if not removed. Amine is used to sweeten sour gases in a chemical process in which a weak base (for example, the amine) reacts with weak acids such as hydrogen sulfide and carbon dioxide to form a weak salt.

5. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromatics content or high concentrations of the two principal catalyst poisons, sulfur and nitrogen compounds (or combinations of them).

The hydrocracking process depends on the nature of the feedstock and the relative rates of the two competing reactions, hydrogenation and cracking. Heavy aromatics feedstock is converted into lighter products under a wide range of high pressures and high temperatures in the presence of hydrogen and special catalysts. When the feedstock has a high paraffinic content, hydrogen prevents the formation of polycyclic aromatics compounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces iso-butane for alkylation feedstock, and also performs isomerization for pour-point control and smoke-point control, both of which are important in high-quality jet fuel.

6. Diesel Hydrotreating Plant

Hydrotreating is a refinery process for reducing sulfur, nitrogen and aromatics while enhancing cetane number, density and smoke point. Hydrotreating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

7. Sour Water Stripper Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

8. Sulfur Recovery Plant

Sulfur recovery facilities in refineries operate to regulate the discharge of sulfur compounds to the atmosphere to meet environmental regulations. In a sulfur recovery plant, combustion products that include sulfur can be processed, for example, by heating, cooling with condensers, using sulfur conversion catalyst, and by other processing techniques. One technique is to use amines to extract the sulfur and other acid gas compounds.

9. Naphtha Hydrotreating Plant and Continuous Catalytic Reformer Plants

A Naphtha Hydrotreater (NHT) produces 101 Research Octane Number (RON) reformate, with a maximum 4.0 psi (pounds per square inch) Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the CCR platformer and gasoline blending.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, i.e., the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with threats that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Configurations in which heat exchangers are described as being in series can have multiple implementations. In some implementations, the heat exchangers can be arranged in series in one order (for example, a first heat exchanger, a second heat exchanger and a third heat exchanger in that order) while in other implementations, the heat exchangers can be arranged in series in a different order (for example, a third heat exchanger, a first heat exchanger and a second heat exchanger in that order). In other words, a first heat exchanger described as being in series with and downstream of a second heat exchanger in one implementation can be in series with and upstream of the second heat exchanger in a second, different implementation.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This disclosure describes new energy efficient configurations and the related specific inter-processing schemes for integrated medium grade semi-conversion crude oil refining facility and aromatics complex.

In some implementations, a semi-conversion medium grade crude oil refining facility includes an aromatics complex. This disclosure describes a waste heat recovery and reuse network for such a refining facility. As described later, waste heat can be recovered from one or more of the units in the aromatics plant. Such a refinery typically consumes several hundred megawatts of energy in heating utilities. Implementing the configurations described here can not only reduce energy consumption but also reduce energy-based greenhouse gas (GHG) emissions. In particular, this disclosure describes a method implemented in a crude oil refining facility to heat multiple streams in multiple plants of a crude oil refining facility using one or more streams in one or more aromatics plant sub-units included in an aromatics plant in the crude oil refining facility. Several configurations of process schemes for doing so are described later with reference to the following figures.

Configuration 1

FIGS. 1A-1F illustrate configurations and related scheme details for thermally integrating refining sub-units of an aromatics plant in the crude oil refining facility and other plants in the crude oil refining facility. In some implementations, the aromatics complex sub-units can include an aromatics complex xylene products separation unit. The other plants in the crude oil refining facility can include a sulfur recovery plant and a gas separation plant. The thermal integration described in these configurations and illustrated in FIGS. 1A-1F can reduce the crude oil refining facility's energy consumption (for example, heating and cooling utilities). For example, a reduction in energy consumption by about 35 MW, for example, 35.2 MW, can translate to at least about 5% of the energy consumption in the crude oil refining facility. In certain schemes, a process stream (for example, a stream from one refining sub-unit of an aromatics complex or other process streams) can be used to directly heat another process stream (for example, a sulfur plant stream or other process stream). In certain configurations, heat exchange between process streams can be implemented using an intermediate buffer fluid, for example, water, oil, or other buffer fluid.

Configuration 1—Scheme A

The multiple streams in the crude oil refining facility sulfur recovery plant and a gas separation plant can be directly heated using the one or more streams in the one or more aromatics complex xylene separation unit. In some implementations, multiple first streams in first multiple plants plant can be directly heated using a second stream in a second plant. In some implementations, the first plants are the sulfur recovery plant and a gas separation plant; the multiple first streams are the amine regenerator bottoms, the C3/C4 splitter bottoms, and the de-ethanizer bottoms; the second plant is the aromatics complex xylene separation unit and the second stream is the raffinate overhead column stream.

FIG. 1A shows an aromatics complex xylene products separation unit 520 that includes a raffinate column overhead stream. The raffinate overheads column stream can be flowed in the plant as a single stream and split into multiple streams or it can be flowed into the plant as multiple streams to facilitate heat recovery. The first raffinate column overheads stream can directly heat a amine regenerator bottom stream in a first heat exchanger with a thermal duty that can range between about 15 MW and 25 MW (for example, 21 MW). The second raffinate column overheads stream can directly heat a C3/C4 splitter bottom stream in a second heat exchanger with a thermal duty that can range between about 5 MW and 15 MW (for example, 9.9 MW). The third raffinate column overheads stream can directly heat a de-ethanizer bottom stream in a third heat exchanger with a thermal duty that can range between about 1 MW to 10 MW (for example, 4.3 MW). The transfer of heat directly to another process stream captures heat that would have otherwise been discharged to the environment. In this manner, the first heat exchanger, the second heat exchanger, and the third heat exchanger can be coupled in parallel to one another relative to the flow of the raffinate column overhead stream. The raffinate column overheads streams are recombined and returned to the aromatics complex xylene product separation unit 520 for further processing.

Figure 1B:
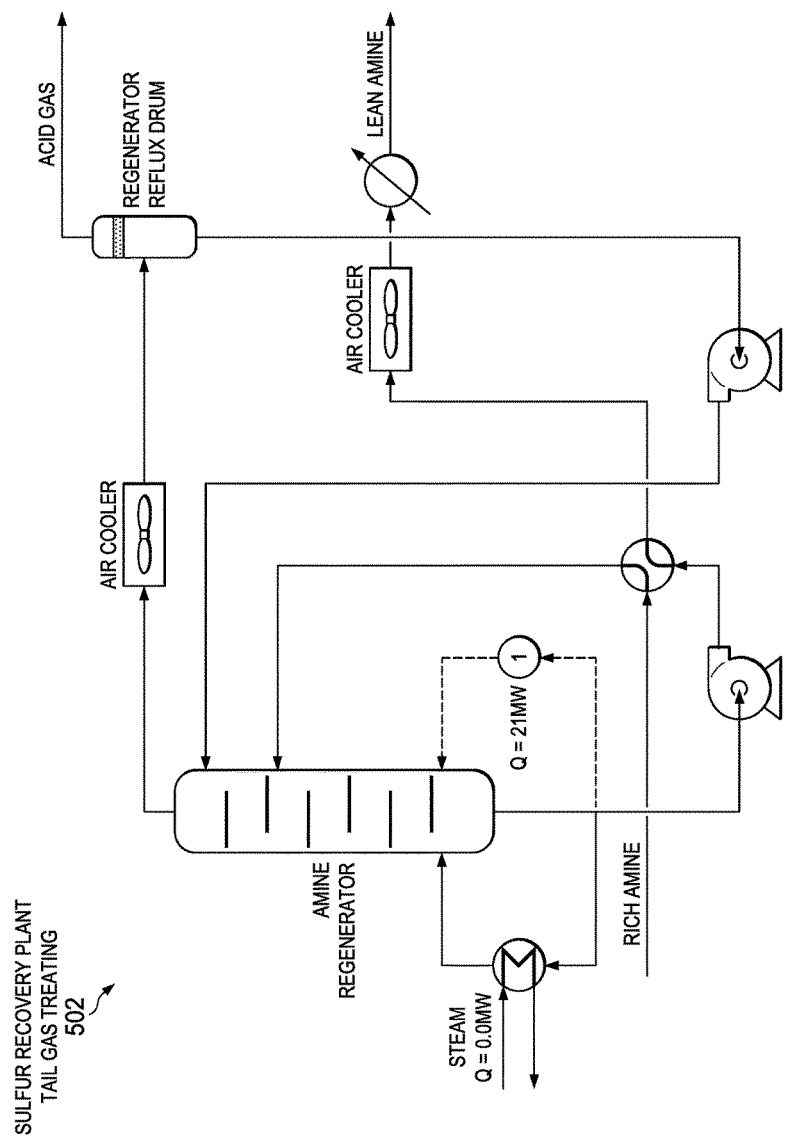

FIG. 1B shows the sulfur recovery plant 502 in the crude oil refinery facility. The heated amine regenerator bottoms stream can then be flowed to the sulfur recovery plant 502. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

Figure 1C:
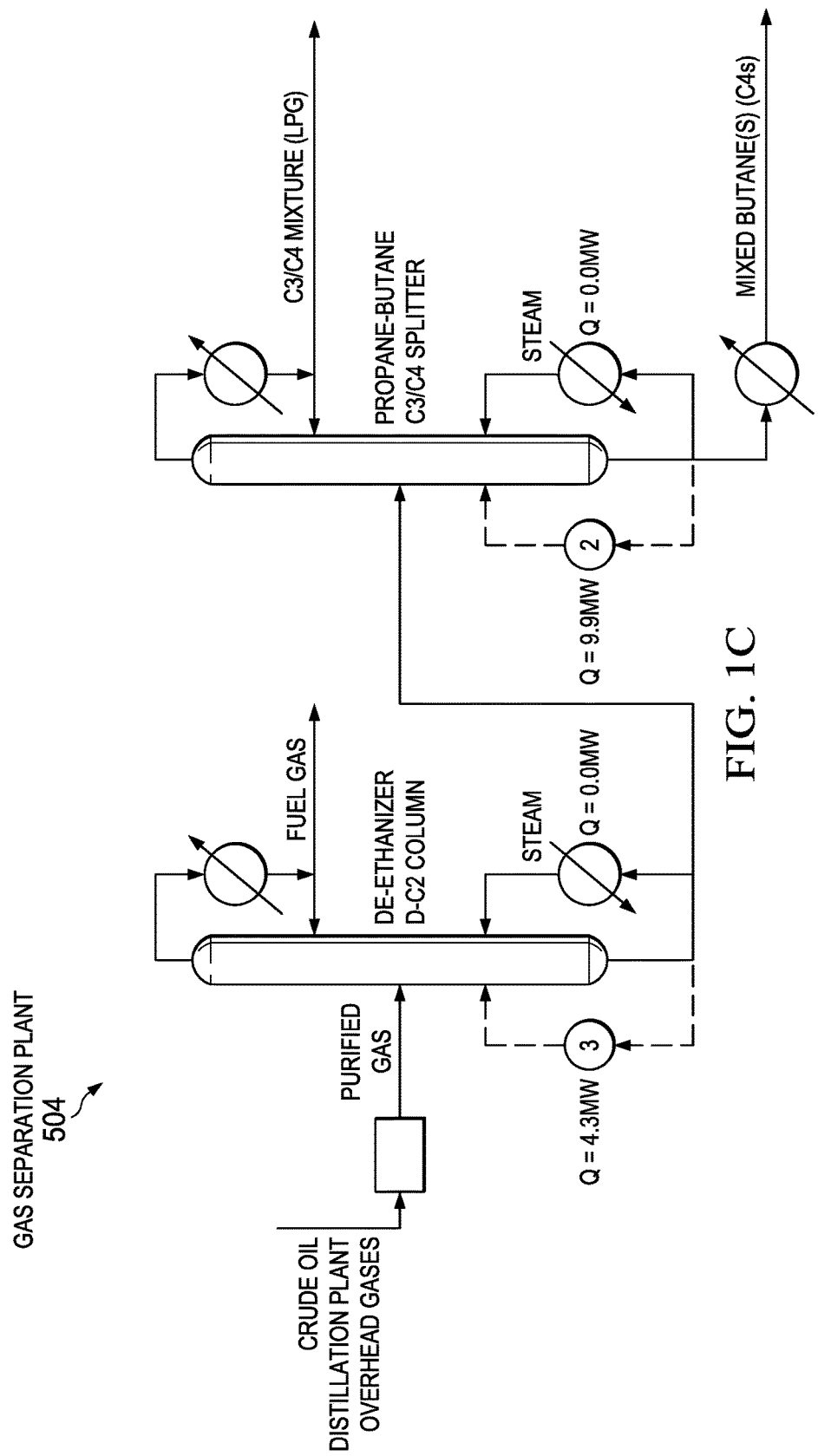

FIG. 1C shows the gas separation plant 504 in the crude oil refinery facility. The heated C3/C4 splitter bottoms stream can be flowed to the gas separation plant 504. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

The heated de-ethanizer bottoms stream can be flowed to the gas separation plant 504. As shown in FIG. 1C, the steam heat input for the de-ethanizer can be 0 MW because the alternative flow path disclosed in this configuration may satisfy the entire heat load for the operation of the column. In an alternative embodiment, the steam heat input for the de-ethanizer can be reduced because the alternative flow path disclosed in this configuration may partially satisfy the heat load for the operation of the column.

Such recovery and reuse of waste heat directly from the aromatics complex can result in decreasing or eliminating the heat energy to heat the sulfur recovery plant or the gas separation plant or a combinations of them such as by about 35 MW.

Configuration 1—Scheme B

In some implementations, the multiple first streams in multiple first plants in the crude oil refining facility can be indirectly heated using a second stream in a second plant. In some implementations, the multiple first plants include a sulfur recovery plant and a gas separation plant; the multiple first streams include an amine regeneration bottoms stream, a de-ethanizer bottoms stream, and a C3/C4 splitter bottoms stream; the second plant includes an aromatics complex xylene separation unit; and the second stream includes raffinate column overheads stream.

Figure 1D:
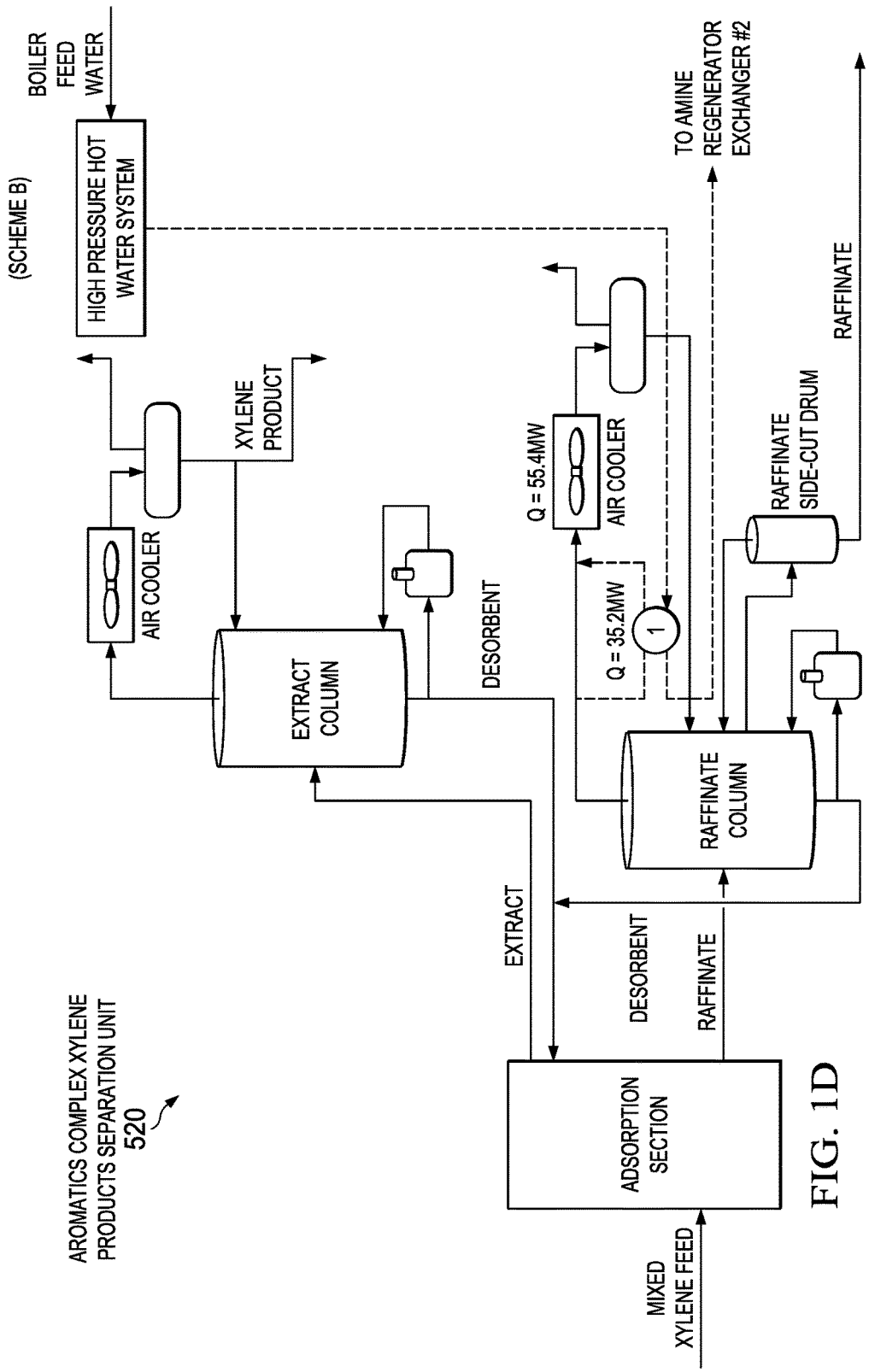
Figure 1E:
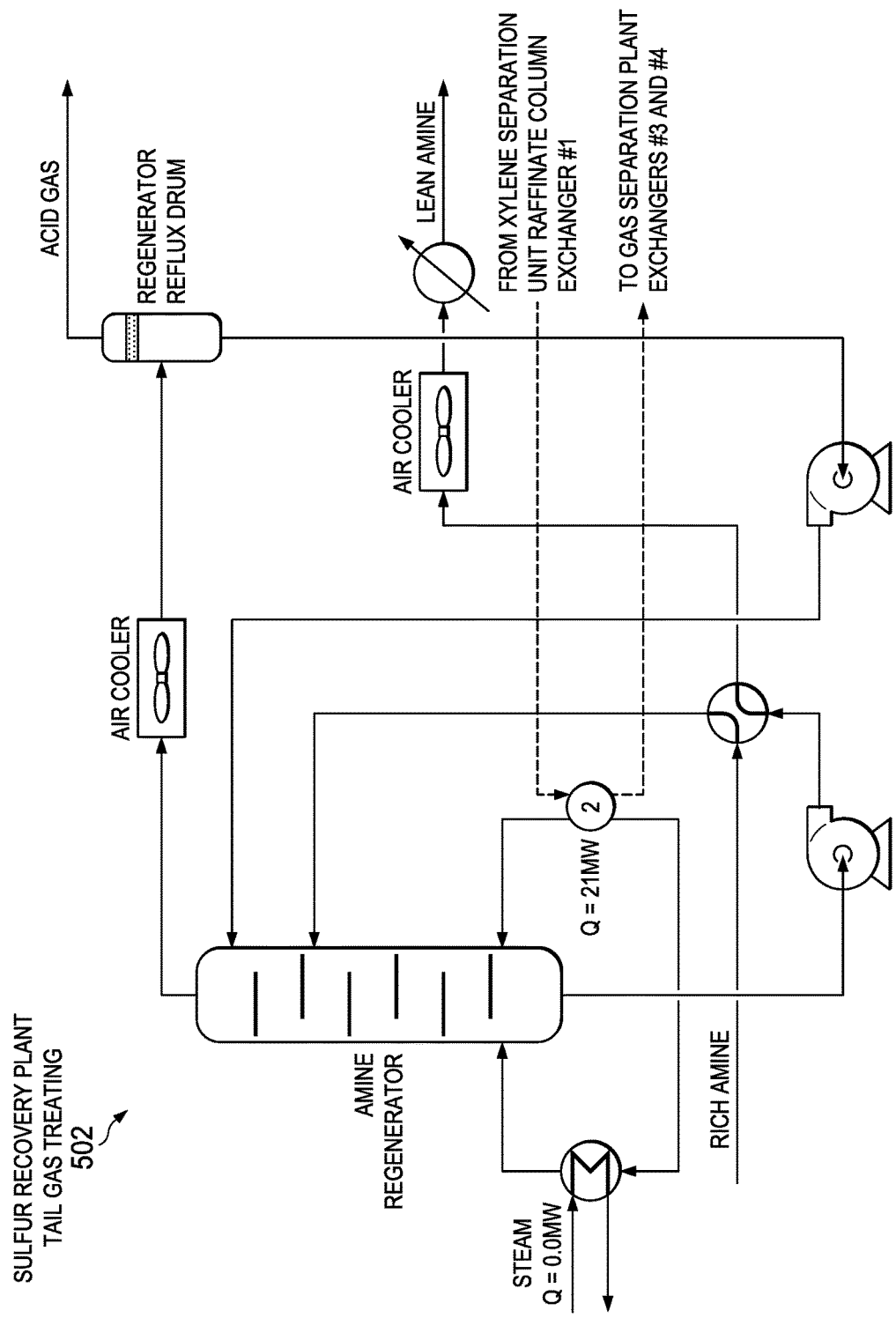
Figure 1F:
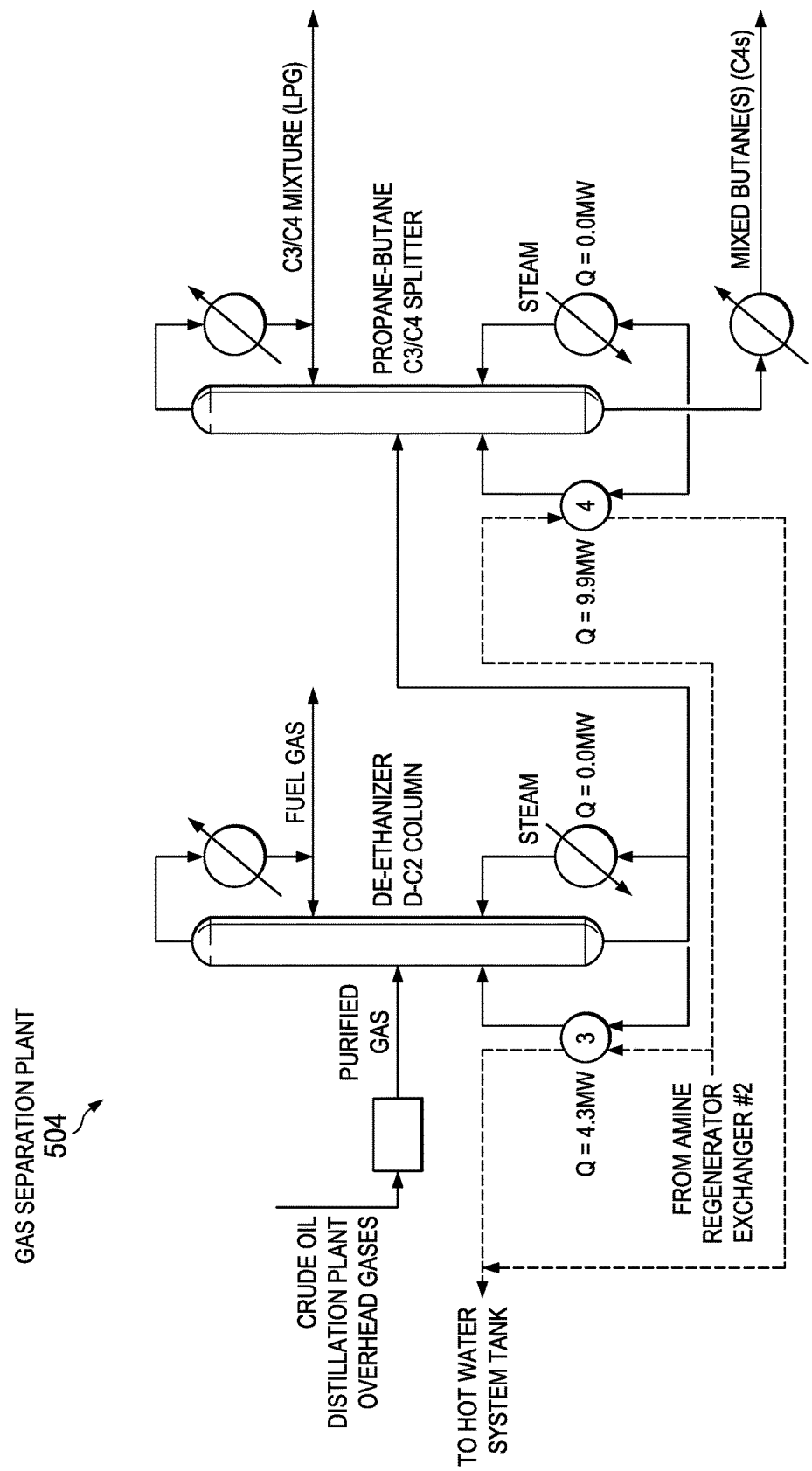

FIGS. 1D-1F illustrate configurations and related scheme details for thermally integrating different refining plants in the crude oil refining facility. The thermal integration described in these configurations and illustrated in FIGS. 1D-1F can reduce the crude oil refining facility's energy consumption (for example, heating and cooling utilities). For example, a reduction in energy consumption by about 35 MW, for example, 35.2 MW, can translate to at least about 5% of the energy consumption in the crude oil refining facility. In certain configurations, heat exchange between process streams can be implemented using an intermediate buffer fluid, for example, water, oil, or other buffer fluid.

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene products separation unit 520. The buffer fluid can be flowed into the plant as a single stream and split into multiple streams or it can be flowed into the plant as multiple streams.

FIG. 1D shows an aromatics complex xylene products separation unit 520. To do so, a buffer fluid from a buffer fluid collection tank is flowed to the aromatics complex xylene products separation unit 520. The buffer fluid can be heated using an aromatics complex xylene products separation 520 raffinate column overhead stream in a first heat exchanger with a thermal duty that can range between about 30 MW and 40 MW (for example, 35.2 MW). The buffer fluid absorbs heat that would have otherwise been discharged to the environment. The raffinate column overheads stream is returned to the xylene products separation unit 520 for further processing.

The heated buffer fluid is directed to a collection header (or in some embodiments, a heated or insulated buffer fluid tank or storage unit that can hold heated collected buffer fluid for a period before use) and then can be flowed to either the sulfur recovery plant 502 and the gas separation plant 504.

FIG. 1E shows the sulfur recovery plant 502 in a crude oil refinery facility. The heated buffer fluid is flowed to the sulfur recovery plant 502. An amine regenerator bottoms stream is heated using the heated buffer fluid in a second heat exchanger with a thermal duty that can range between about 15 MW and 25 MW (for example, 21 MW). The second heat exchanger is coupled to, in series with and is downstream of the first heat exchanger relative to the flow of heated buffer fluid. As shown in FIG. 1E, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1F shows the gas separation plant 504 in a crude oil refinery facility. The heated buffer fluid exiting the second heat exchanger is split into a first heated buffer fluid stream and a second heated buffer fluid stream and flowed to the gas separation plant 504. A de-ethanizer bottoms stream is heated using the first heated buffer fluid branch in a third heat exchanger with a thermal duty that can range between about 1 MW and 10 MW (for example, 4.3 MW). The third heat exchanger is coupled to, in series with and is downstream of the first heat exchanger relative to the buffer fluid flow. As shown in FIG. 1F, the steam heat input for the de-ethanizer can be 0 MW because the alternative flow path disclosed in this configuration may satisfy the entire heat load for the operation of the column. In an alternative embodiment, the steam heat input for the de-ethanizer can be reduced because the alternative flow path disclosed in this configuration may partially satisfy the heat load for the operation of the column.

As shown in FIG. 1F, a C3/C4 splitter bottoms stream is heated using the second heated buffer fluid stream in a fourth heat exchanger with a duty that can range between about 5 MW to 15 MW (for example, 9.9 MW). The fourth heat exchanger is coupled to, in series with and is downstream of the first heat exchanger relative to the buffer fluid flow. The third and the fourth heat exchangers are coupled in parallel to one another relative to the flow of buffer fluid flow. As shown in FIG. 1F, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

The heated buffer fluid exiting the third and the fourth heat exchangers are flowed to the collection header or the buffer fluid tank for reuse. In this manner, the second and set of the third and the fourth heat exchangers are coupled to each other in series relative to the flow of the heated buffer fluid.

In some implementations, the heated buffer fluid can be flowed in series through the different plants. For example, the heated buffer fluid can be flowed first to the gas separation plant then to the sulfur recovery plant. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly from the aromatics complex can result in decreasing or eliminating the heat energy to heat the sulfur recovery plant or the gas separation plant or combinations of them, such as by about 35 MW.

Configuration 2

FIGS. 1G-1N illustrate configurations and related scheme details for thermally integrating refining sub-units and a hydrogen plant in the crude oil refining facility and other plants in the crude oil refining facility. In some implementations, the refining sub-units include a diesel hydrotreating plant. The hydrogen plant can also be known as a natural gas steam reforming hydrogen plant. The other plants in the crude oil refining facility can include an benzene extraction unit and sour water stripper plant. In certain schemes, a process stream (for example, a stream from one refining sub-unit or the hydrotreating plant or other process streams) can be used to directly heat another process stream (for example, a sour water stripper plant stream or other process stream). In certain configurations, heat exchange between process streams can be implemented using an intermediate buffer fluid, for example, water, oil, or other buffer fluid.

The thermal integration described in these configurations and illustrated in FIGS. 1G-1N can reduce the crude oil refining facility's energy consumption (for example, heating and cooling utilities). For example, a reduction in energy consumption by about 41 MW can translate to at least about 6% of the energy consumption in the crude oil refining facility.

Configuration 2—Scheme A

The multiple streams in sub-units of the crude oil refining facility can be directly heated using the one or more streams from the diesel hydrotreating plant or the hydrogen plant, or both. In some implementations, the multiple streams in the benzene extraction unit and the sour water stripper plant can be directly heated using the streams in the natural gas steam reforming hydrogen plant and the diesel hydro-treating plant. In some implementations, a first stream in a first plant can be directly heated using a second stream in a second plant, while a third stream in a third plant can be directly heated using multiple streams in a fourth plant. In some implementations, the first plant is an benzene extraction unit and the first stream is the raffinate splitter bottoms; the second plant is a natural gas steam reforming hydrogen plant and the second stream is the low temperature shift (LTS) converter product stream; the third plant is a sour water stripper plant and the third stream is the sour water stripper bottoms; and the fourth plant is a diesel hydrotreating plant and the multiple fourth plant streams include the diesel stripper overheads and the diesel stripper bottoms.

Figure 1G:
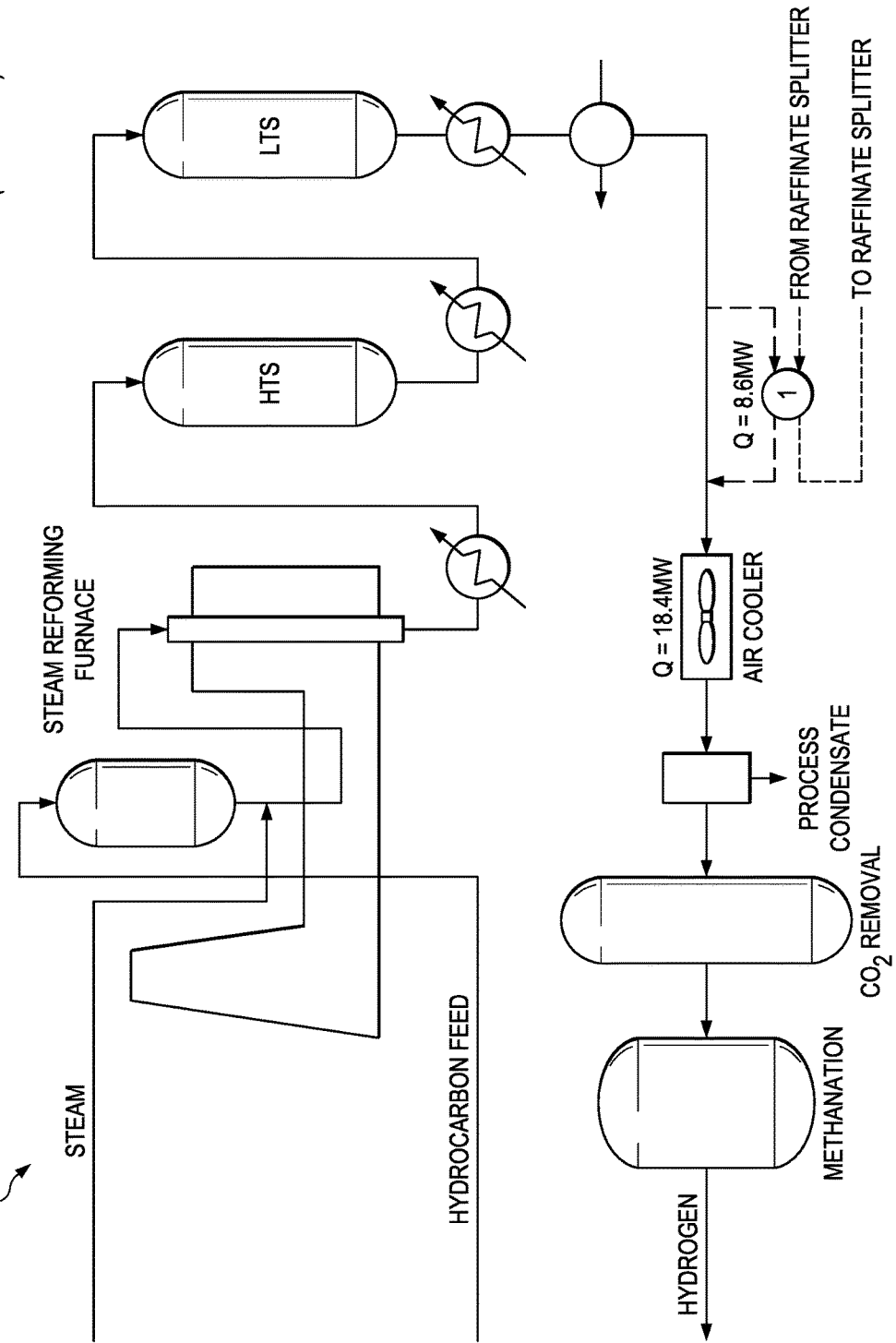
FIGS. 1G-1N illustrate a second set of configurations and related scheme details for thermally integrating an aromatics plant and a sour water stripper plant in the crude oil refining facility with other plants in the crude oil refining facility, for example, a hydrogen plant and a diesel hydro-treating plant.

FIG. 1G shows the natural gas steam reforming hydrogen plant 508 in a crude oil refinery facility. The LTS converter product stream can directly heat a raffinate splitter bottom stream in a first heat exchanger with a thermal duty ranging between about 5 MW and 15 MW (for example, 8.6 MW). The transfer of heat directly to another process stream captures heat that would have otherwise been discharged to the environment. The LTS converter product stream is returned to the natural gas steam reforming hydrogen plant 508 for further processing.

Figure 1H:
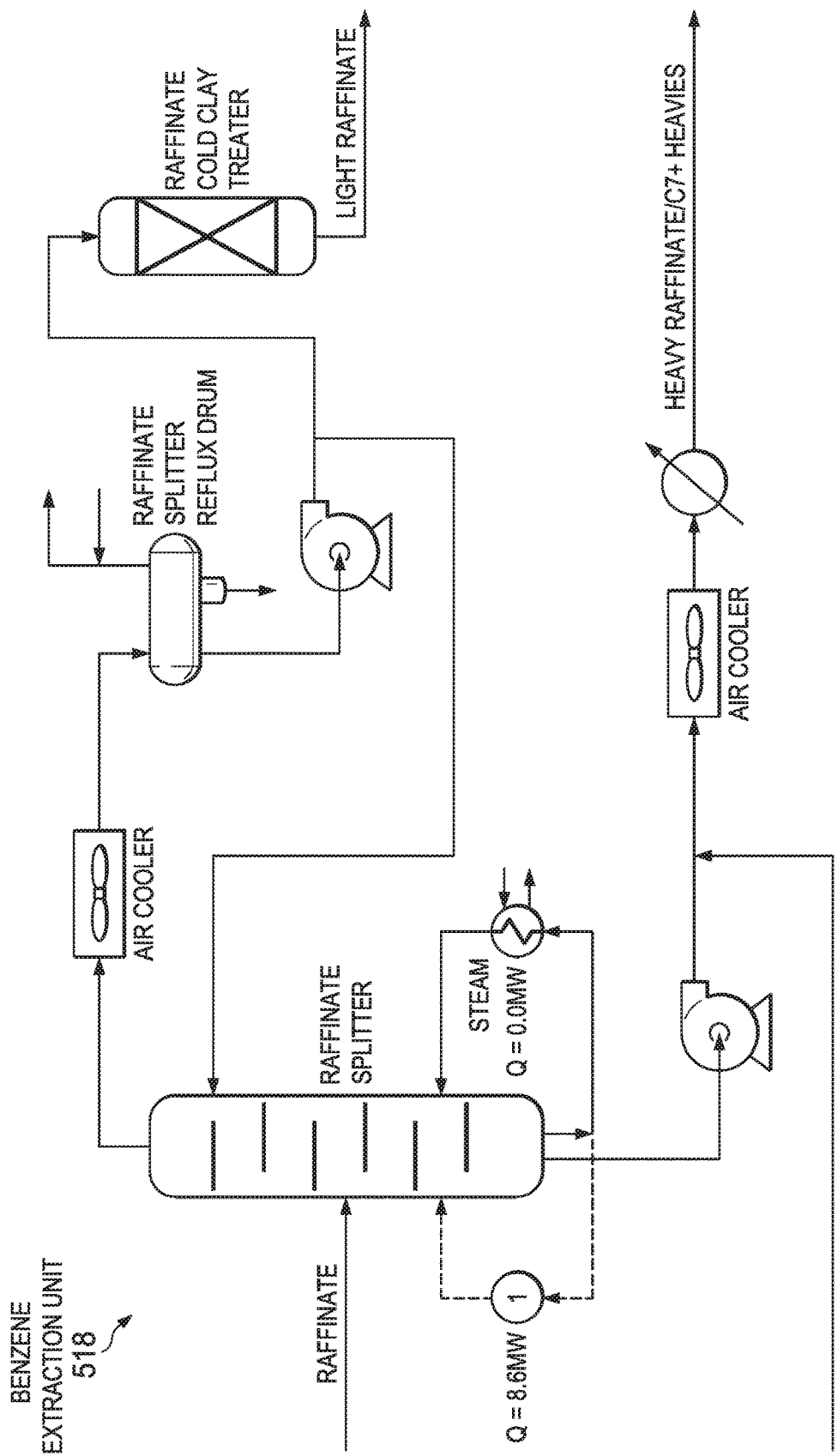

FIG. 1H shows the benzene extraction unit 518 in the crude oil refinery facility. The heated raffinate splitter bottom stream is directed to the benzene extraction unit 518. As shown in FIG. 1H, the steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

Figure 1I:
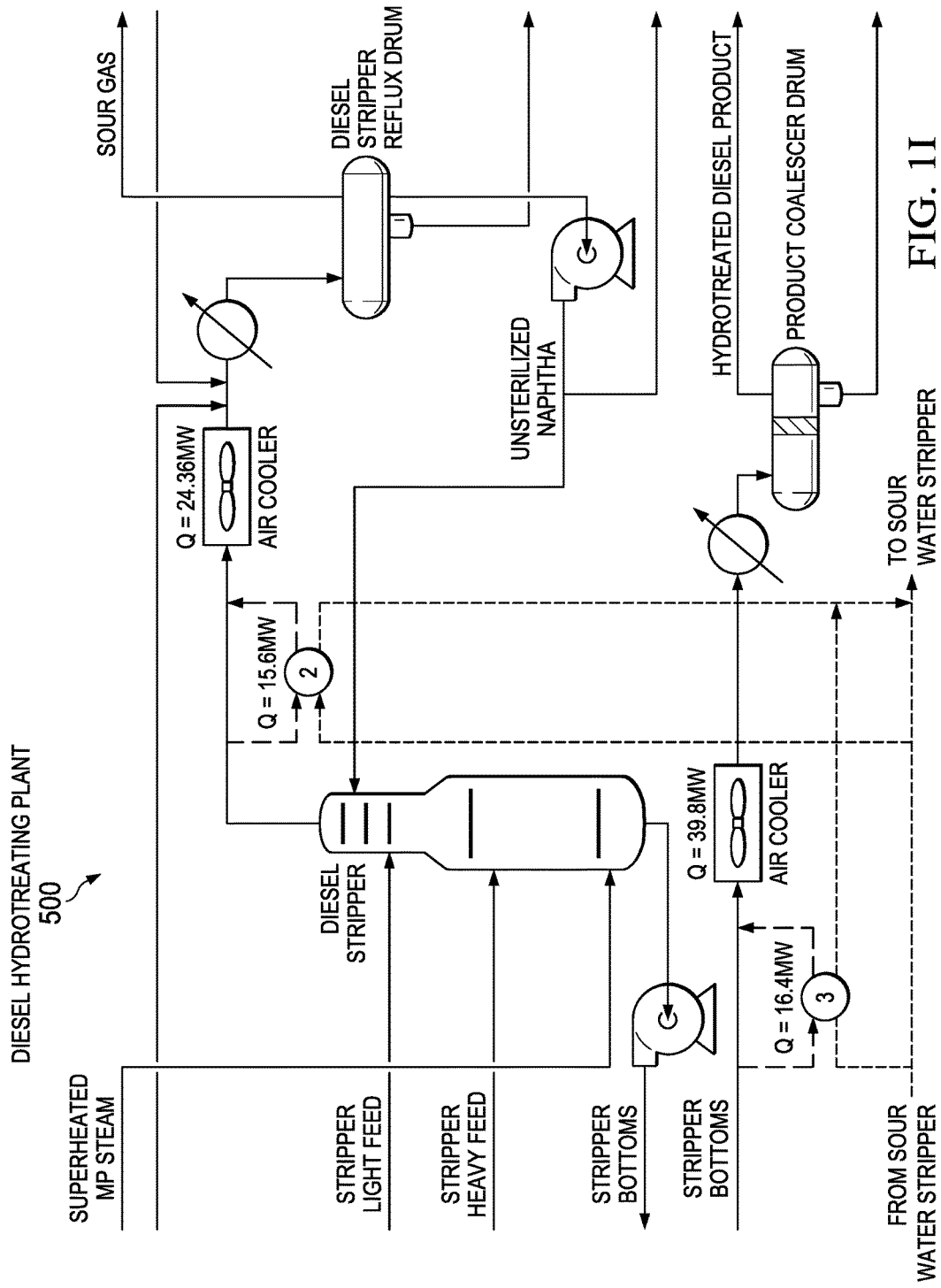
Figure 1J:
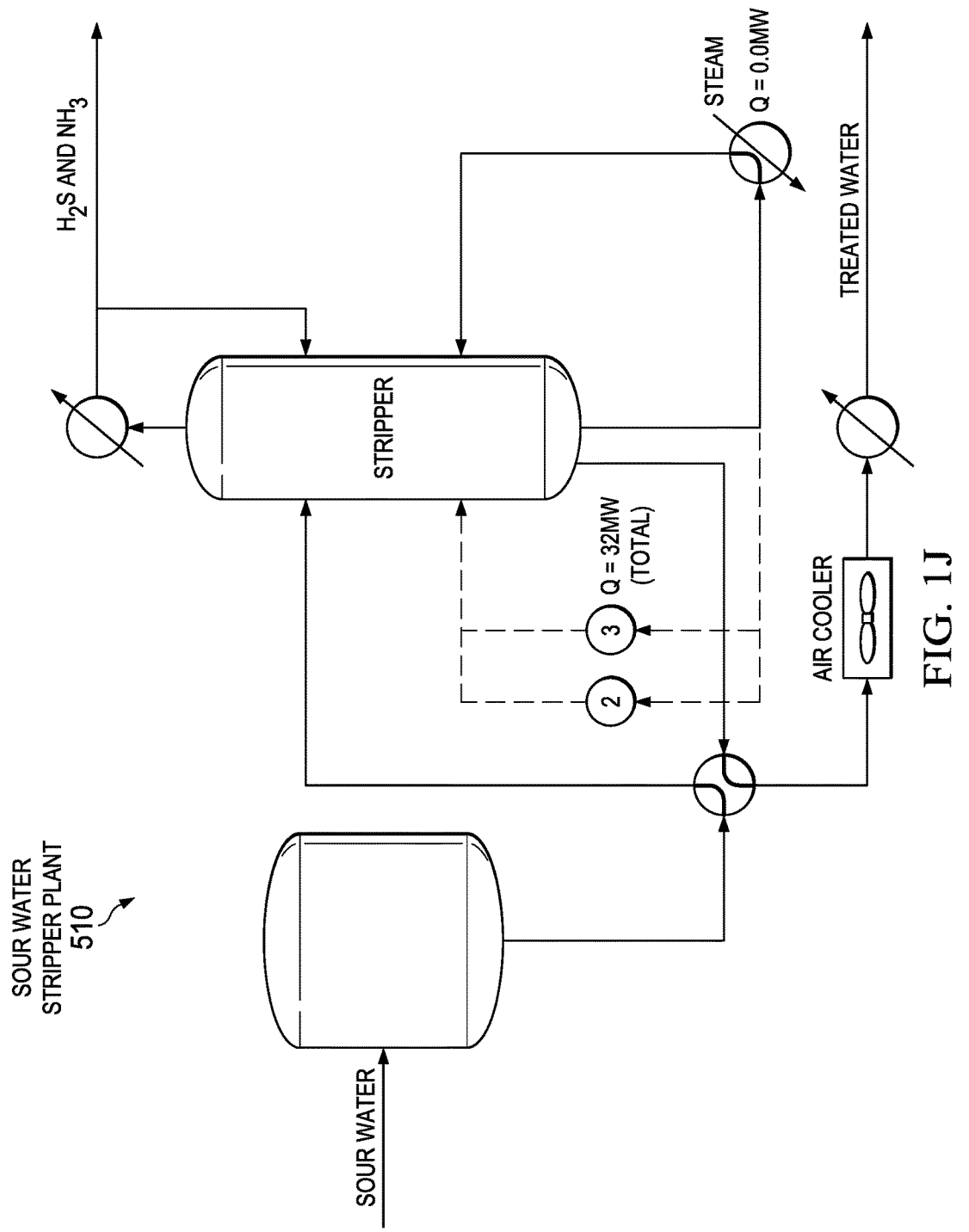

FIG. 1I shows the diesel hydrotreating plant 500 in the crude oil refinery facility. FIG. 1J shows the sour water stripper plant 510 in the crude oil refinery facility. The sour water stripper bottoms stream can be flowed in the plant as a single stream and split into multiple streams or it can be flowed into the plant as multiple streams. In FIG. 1I, the diesel hydrotreating plant can directly heat a sour water stripper bottoms stream that is split into a first stream and a second stream to facilitate heat recovery. As shown in 1I, the first sour water stripper bottoms stream can be directly heated using a diesel stripper overheads stream in a second heat exchanger with a thermal duty that can range between about 10 MW and 20 MW (for example, 15.6 MW). Also, the second sour water stripper bottoms stream can be heated using a diesel stripper bottoms stream in a third heat exchanger with a thermal duty that can range between about 10 MW and 20 MW (for example, 16.4 MW. In both instances, the transfer of heat directly to another process stream captures heat that would have otherwise been discharged to the environment. The second heat exchanger and the third heat exchanger are coupled together in parallel relative to the flow of sour water stripper bottoms.

The first and second heated sour water splitter bottoms streams are recombined and flowed to the sour water stripper plant 510. As shown in FIG. 1J, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column. The parallel exchangers capture heat that would have otherwise been discharged to the environment.

Such recovery and reuse of waste heat directly from the natural gas steam reforming hydrogen plant and the diesel hydrotreating plant can result in decreasing or eliminating the heat energy to heat the benzene extraction unit or the sour water stripper plant or a combinations of them, such as by about 41 MW.

Configuration 2—Scheme B

In some implementations, the multiple streams in the crude oil refining facility such as those present in the sour water stripper plant and the benzene extraction unit, can be indirectly heated using a buffer fluid, for example, oil, water or other buffer fluid, using the streams in the hydrogen plant and the diesel hydro-treating plant as heat energy sources. In some implementations, the multiple first streams in multiple first plants can be indirectly heated using a buffer fluid, for example, oil, water or other buffer fluid, using multiple second streams in multiple second plants. In some implementations, the multiple first plants include a sour water stripper plant and a benzene extraction unit; the multiple first streams include a sour water stripper bottoms stream and a raffinate splitter bottoms stream; the multiple second plants include a natural gas steam reforming hydrogen plant and a diesel hydrotreating plant; and the multiple second streams includes the low temperature shift (LTS) converter product, the diesel stripper overheads, and the diesel stripper bottoms streams.

Indirectly heating the streams can include heating the streams through a buffer fluid, for example, oil, water, or other buffer fluid. A buffer fluid (for example, high pressure water) from a buffer fluid tank (for example, hot water tank) is flowed both to the natural gas steam reforming hydrogen plant 508 and the diesel hydrotreating plant 500. The buffer fluid can be flowed into each plant as a single stream and split into multiple streams or it can be flowed into a plant as multiple streams.

Figure 1K:
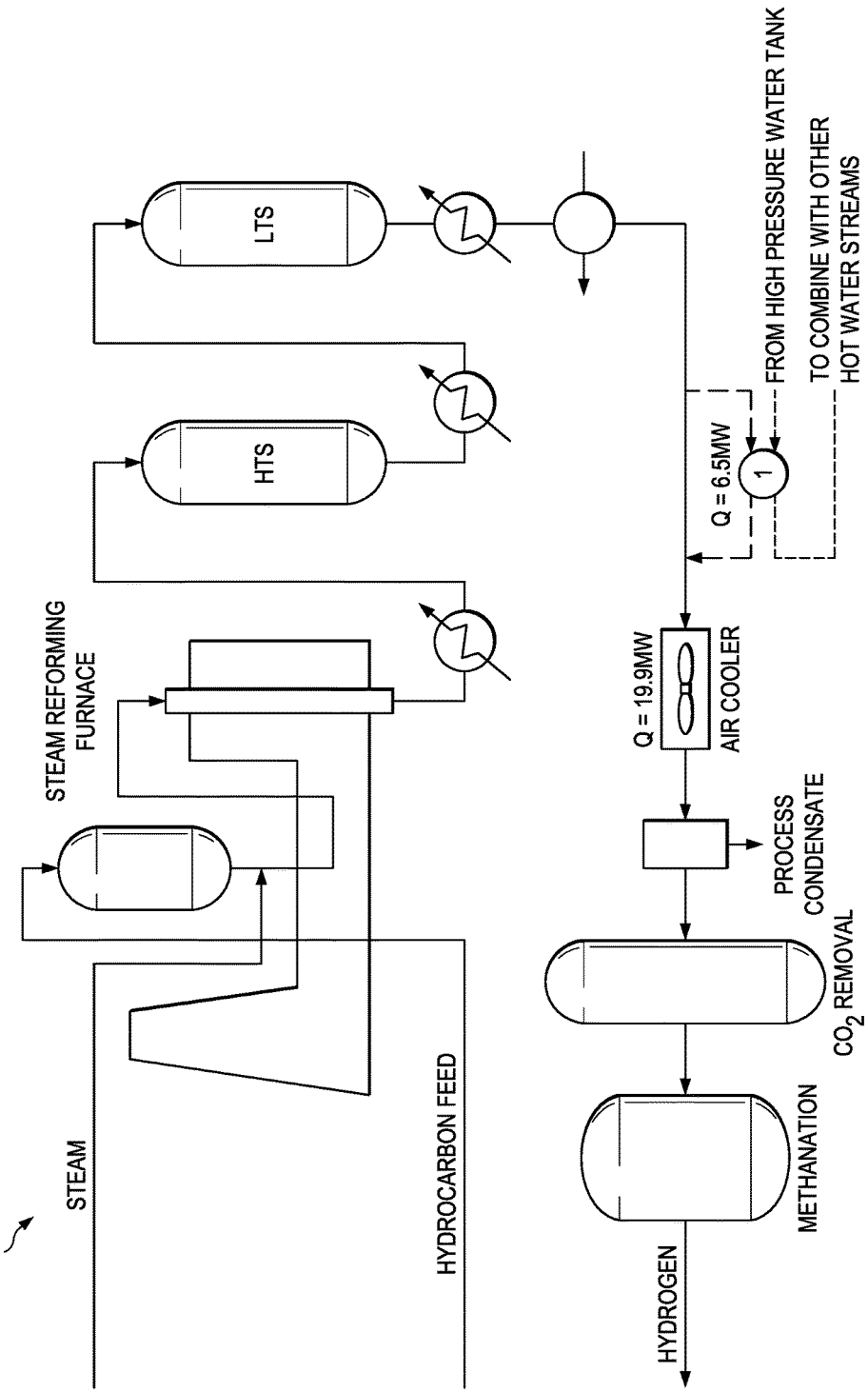

FIG. 1K shows the natural gas steam reforming hydrogen plant 508 in the crude oil refining facility. To do so, a first buffer fluid steam is flowed from a buffer fluid tank (for example, water from a high pressure water tank) to the natural gas steam reforming hydrogen plant 508. As shown in FIG. 1K, the first buffer fluid stream is heated using LTS converter product stream in a first heat exchanger with a thermal duty that can range between about 1 MW and 10 MW (for example, 6.5 MW). The buffer fluid absorbs heat that would have otherwise been discharged to the environment. The LTS converter product stream is returned to the natural gas steam reforming hydrogen plant 508 for further processing.

Figure 1L:
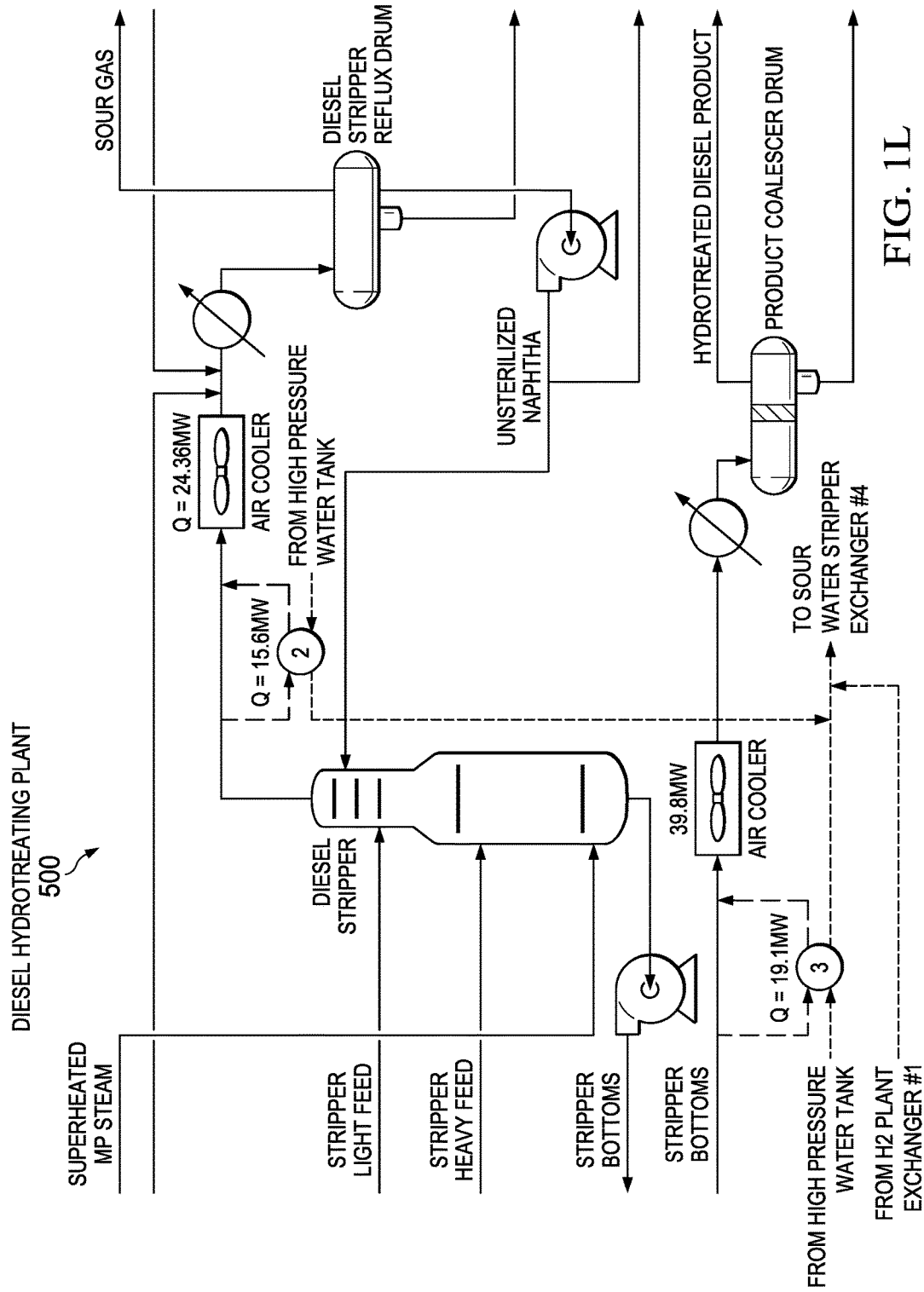

FIG. 1L shows the diesel hydrotreating plant 500 in the crude oil refinery facility. A second buffer fluid stream is flowed to the diesel hydrotreating plant 500 and is heated using a diesel stripper overheads stream in a second heat exchanger with a thermal duty that can range between about 10 MW and 20 MW (for example, 15.6 MW). As well, a third buffer fluid stream is flowed to the diesel hydrotreating plant 500 and can be heated using a diesel stripper bottoms stream in a third heat exchanger with a thermal duty that can range between about 15 MW and 25 MW (for example, 19.1 MW). The buffer fluid absorbs heat that would have otherwise been discharged to the environment. The diesel stripper overheads and the diesel stripper bottoms streams are returned to the diesel hydrotreating plant 500 for further processing. The first exchanger, the second exchanger and the third exchanger are coupled in parallel with one another relative to the flow of the buffer fluid.

The heated first, the heated second and the heated third buffer fluid streams are combined into a combined heated buffer fluid and directed to a collection header (or in some embodiments, a heated or insulated buffer fluid tank or storage unit that can hold heated collected buffer fluid for a period before use). The combined heated buffer fluid can then be flowed to either the sour water stripper plant 510 or a benzene extraction unit 518.

Figure 1M:
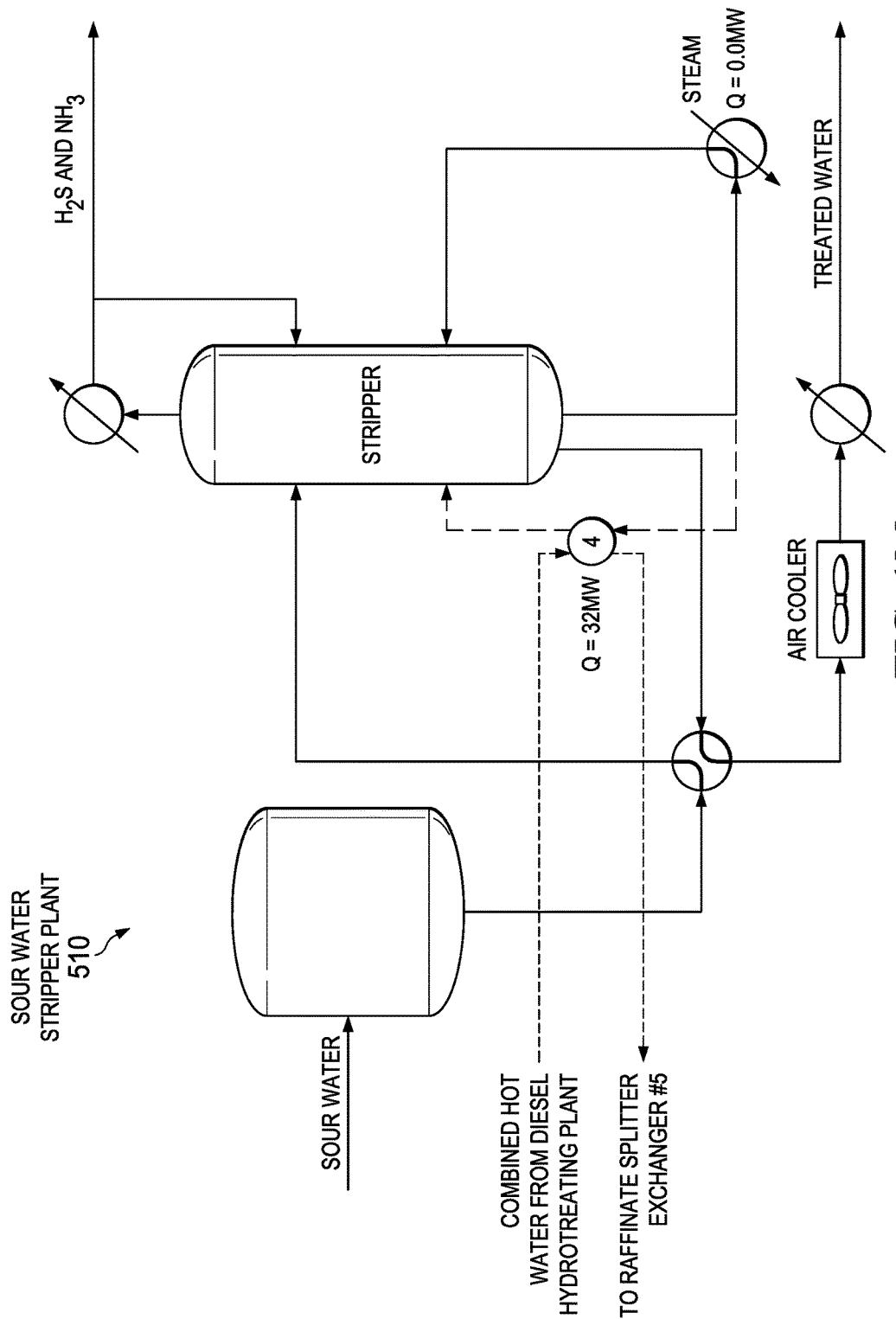

The combined heated buffer fluid can be flowed to the sour water stripper plant 510. FIG. 1M shows a sour water stripper plant 510 in the crude oil refining facility. The combined heated buffer fluid can heat a sour water stripper bottoms stream in a fourth heat exchanger with a thermal duty that can range between about 25 MW and 35 MW (for example, 32 MW) (FIG. 1M). The fourth heat exchanger is coupled to, in series with and is downstream of the set of first, second, and third heat exchangers relative to the flow of the buffer fluid. As shown in FIG. 1M, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Figure 1N:
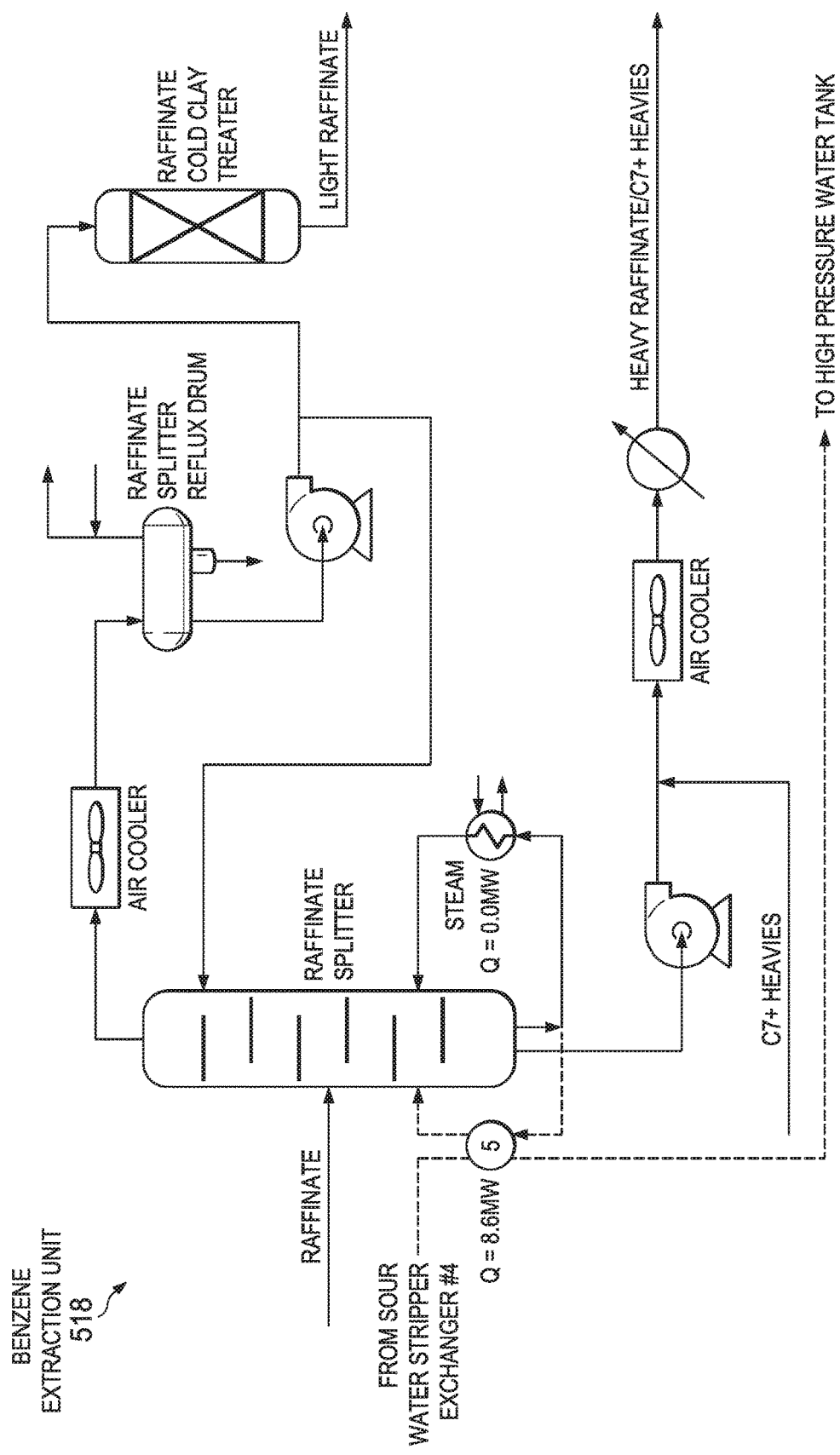

FIG. 1N shows the benzene extraction unit 518 in a crude oil refinery facility. The combined heated buffer fluid heats a raffinate column splitter bottoms stream in a fifth heat exchanger with a thermal duty that can range between about 5 MW and 15 MW (for example, 9 MW). The fifth heat exchanger is coupled to, in series with and is downstream of the set of first, second, and third heat exchangers relative to the flow of the heated buffer fluid. Also shown in FIG. 1N, the steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

The heated buffer fluid exiting the fifth heat exchanger in the benzene extraction unit 518 can be flowed to the collection header or the buffer fluid tank for reuse. In this manner, the fourth and the fifth heat exchangers are coupled to one another in series relative to the flow of the heated buffer fluid.

In some implementations, the heated buffer fluid can be flowed in series through the different plants. For example, the heated buffer fluid can be flowed first to the benzene extraction unit then to the sour water stripper plant. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly from the hydrogen plant and the diesel hydrotreating plant can result in decreasing or eliminating the heat energy to heat the streams in both the sour water stripper plant or the benzene extraction unit or combinations of them, such as by about 41 MW.

Configuration 3

FIGS. 1O-1T illustrate configurations and related scheme details for thermally integrating a sour water stripper plant and a gas separation plant in the crude oil refining facility with an aromatics complex in the crude oil refining facility. In some implementations, the aromatics complex sub-units include a xylene products separation plant. In certain schemes, a process stream (for example, a stream from one aromatics complex sub-units or other process streams) can be used to directly heat another process stream (for example, a sour water stripper plant stream or other process stream). In certain configurations, heat exchange between process streams can be implemented using an intermediate buffer fluid, for example, water, oil, or other buffer fluid.

The thermal integration described in these configurations and illustrated in FIGS. 1O-1T can reduce the crude oil refining facility's energy consumption (for example, heating and cooling utilities). For example, a reduction in energy consumption by about 46 MW can translate to at least about 7% of the energy consumption in the crude oil refining facility.

Configuration 3—Scheme A

In some implementations, the streams in the sour water stripper plant and the gas separation plant can be directly heated using one or more streams in the aromatics plant. The streams in the aromatics plant can include a raffinate column overhead stream in the aromatics complex xylene products separation unit. In some implementations, multiple first streams in multiple first plants can be directly heated using a second stream in a second plant. In some implementations, the multiple first plants include a sour water stripper plant and a gas separation plant; the multiple first streams include a sour water stripper bottoms, a de-ethanizer bottoms, and a C3/C4 bottoms streams; the second plant includes an aromatics complex xylene products separation unit; and the second stream includes a raffinate column overheads stream.

Figure 1O:
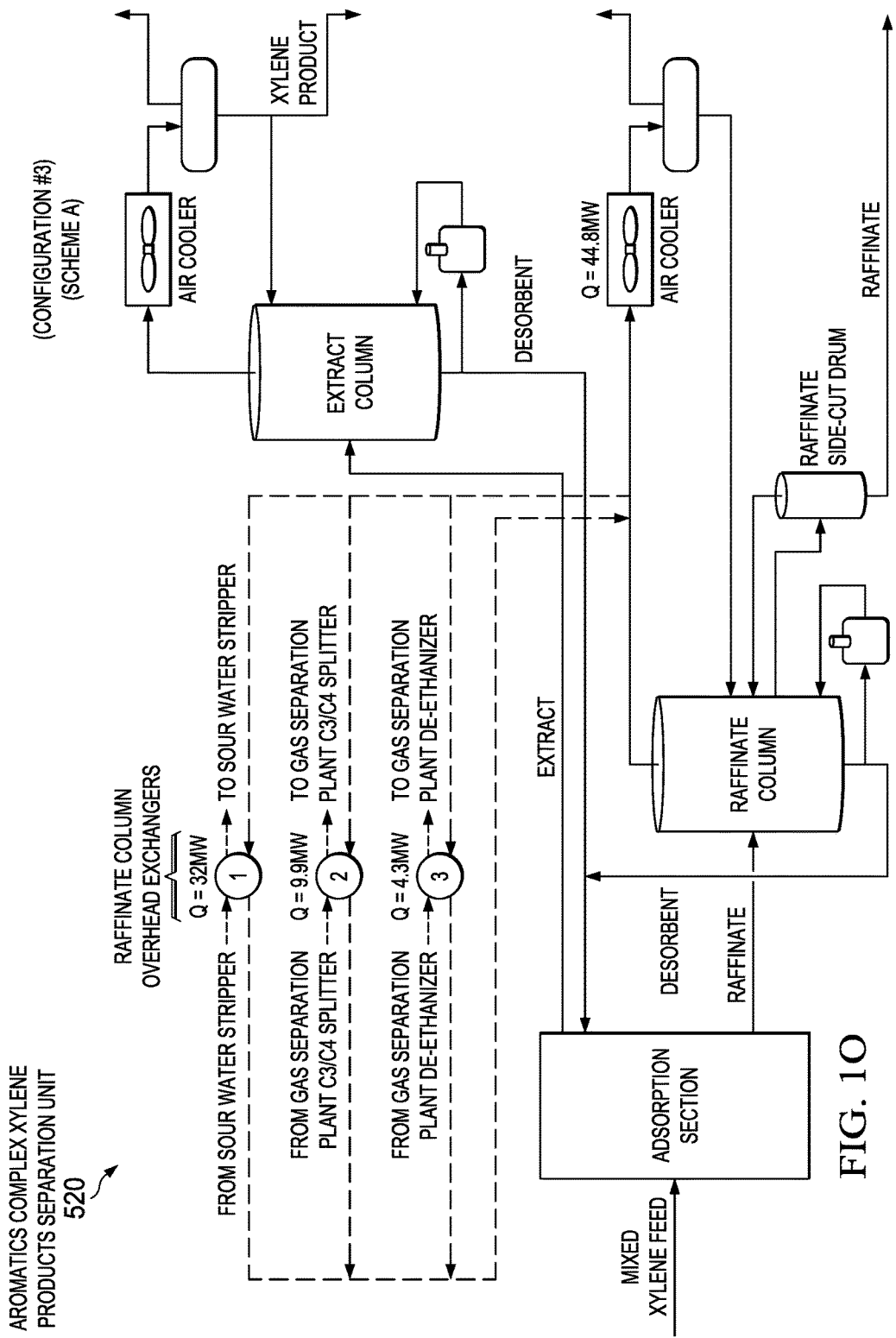
FIGS. 1O-1T illustrate a third set of configurations and related scheme details for thermally integrating a sour water stripper plant and a gas separation plant in the crude oil refining facility with an aromatics plant in the crude oil refining facility.

FIG. 1A shows an aromatics complex xylene products separation unit 520. The raffinate overheads column stream can be flowed in the plant as a single stream and split into multiple streams or it can be flowed into the plant as multiple streams to facilitate heat recovery. The first raffinate column overheads stream can directly heat a sour water stripper bottom stream in a first heat exchanger with a thermal duty that can range between about 25 MW and 35 MW (for example, 32 MW). A second raffinate column overheads stream can directly heat a C3/C4 splitter bottom stream in a second heat exchanger with a thermal duty that can range between about 5 MW and 15 MW (for example, 9.9 MW). A third raffinate column overheads stream can directly heat a de-ethanizer bottom stream in a third heat exchanger with a thermal duty that can range between about 1 MW and 10 MW (for example, 4.3 MW) (FIG. 1O and FIG. 1Q). In this manner, the first heat exchanger, the second heat exchanger and the third heat exchanger are coupled to each other in parallel relative to the flow of the raffinate column overheads stream. For each stream, the transfer of heat directly to another process stream captures heat that would have otherwise been discharged to the environment. The raffinate column overheads streams are recombined and returned to the xylene products separation unit 520 for further processing.

Figure 1P:
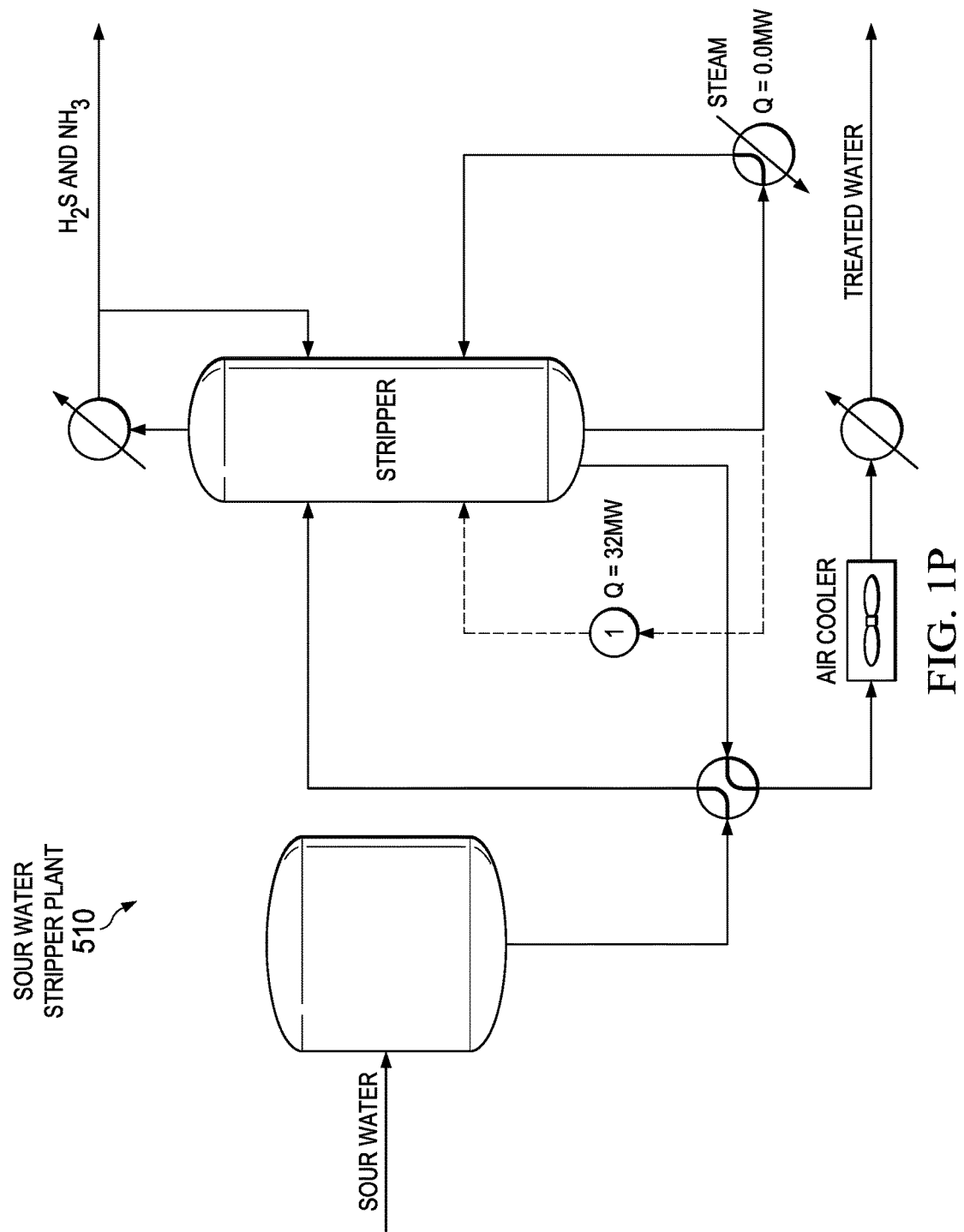
Figure 1Q:
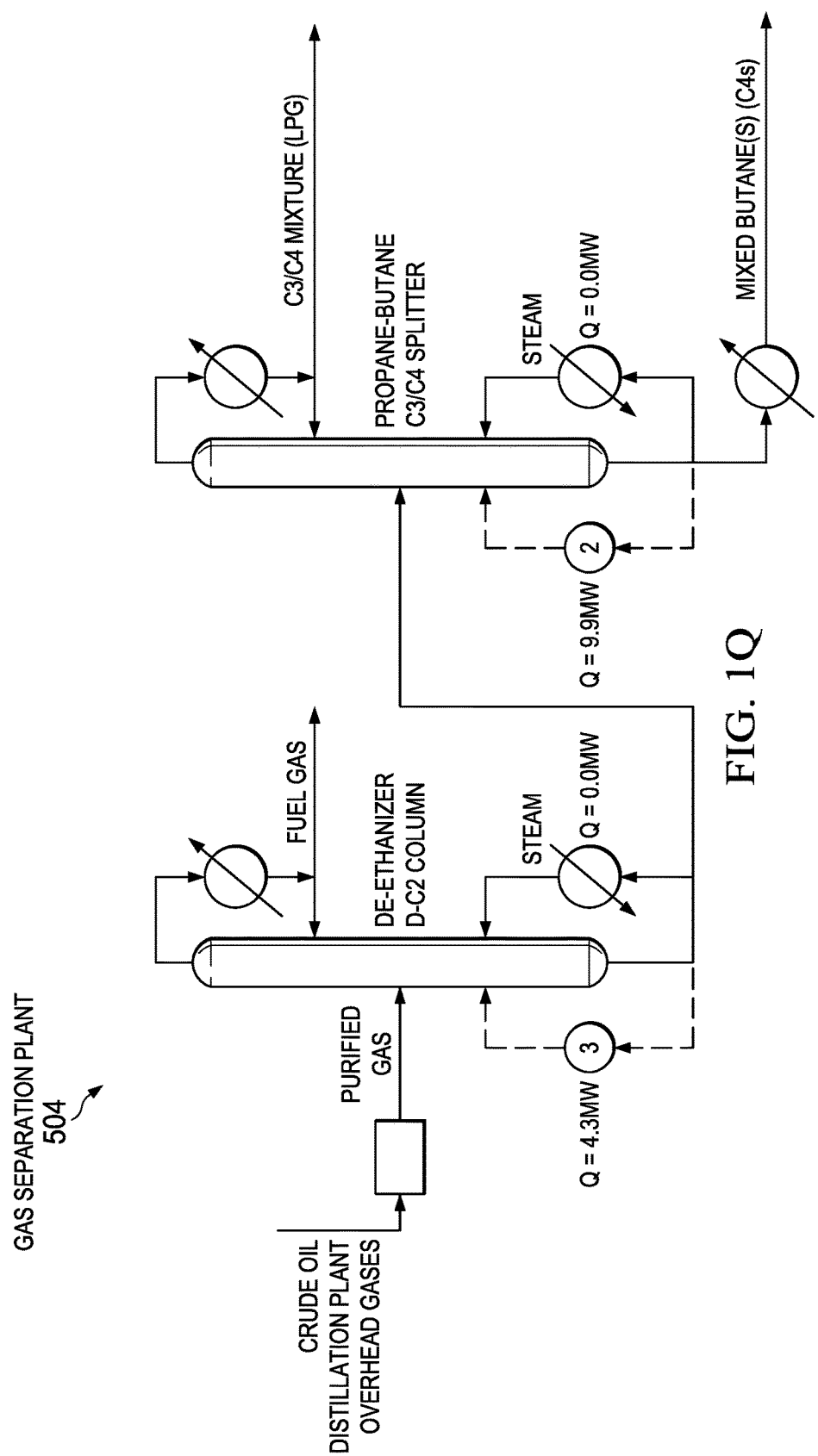

FIG. 1P shows the sour water stripper plant 510 in the crude oil refinery facility. The heated sour water stripper bottoms stream can then be flowed to the sour water stripper plant 510. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1Q shows the gas separation plant 504 in the crude oil refinery facility. The heated C3/C4 splitter bottoms stream can then be flowed to the gas separation plant 504. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

The heated de-ethanizer bottoms stream can be flowed to the gas separation plant 504. As shown in FIG. 1Q, the steam heat input for the de-ethanizer can be 0 MW because the alternative flow path disclosed in this configuration may satisfy the entire heat load for the operation of the column. In an alternative embodiment, the steam heat input for the de-ethanizer can be reduced because the alternative flow path disclosed in this configuration may partially satisfy the heat load for the operation of the column.

Such recovery and reuse of waste heat directly from the aromatics complex xylene products separation unit can result in decreasing or eliminating the heat energy to heat the sour water stripper plant or the gas separation plant or a combinations of them, such as by about 46 MW.

Configuration 3—Scheme B

In some implementations, the multiple streams in the crude oil refining facility such as those present in the sour water stripper plant and the gas separation plant can be indirectly heated using the one or more streams in the aromatics complex as heat energy sources. In some implementations, the multiple first streams in multiple first plants in the crude oil refining facility can be indirectly heated using a second stream in a second plant in the aromatics complex. In some implementations, the multiple first plants include a sour water stripper plant and a gas separation plant; the multiple first streams include a sour water stripper bottoms, a de-ethanizer, and a C3/C4 splitter bottoms streams; the second plant includes a aromatics complex xylene separation unit; and the second stream includes a raffinate column overheads stream.

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene products separation unit 520. The buffer fluid can be flowed into the plant as a single stream and split into multiple streams or it can be flowed into the plant as multiple streams.

Figure 1R:
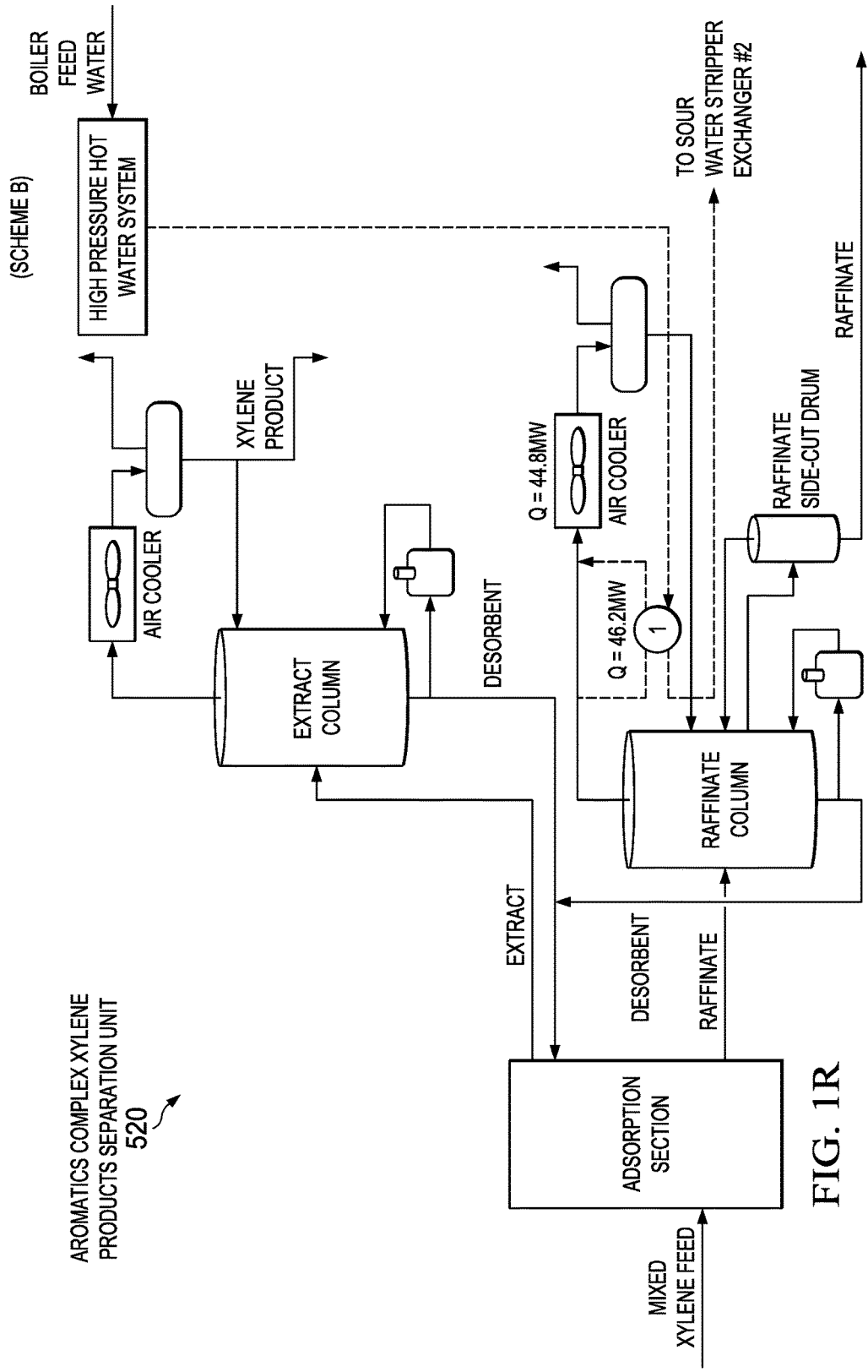

FIG. 1R shows an aromatics complex xylene products separation unit 520. A buffer fluid from a buffer fluid tank (for example, boiler feed water from a high pressure hot water system) can be flowed to the aromatics complex xylene products separation plant 520. The raffinate column overheads stream can be used to heat the buffer fluid in a first heat exchanger with a thermal duty that can range between about 40 MW and 50 MW (for example, 46.2 MW). The buffer fluid absorbs heat that would have otherwise been discharged to the environment. The raffinate column overheads stream is returned to the xylene products separation unit 520 for further processing.

The heated buffer fluid is directed to a collection header (or in some embodiments, a heated or insulated buffer fluid tank or storage unit that can hold heated collected buffer fluid for a period before use) and then can be flowed to either the sour water stripper plant 510 or a gas separation plant 504.

Figure 1S:
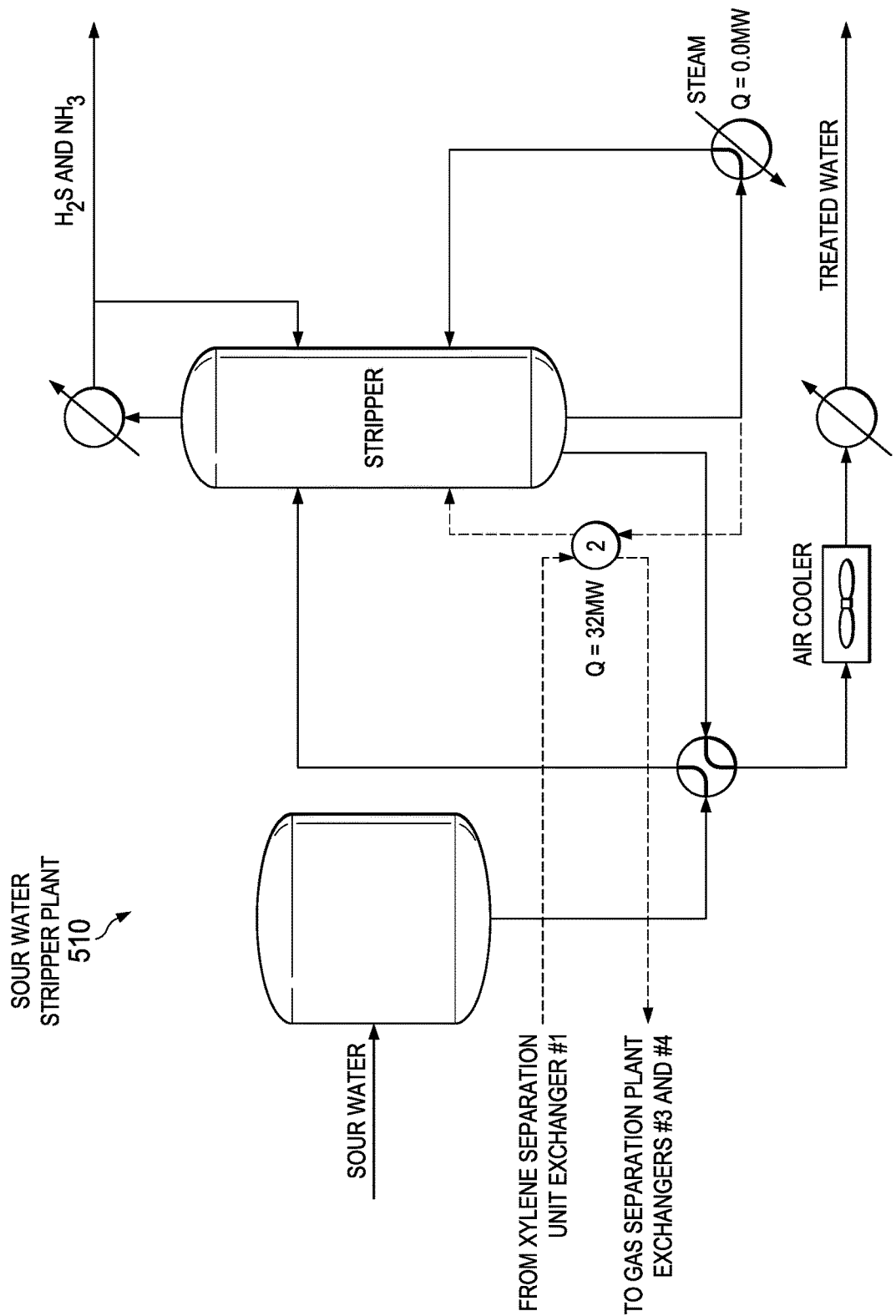

FIG. 1S shows the sour water stripper plant 510 in a crude oil refinery facility. As shown in FIG. 15, the heated buffer fluid can be flowed to the sour water stripper plant 510. A sour water stripper bottoms stream can be heated using the heated buffer fluid in a second heat exchanger with a thermal duty that can range between about 25 MW and 35 MW (for example, 32 MW). In this manner, the second heat exchanger is coupled to, is downstream of and is in series with the first heat exchanger relative to the flow of the buffer fluid. As shown in FIG. 1S, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Figure 1T:
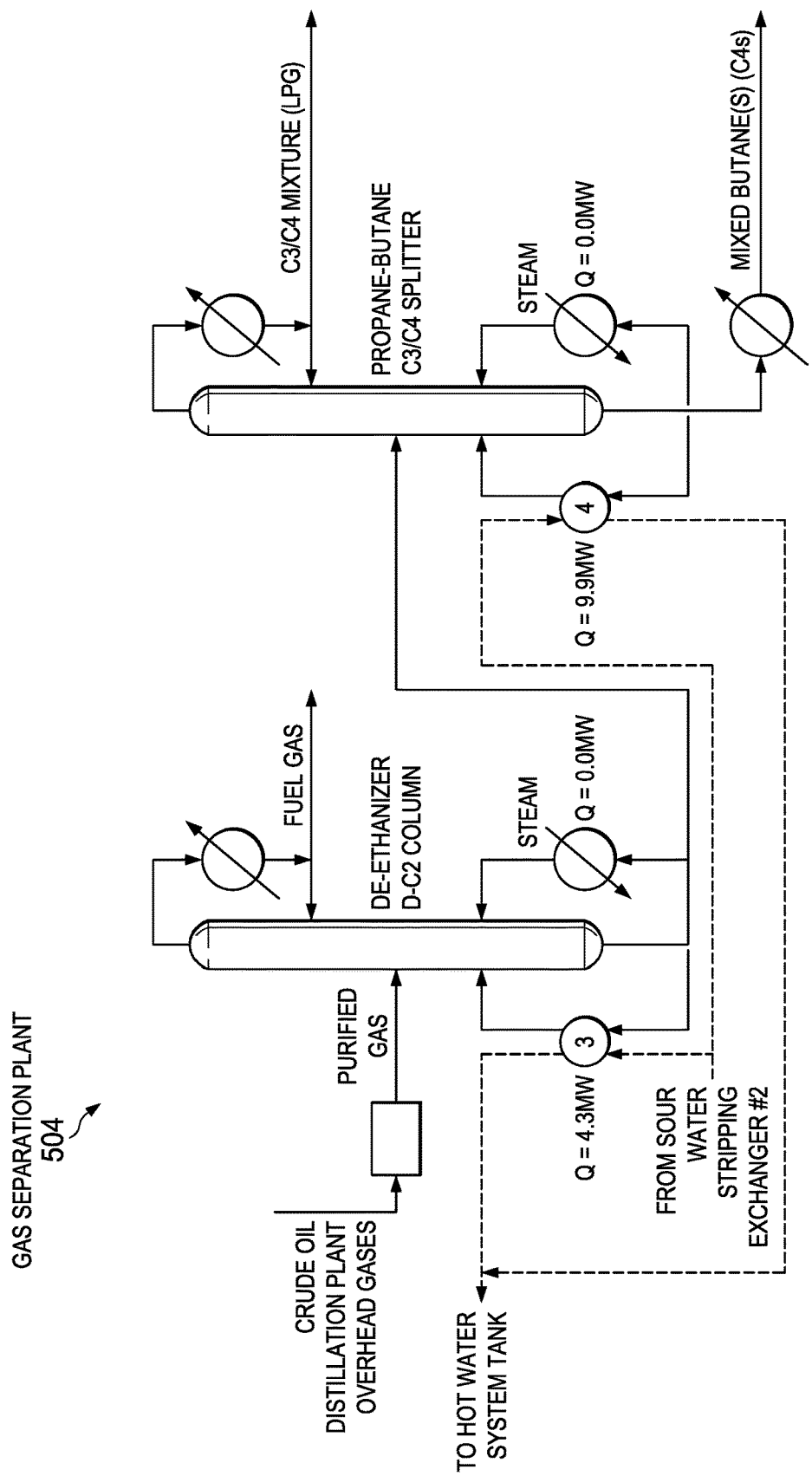

FIG. 1T shows the gas separation plant 504 in a crude oil refinery facility. The heated buffer fluid exiting the second heat exchanger can be flowed to the gas separation plant 504 and, as shown in FIG. 1T, split into a first heated buffer fluid stream and a second heated buffer fluid stream. A de-ethanizer bottoms stream can be heated using the first heated buffer fluid branch in a third heat exchanger with a thermal duty that can range between about 1 MW and 10 MW (for example, 4.3 MW). The third heat exchanger is coupled to, is downstream of and is in series with the first heat exchanger relative to the buffer fluid flow. As shown in FIG. 1T, the steam heat input for the de-ethanizer can be 0 MW because the alternative flow path disclosed in this configuration may satisfy the entire heat load for the operation of the column. In an alternative embodiment, the steam heat input for the de-ethanizer can be reduced because the alternative flow path disclosed in this configuration may partially satisfy the heat load for the operation of the column.

As shown in FIG. 1T, the second heated buffer fluid stream heats a C3/C4 splitter bottoms stream in a fourth heat exchanger with a thermal duty that can range between about 5 MW and 15 MW (for example, 9.9 MW). The fourth heat exchanger is coupled to, are downstream of and in series with the first heat exchanger relative to the buffer fluid flow. In this manner, the third heat exchanger and the fourth heat exchanger can be coupled to and in parallel to one another relative to the flow of heated buffer fluid. As shown in FIG. 1T, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

The first heated buffer fluid stream exiting the third heat exchanger and the second heated buffer fluid stream passing from the fourth heat exchanger may recombine into a combined heated buffer fluid and flowed to the collection header or the buffer fluid tank for reuse. In this manner, the second and the set of the third and fourth heat exchangers in parallel with one another are in series with each other relative to the flow of the heated buffer fluid.

In some implementations, the heated buffer fluid can be flowed in series through the different plants. For example, the heated buffer fluid can be flowed first to the gas separation plant then to the sour water stripper plant. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly from the aromatics complex can result in decreasing or eliminating the heat energy to heat the sour water stripper or the gas separation plant or combinations of them, such as by about 46 MW.

Configuration 4

FIGS. 1U-1Z illustrate configurations and related scheme details for thermally integrating refining sub-units of an aromatics plant in the crude oil refining facility and other plants in the crude oil refining facility. In some implementations, the aromatics plant sub-units can include an aromatics complex xylene products separation unit. The other plants in the crude oil refining facility can include a sour water stripper plant and a sulfur recovery plant. In certain schemes, a process stream (for example, a stream from one refining sub-unit of an aromatics plant or other process streams) can be used to directly heat another process stream (for example, a sulfur recovery plant stream or other process stream). In certain configurations, heat exchange between process streams can be implemented using an intermediate buffer fluid, for example, water, oil, or other buffer fluid.

The thermal integration described in these configurations and illustrated in FIGS. 1U-1Z can reduce the crude oil refining facility's energy consumption (for example, heating and cooling utilities). For example, a reduction in energy consumption by about 53 MW can translate to at least about 8% of the energy consumption in the crude oil refining facility.

Configuration 4—Scheme A

The multiple streams in sub-units of the crude oil refining facility can be directly heated using the one or more streams from the aromatics complex. In some implementations, the multiple streams in the sour water stripper plant and the sulfur recovery plant can be directly heated using one or more streams in the aromatics complex xylene products separation unit. In some implementations, multiple first streams in multiple first plants can be directly heated using a second stream in a second plant. In some implementations, the first plants include a sour water stripper plant and a sulfur recovery plant; the first streams include a sour water stripper bottoms and an amine regenerator bottoms streams; the second plant includes an aromatics complex xylene products separation unit; and the second stream includes a raffinate column overheads stream.

Figure 1U:
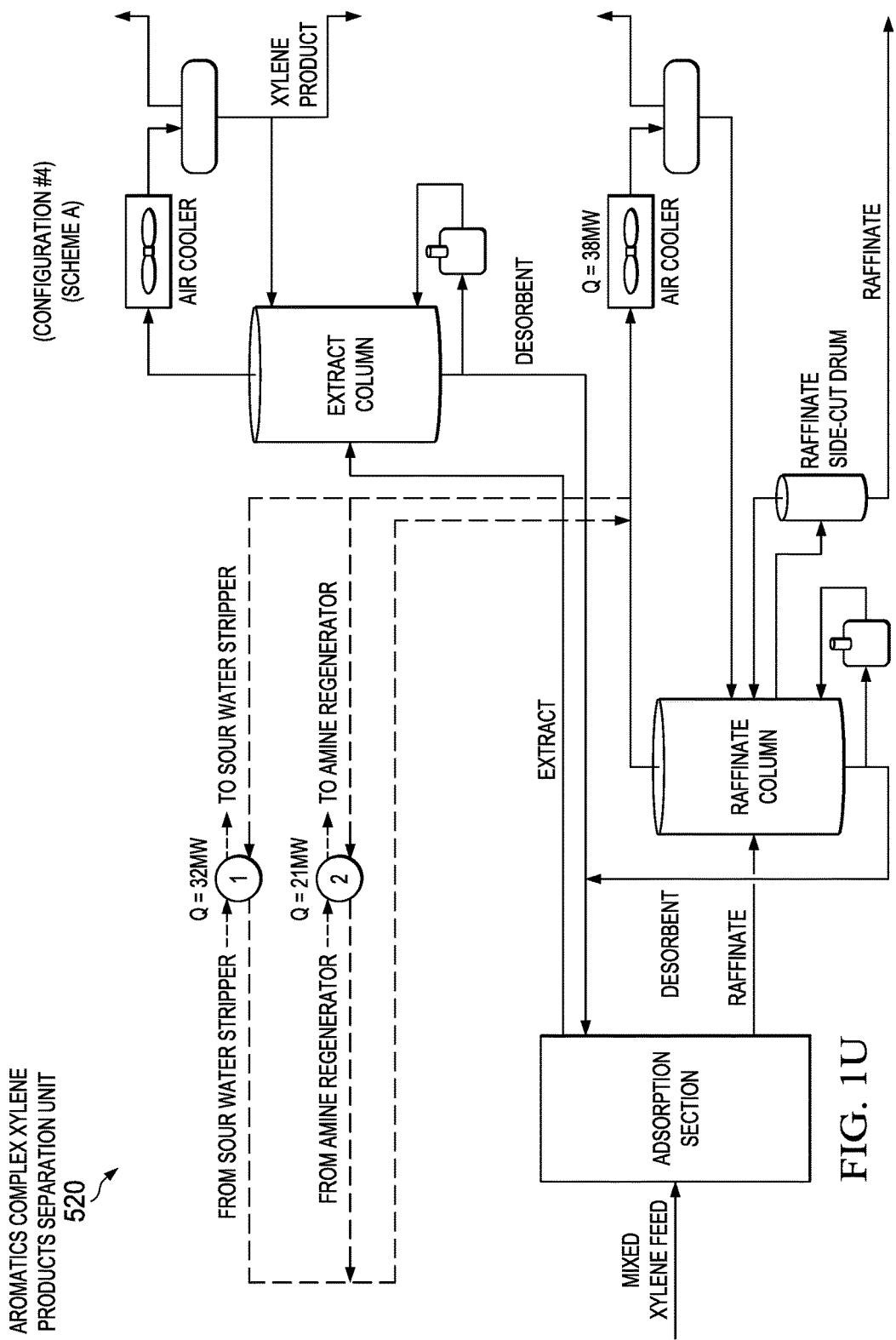
FIGS. 1U-1Z illustrate a fourth set configurations and related scheme details for thermally integrating a sulfur recovery plant and a sour water stripper plant in the crude oil refining facility with an aromatics plant in the crude oil refining facility.

FIG. 1U shows the aromatics complex xylene products separation unit 520 in the crude oil refinery facility. The raffinate column overheads stream can be flowed in the plant as a single stream and split into multiple streams or it can be flowed into the plant as multiple streams to facilitate heat recovery. A first raffinate column overhead stream can directly heat a sour water stripper bottoms stream in a first heat exchanger with a thermal duty that can range between about 25 MW and 35 MW (for example, 32 MW). The second raffinate column overhead stream can directly heat a sulfur recovery plant amine regenerator bottom stream in a second heat exchanger with a thermal duty that can range between about 15 MW and 25 MW (for example, 21 MW). In this manner, the first heat exchanger and the second heat exchanger can be coupled to each other in parallel relative to the flow of raffinate column overheads stream. The transfer of heat directly to another process stream captures heat that would have otherwise been discharged to the environment. The raffinate column overheads streams are recombined and returned to the xylene products unit 520 for further processing.

Figure 1V:
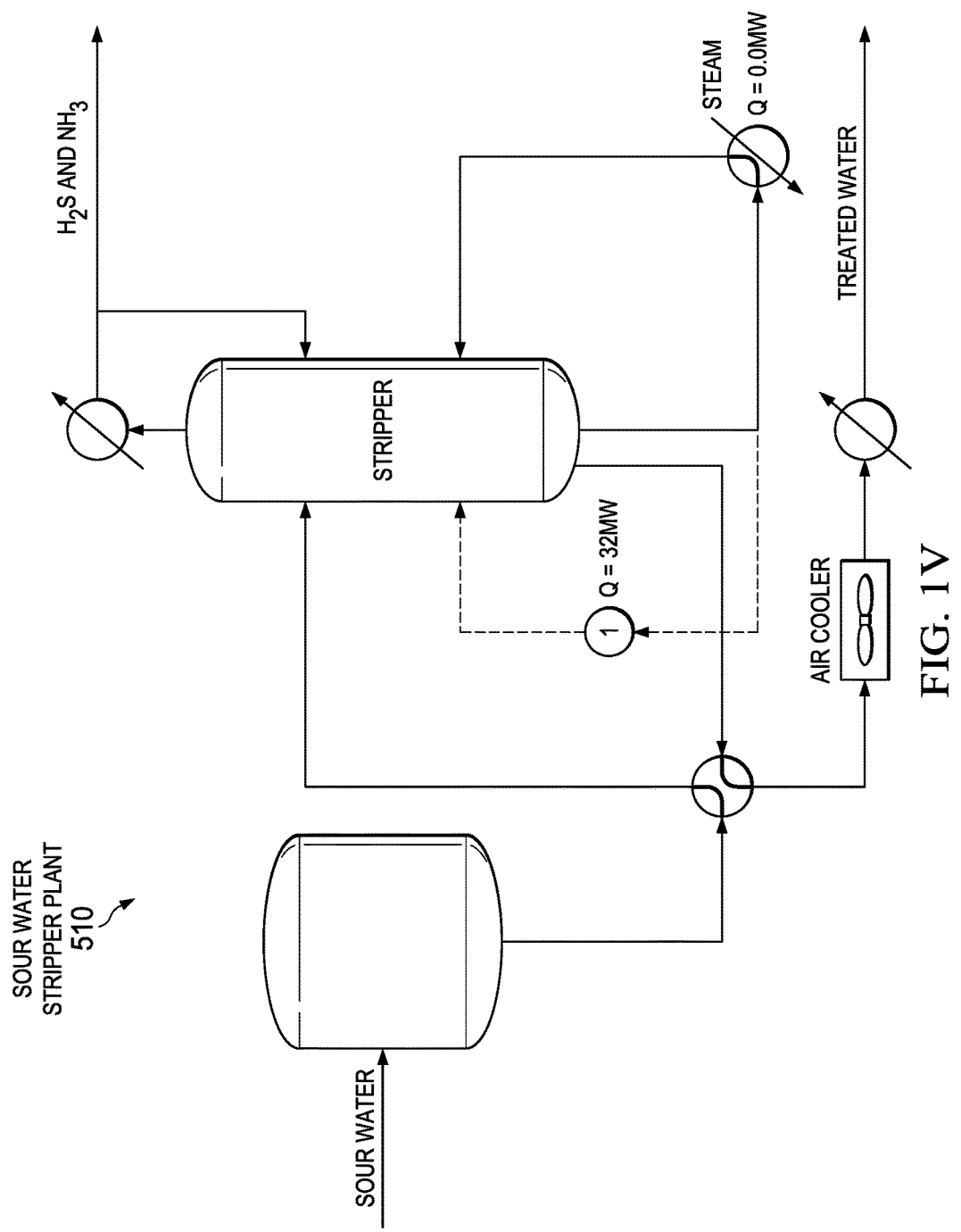

FIG. 1V shows the sour water stripper plant 510 in the crude oil refinery facility. The heated sour water stripper bottom stream can then be flowed to the sour water stripper plant 510. As shown in FIG. 1V, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Figure 1W:
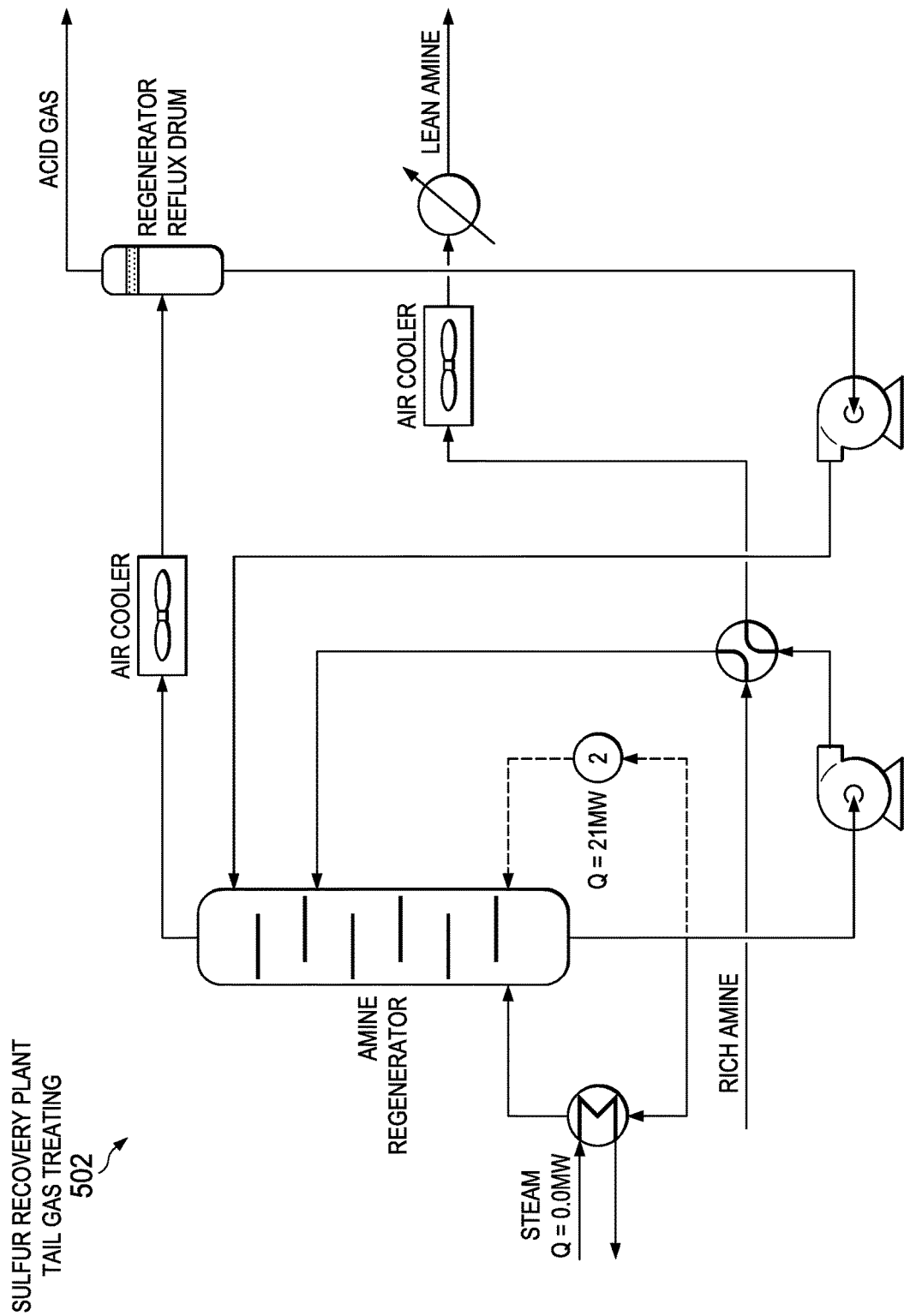

FIG. 1W shows the sulfur recovery plant 502 in the crude oil refinery facility. The heated sulfur recovery plant amine regenerator bottom stream can then be flowed to the sulfur recovery plant 502. As shown in FIG. 1W, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

Such recovery and reuse of waste heat directly from the aromatics complex can result in decreasing or eliminating the heat energy to heat the sour water stripper plant or the sulfur recovery plant or combinations of them, such as by about 53 MW.

Configuration 4—Scheme B

In some implementations, the multiple streams such as those in the sour water stripper plant and the sulfur recovery plant can be indirectly heated using a buffer fluid, for example, oil, water or other buffer fluid, using the one or more streams in the aromatics plant as heat energy sources. In some implementations, the multiple first streams in multiple first plants in the crude oil refining facility can be indirectly heated using a second stream in a second plant. In some implementations, the multiple first plants include a sulfur recovery plant and a sour water stripper plant; the multiple first streams include an amine regenerator bottoms and a sour water stripper bottoms streams; the second plant include an aromatics complex xylene products separation plant; and the second stream includes a raffinate column overheads stream.

Indirectly heating the streams can include heating the streams through a buffer fluid, for example, oil, water, or other buffer fluid. A buffer fluid (for example, high pressure water) from a buffer fluid tank (for example, hot water tank) is flowed to the aromatics complex xylene products separation unit 520. The buffer fluid can be flowed into each plant as a single stream and split into multiple streams or it can be flowed into a plant as multiple streams.

Figure 1X:
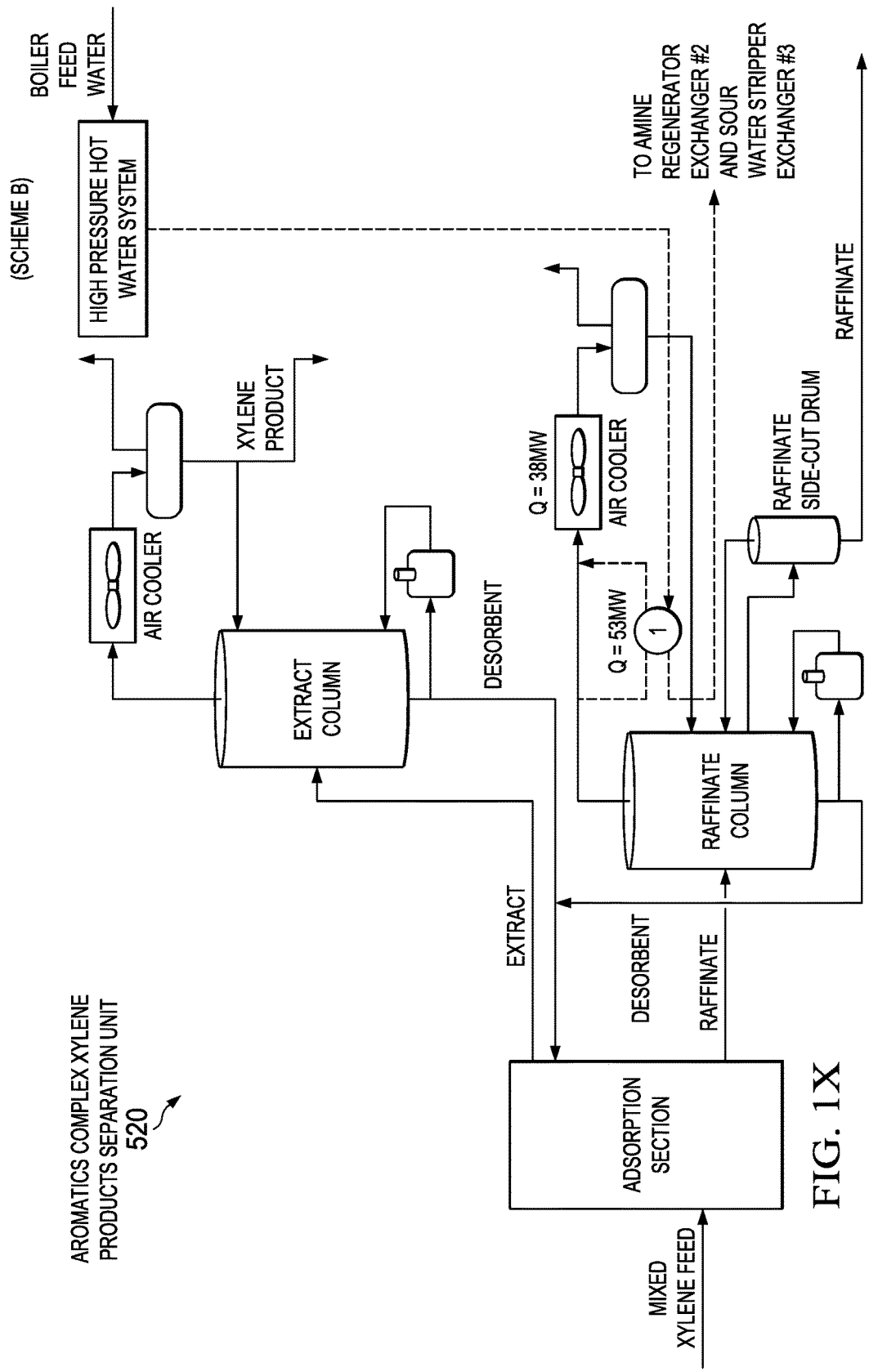

FIG. 1X shows the aromatics complex xylene products separation unit 520 in a crude oil refinery facility. A buffer fluid from a buffer fluid tank (for example, boiler feed water from a high pressure hot water system) can be flowed to an aromatics complex xylene products separation unit 520. The raffinate column overheads stream can be used to heat the buffer fluid in a first heat exchanger with a thermal duty that can range between about 50 MW and 60 MW (for example, 53 MW). The buffer fluid absorbs heat that would have otherwise been discharged to the environment. The raffinate column overhead stream is returned to the xylene products separation unit 520 for further processing.

The heated buffer fluid is directed to a collection header (or in some embodiments, a heated or insulated buffer fluid tank or storage unit that can hold heated collected buffer fluid for a period before use) and then can be flowed to either the sulfur recovery plant 502 and the sour water stripper 510, or both. The heated buffer fluid is split into a first heated buffer fluid stream and a second heated buffer fluid stream.

Figure 1Y:
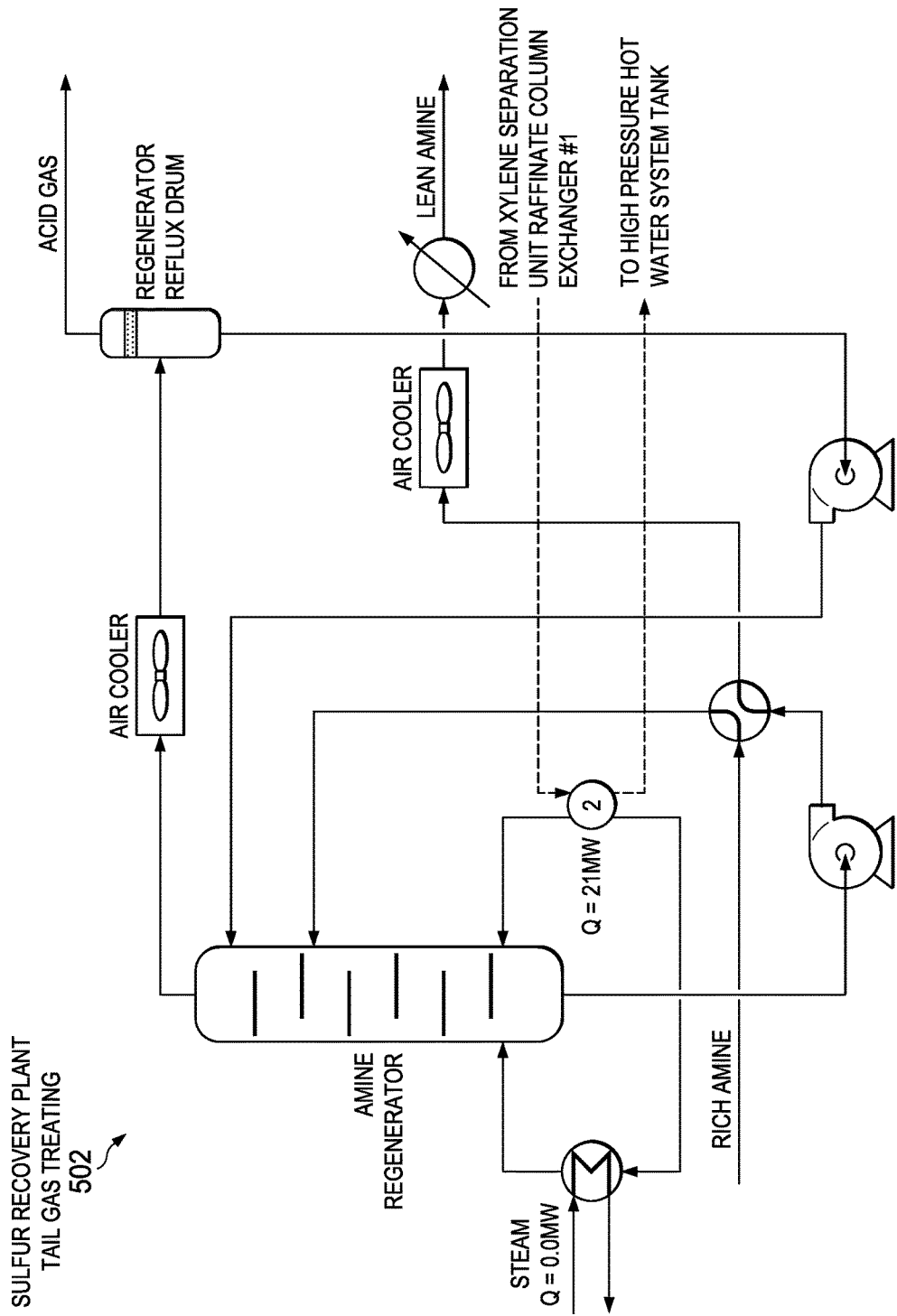

FIG. 1Y shows the sulfur recovery plant 502 in a crude oil refinery facility. The first heated buffer fluid stream can be flowed to the sulfur recovery plant 502. An amine regenerator bottoms stream can be heated using the first heated buffer fluid stream in a second heat exchanger with a thermal duty that can range between about 15 MW and 25 MW (for example, 21 MW). In this manner, the second heat exchanger is coupled to, in series with and is downstream of the first heat exchanger relative to the flow of buffer fluid. As shown in FIG. 1Y, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

Figure 1Z:
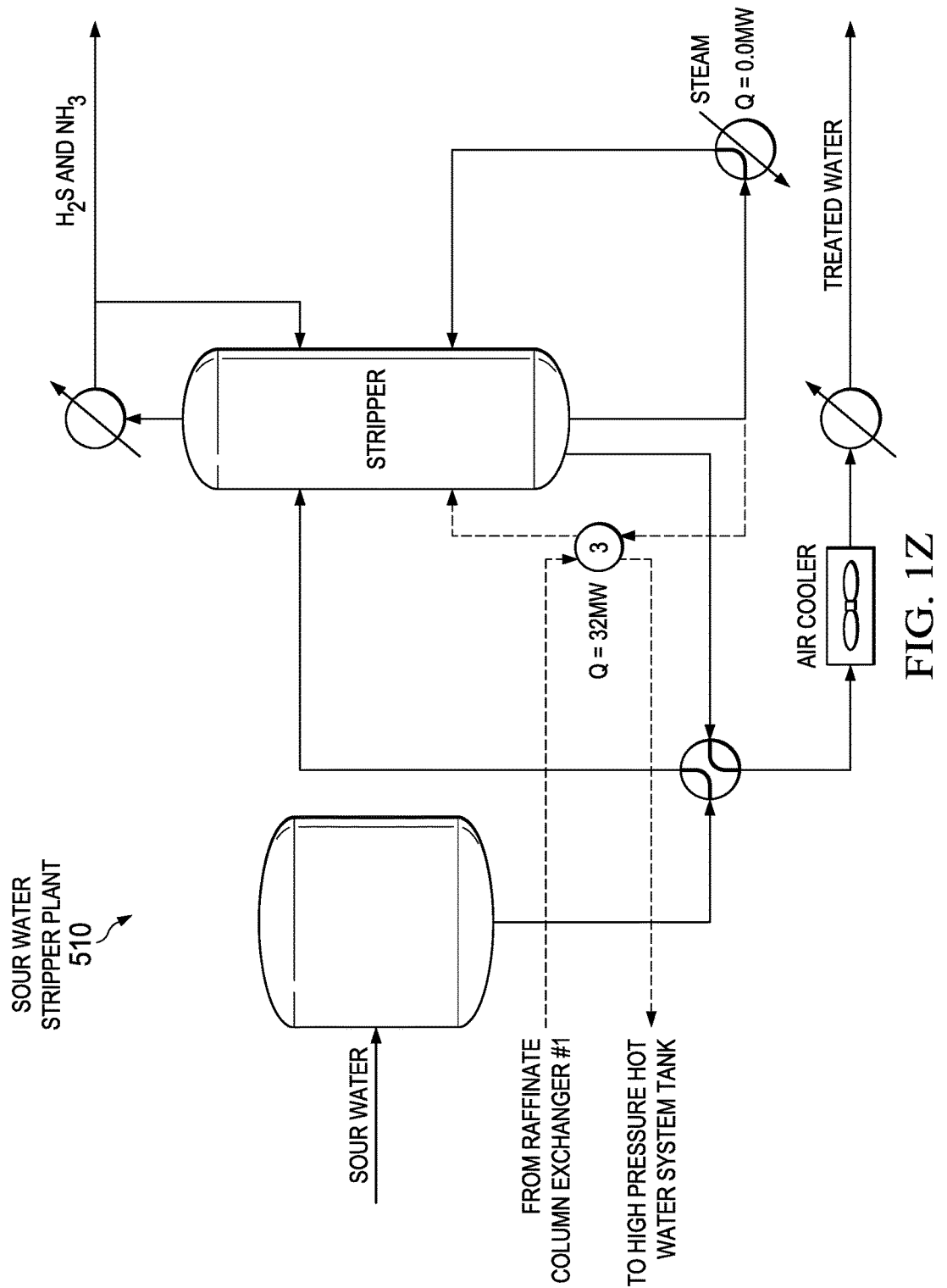
Figure 1A:
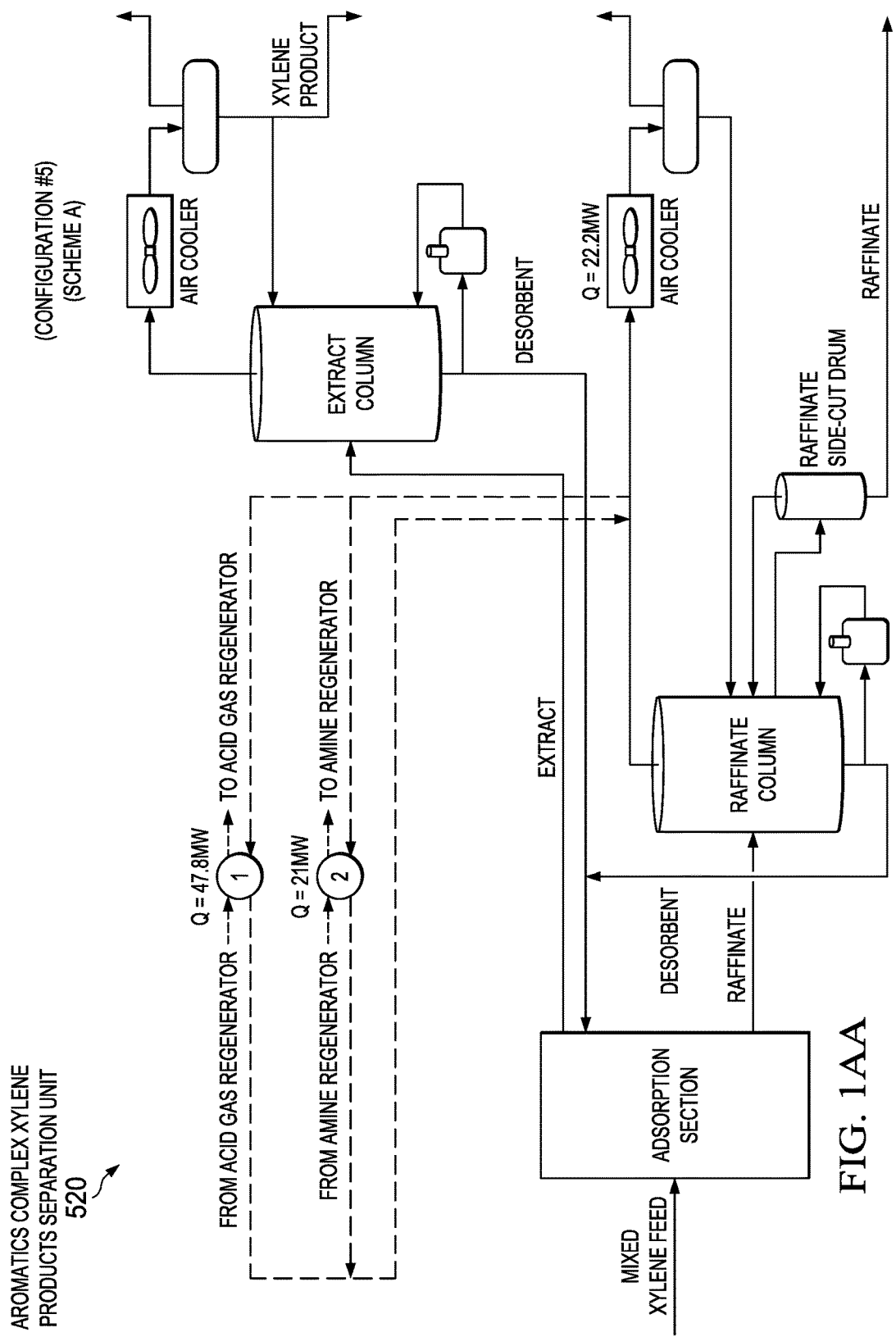
Figure 1A:
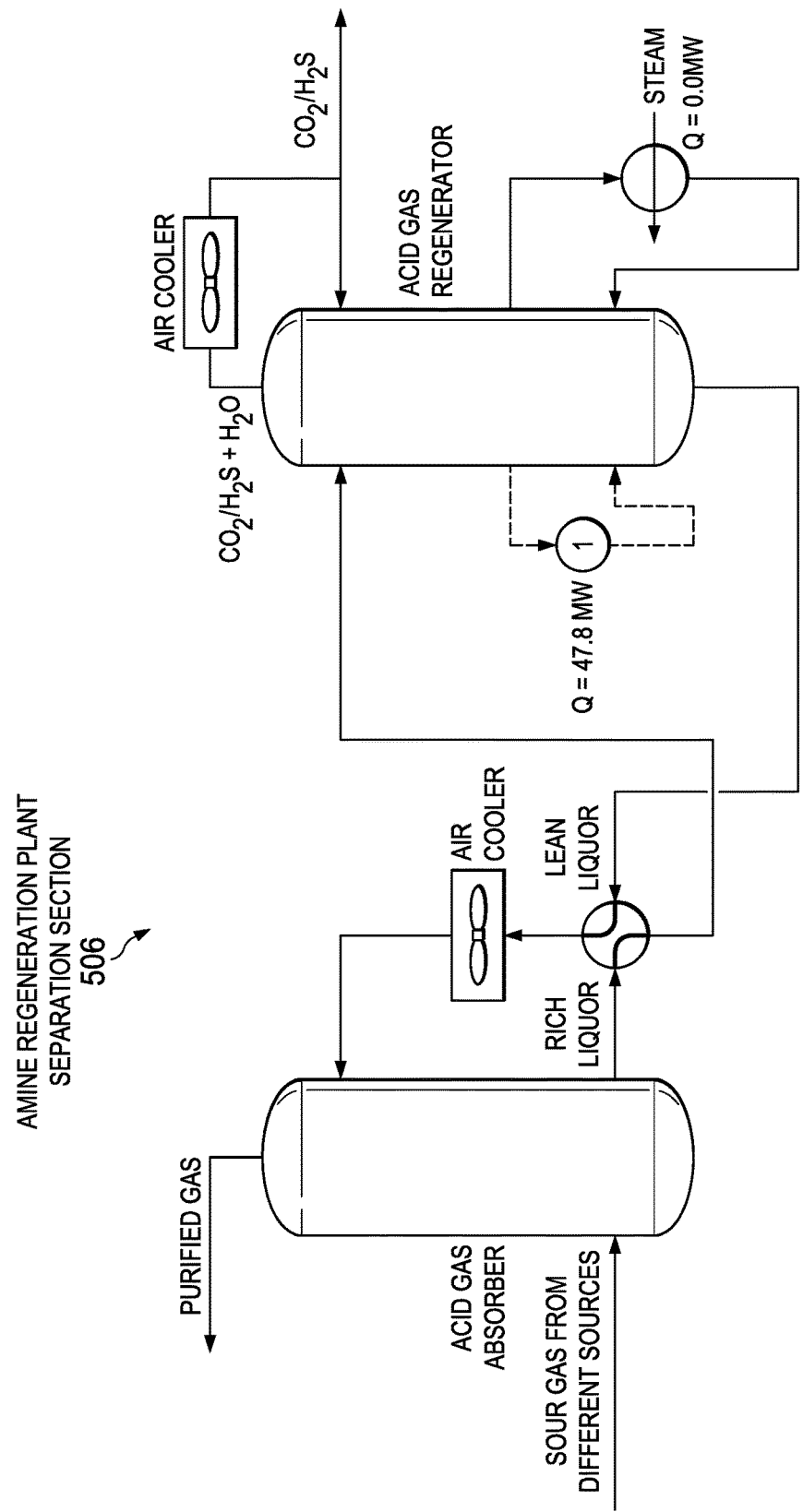
Figure 1A:
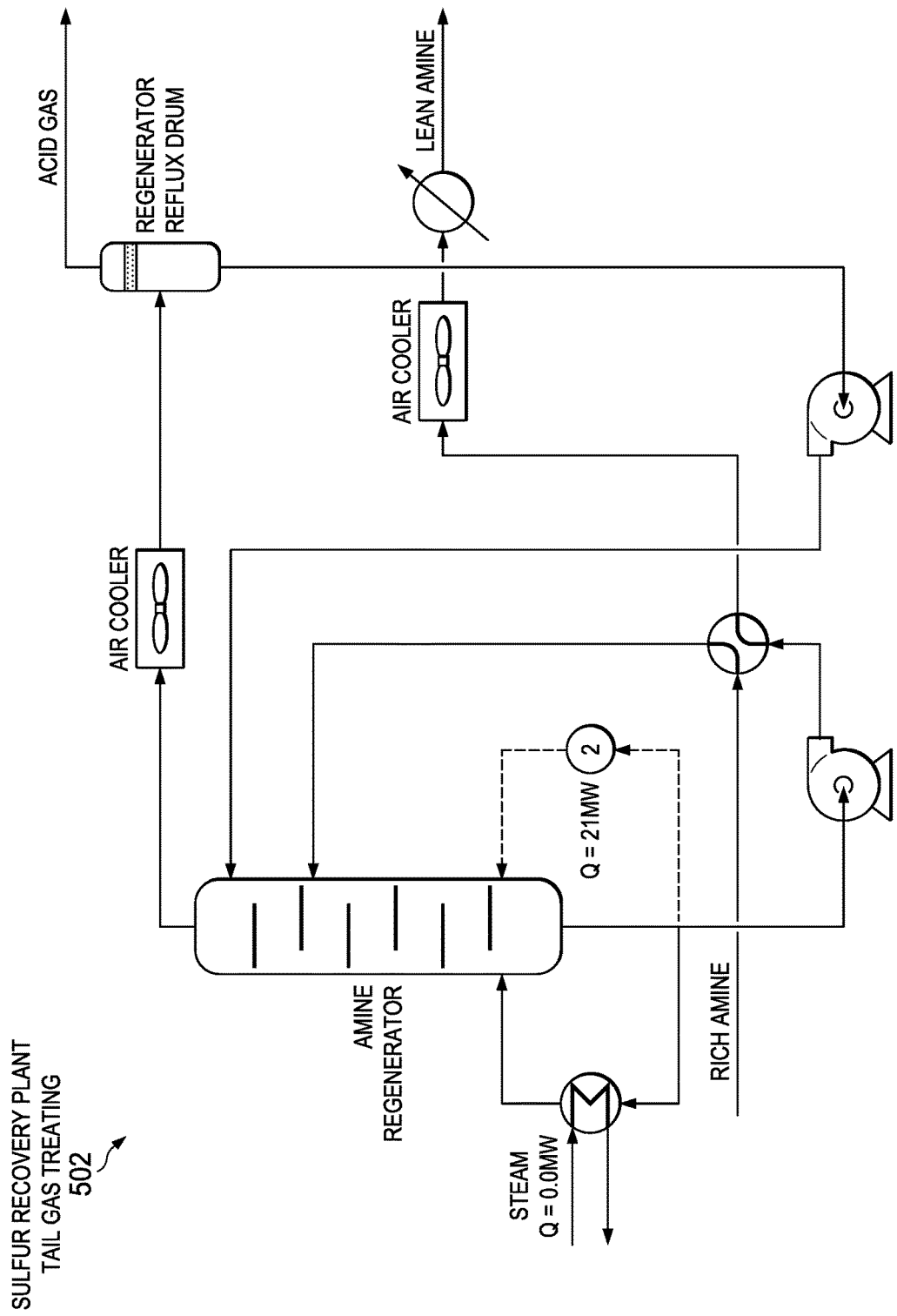
Figure 1A:
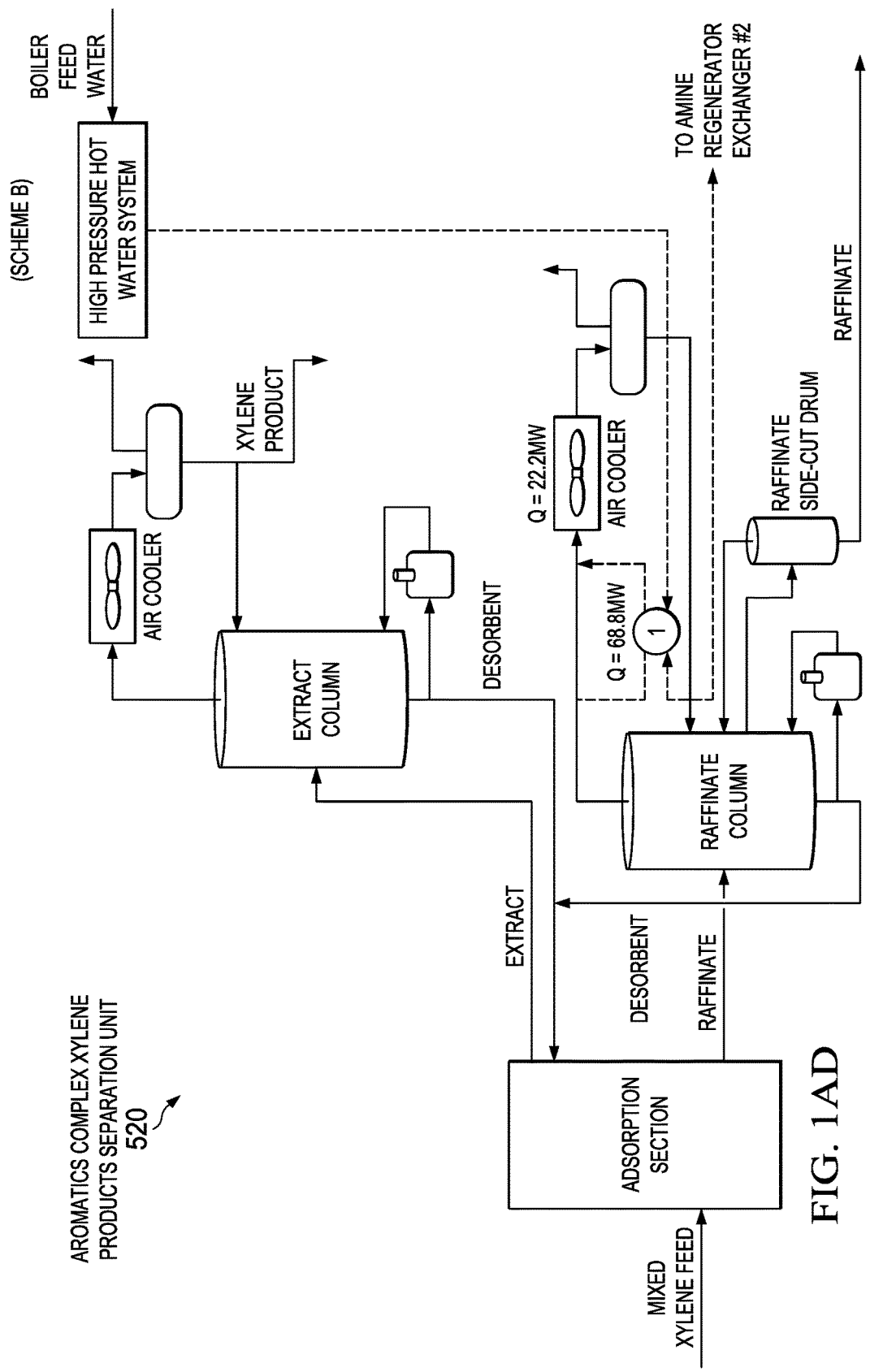
Figure 1A:
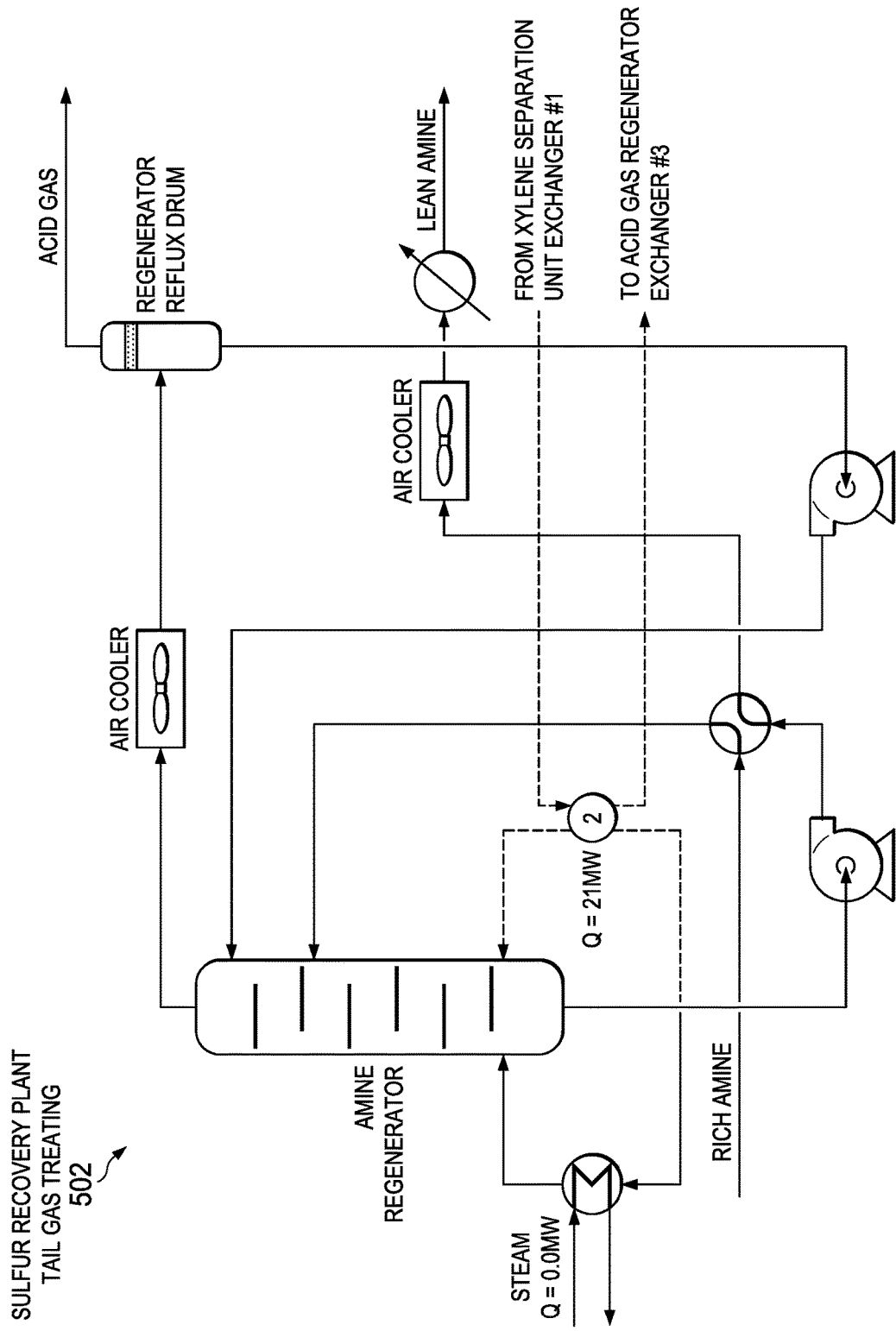
Figure 1A:
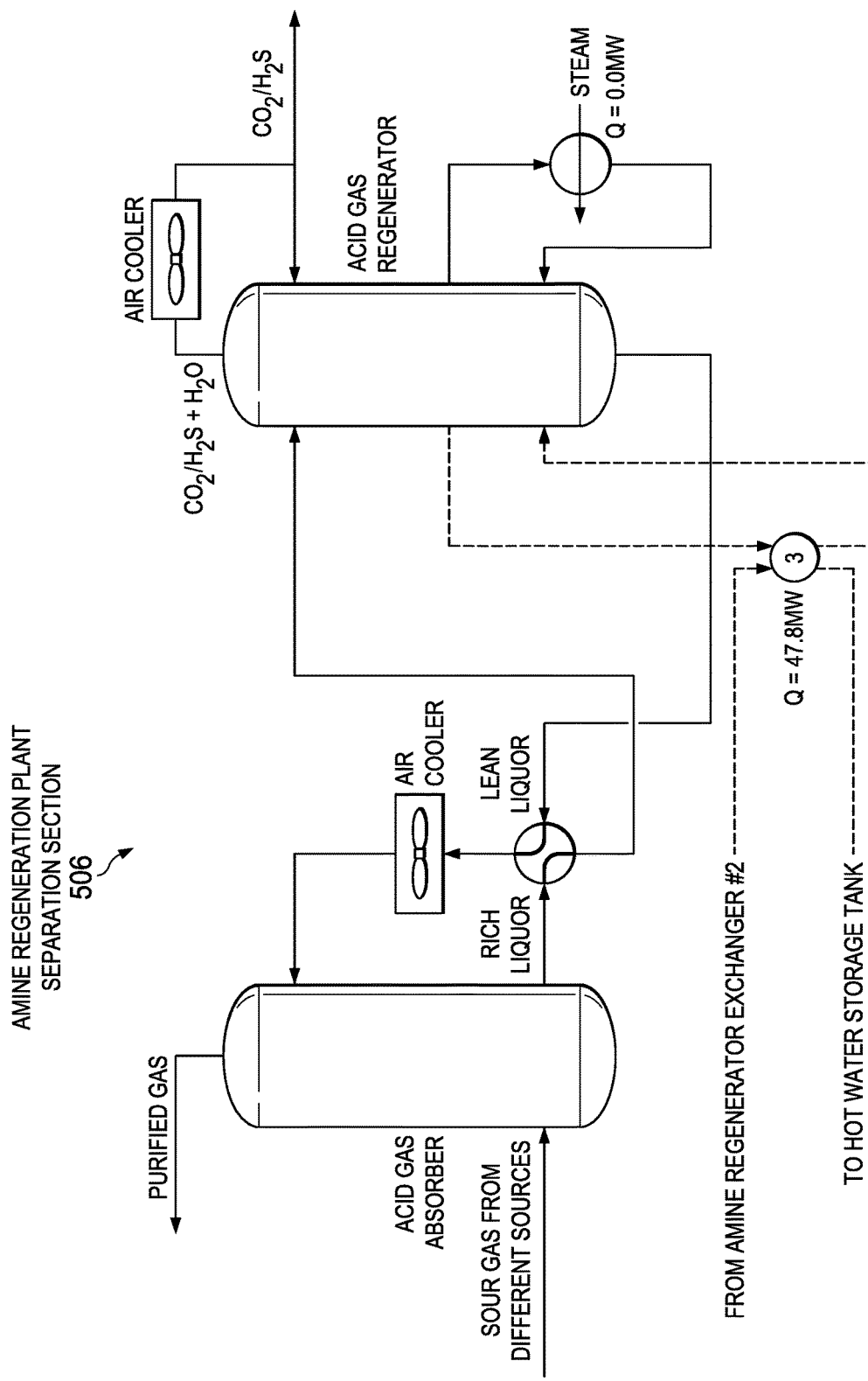
Figure 1A:
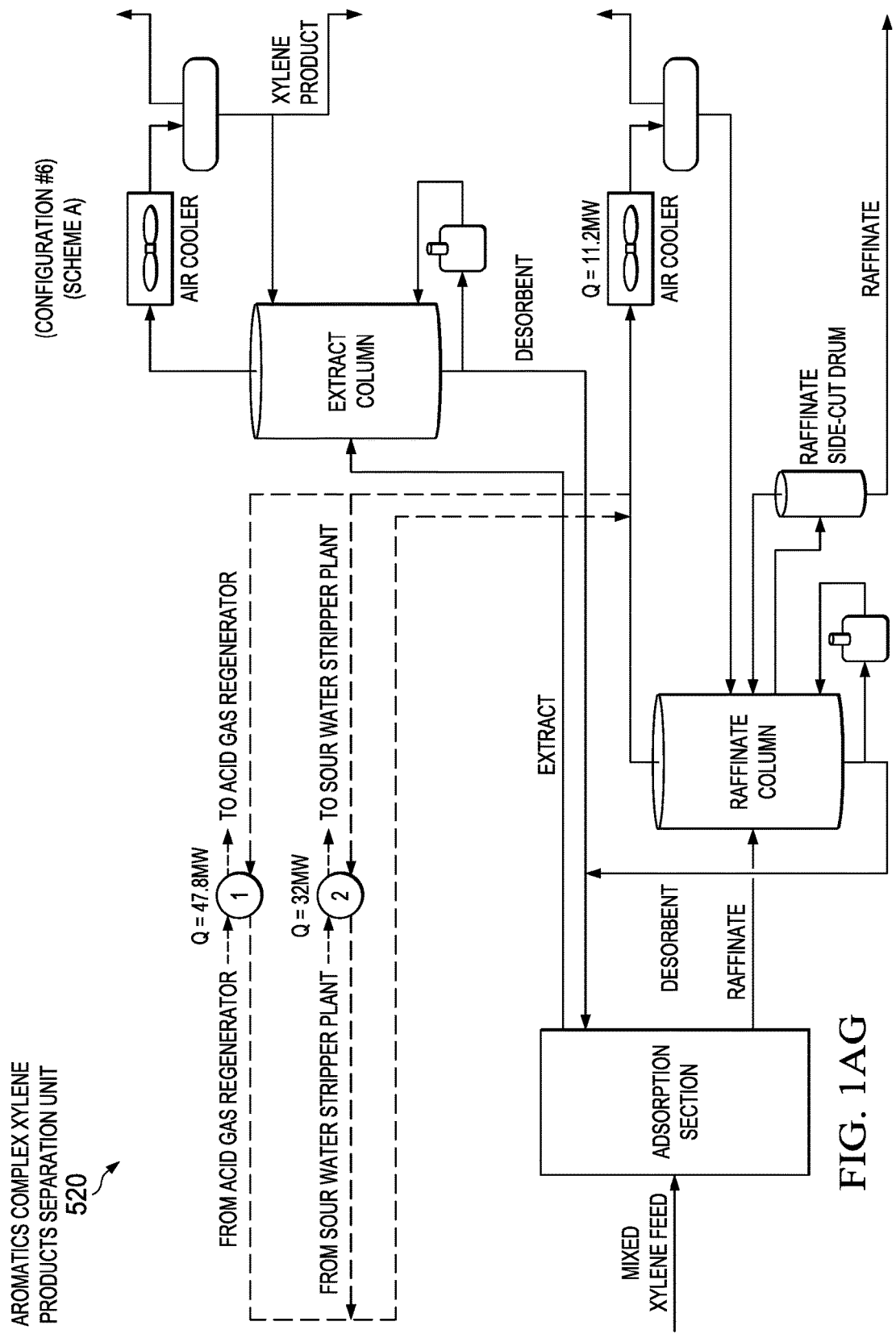
Figure 1A:
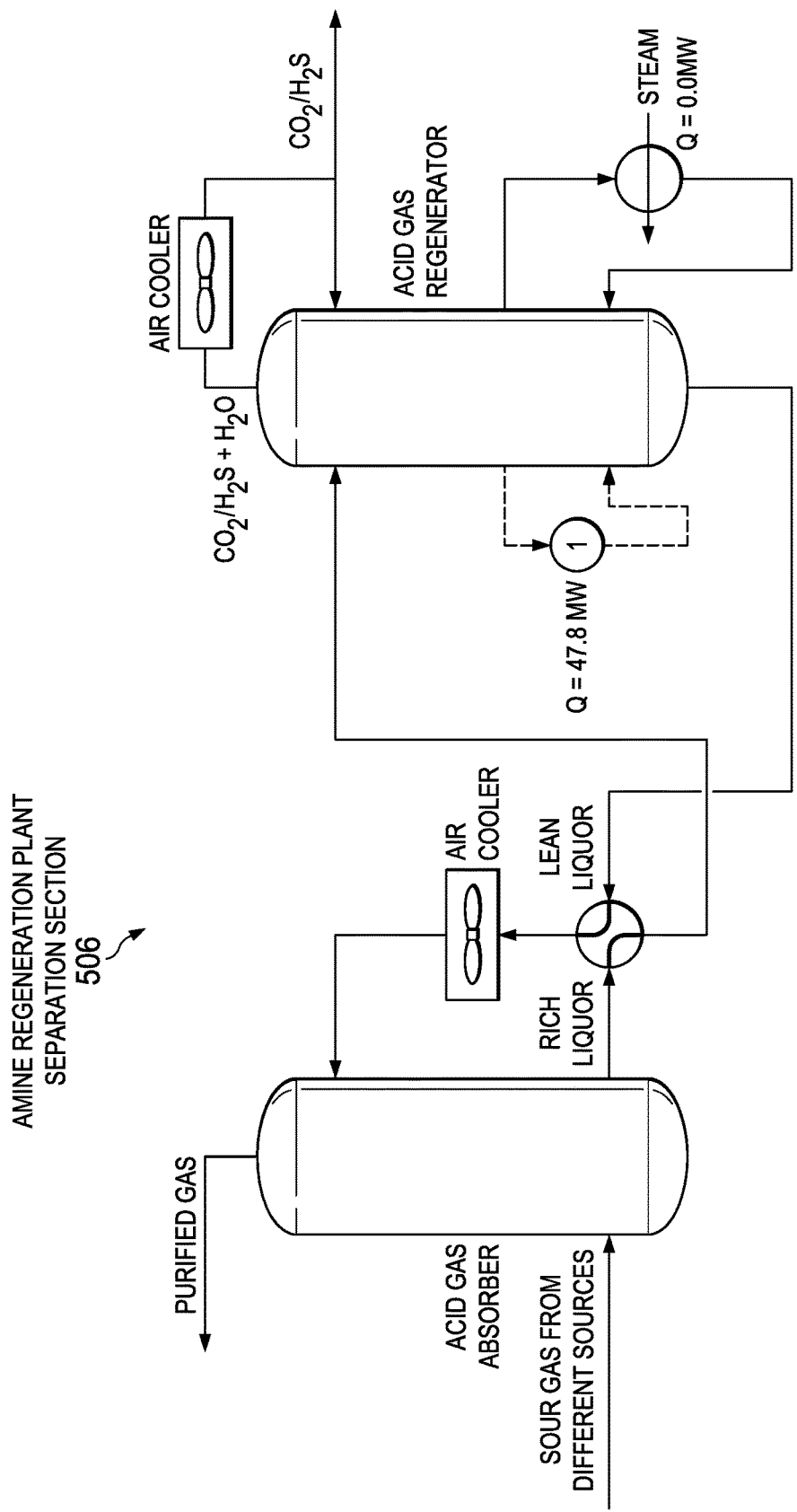
Figure 1A:
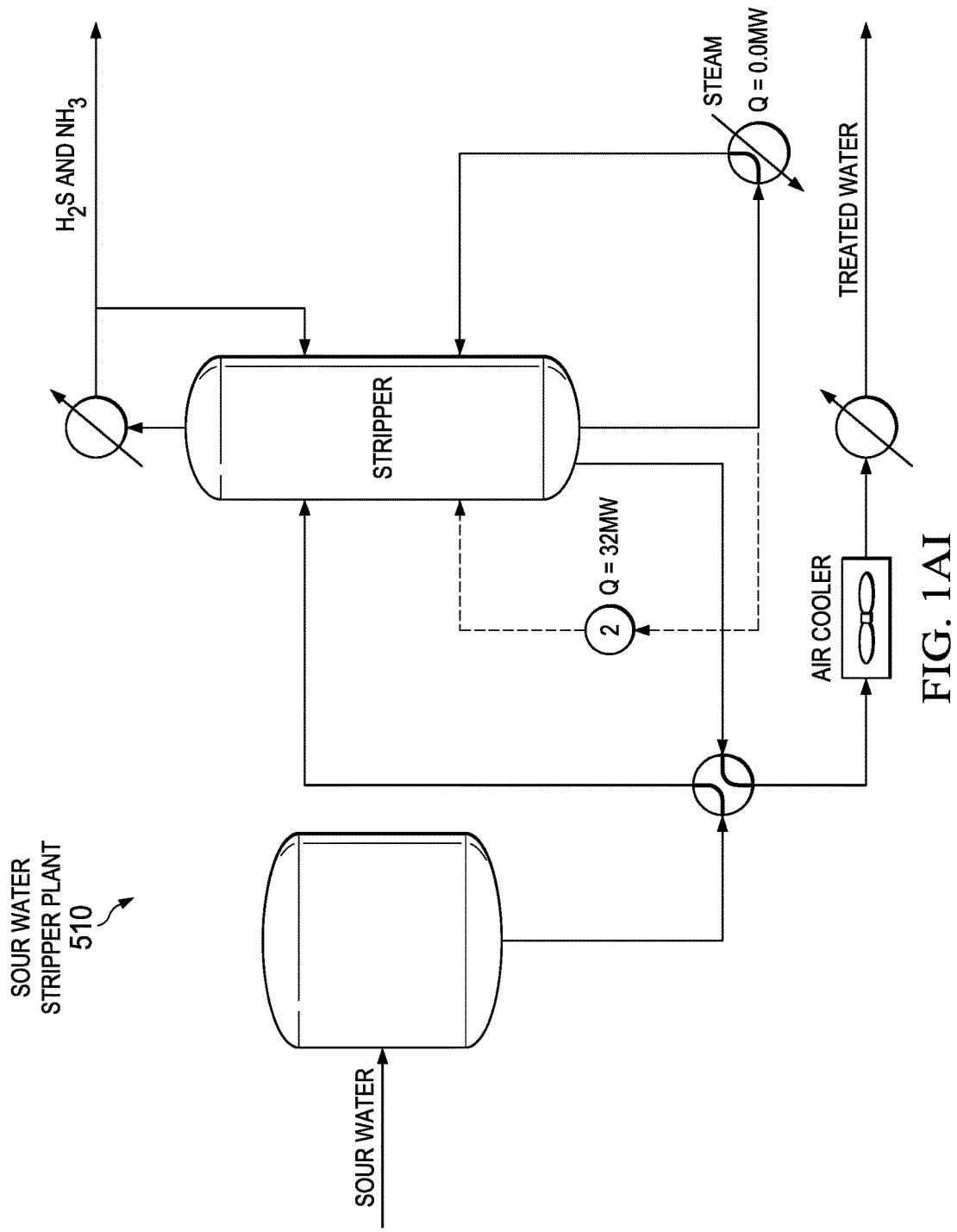
Figure 1A:
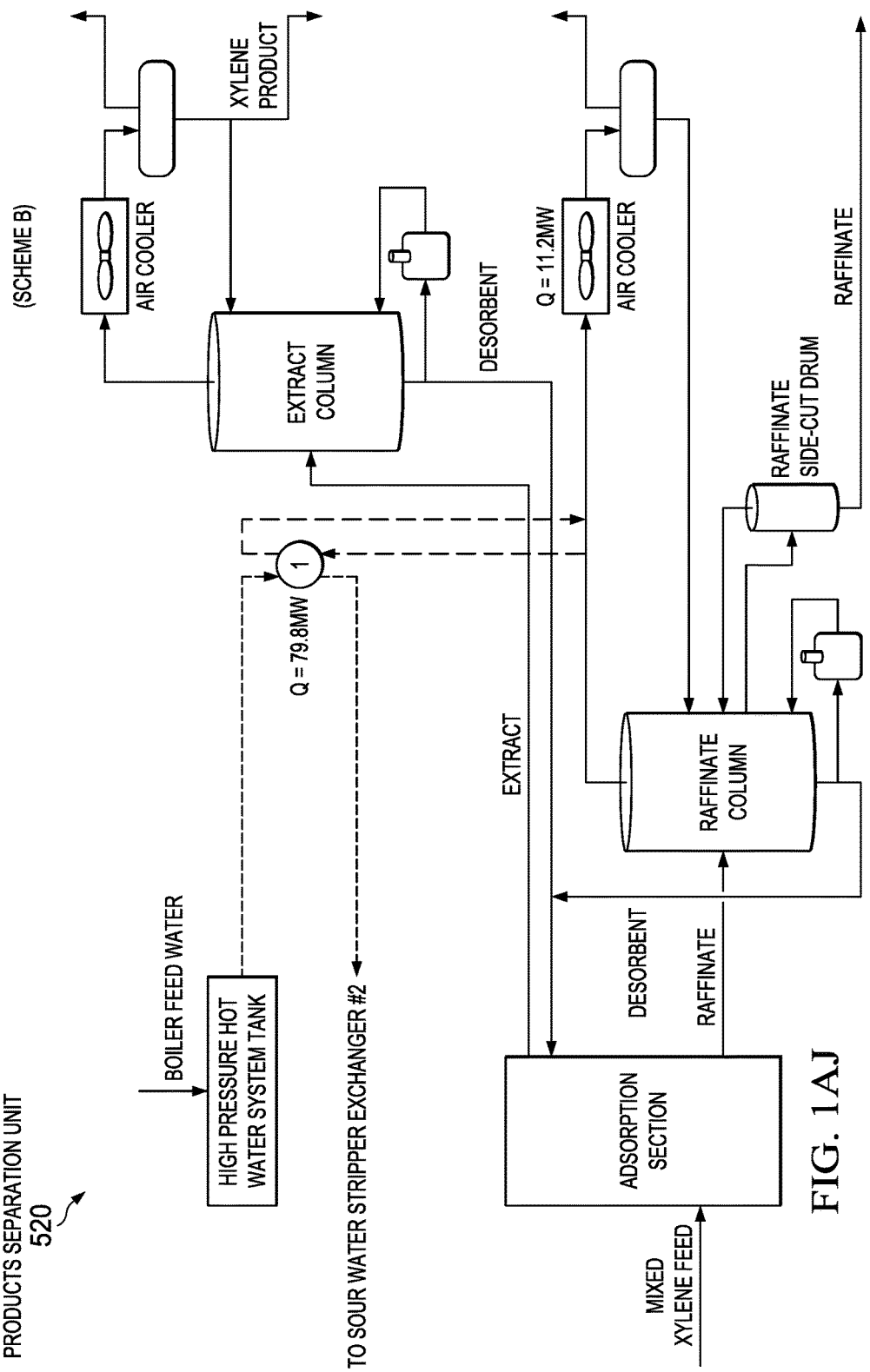
Figure 1A:
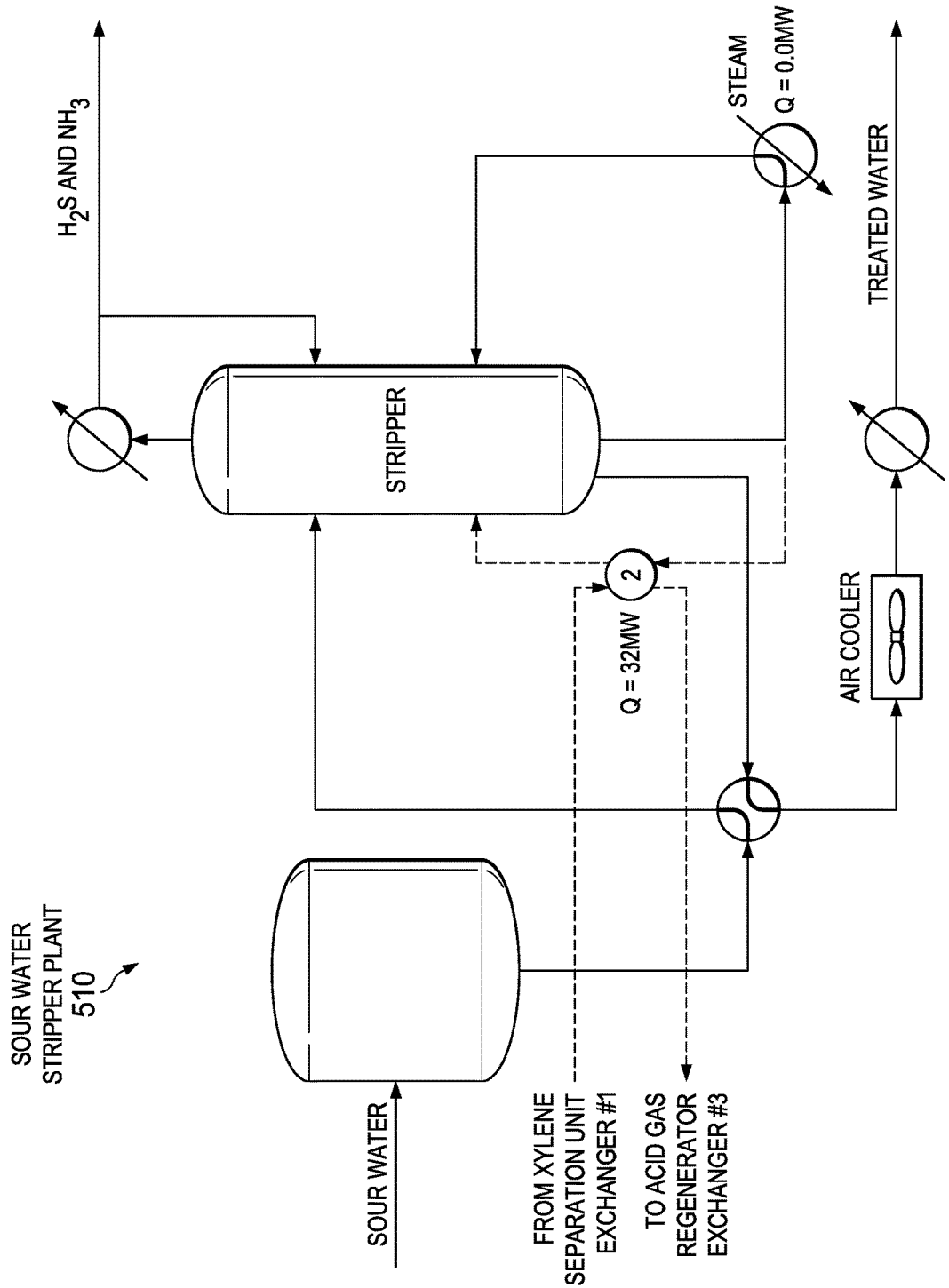
Figure 1A:
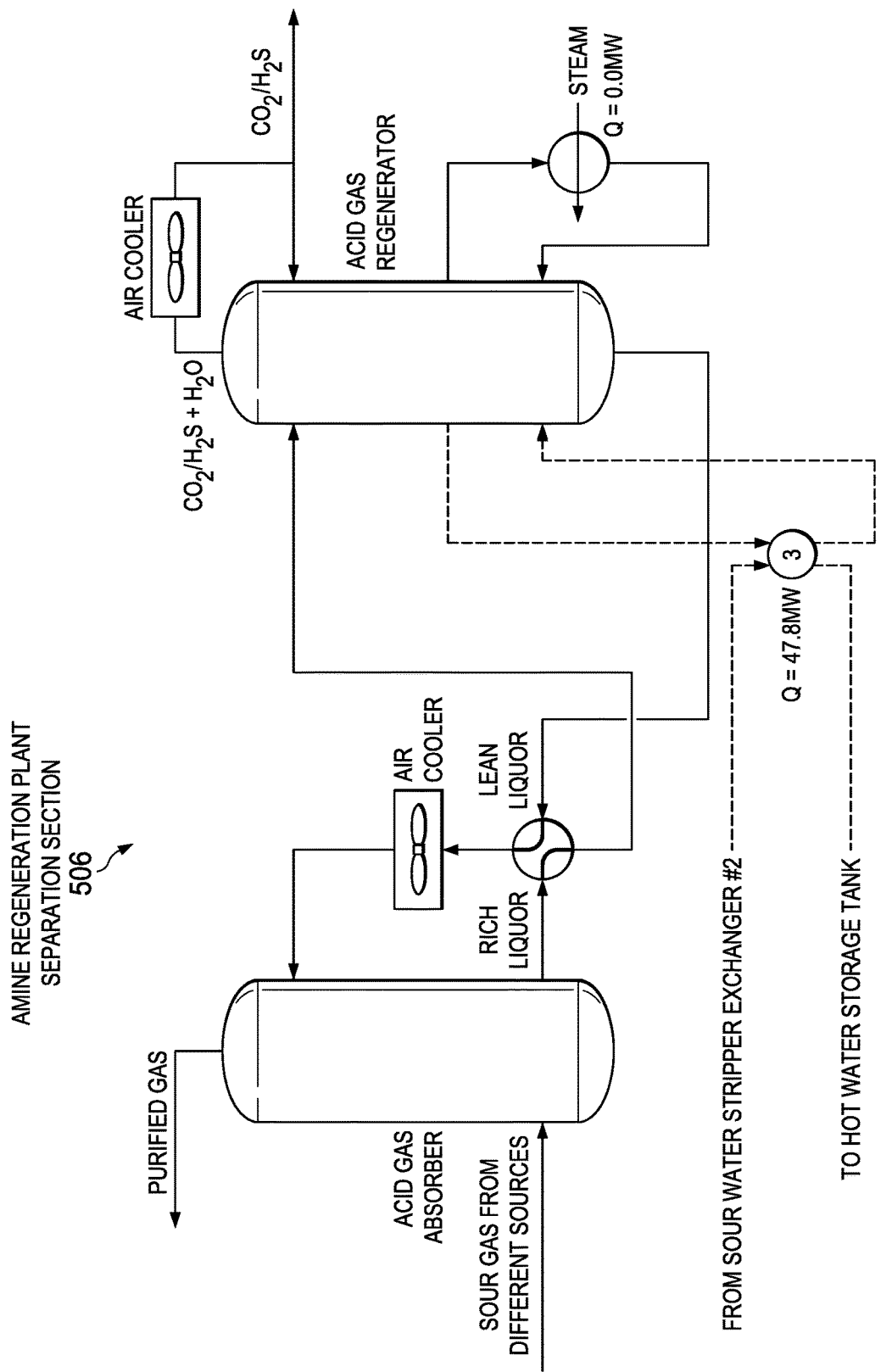
Figure 1A:
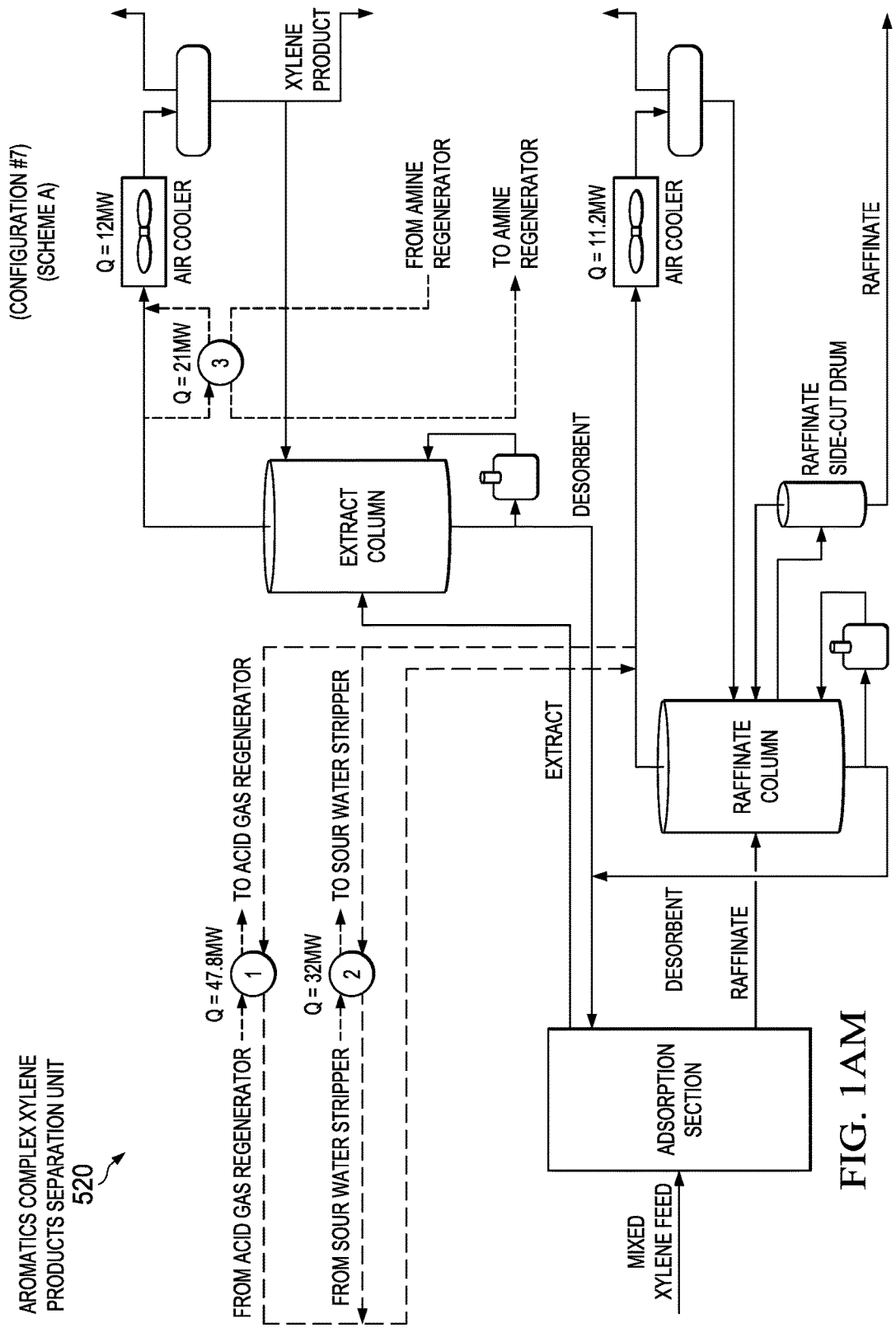
Figure 1A:
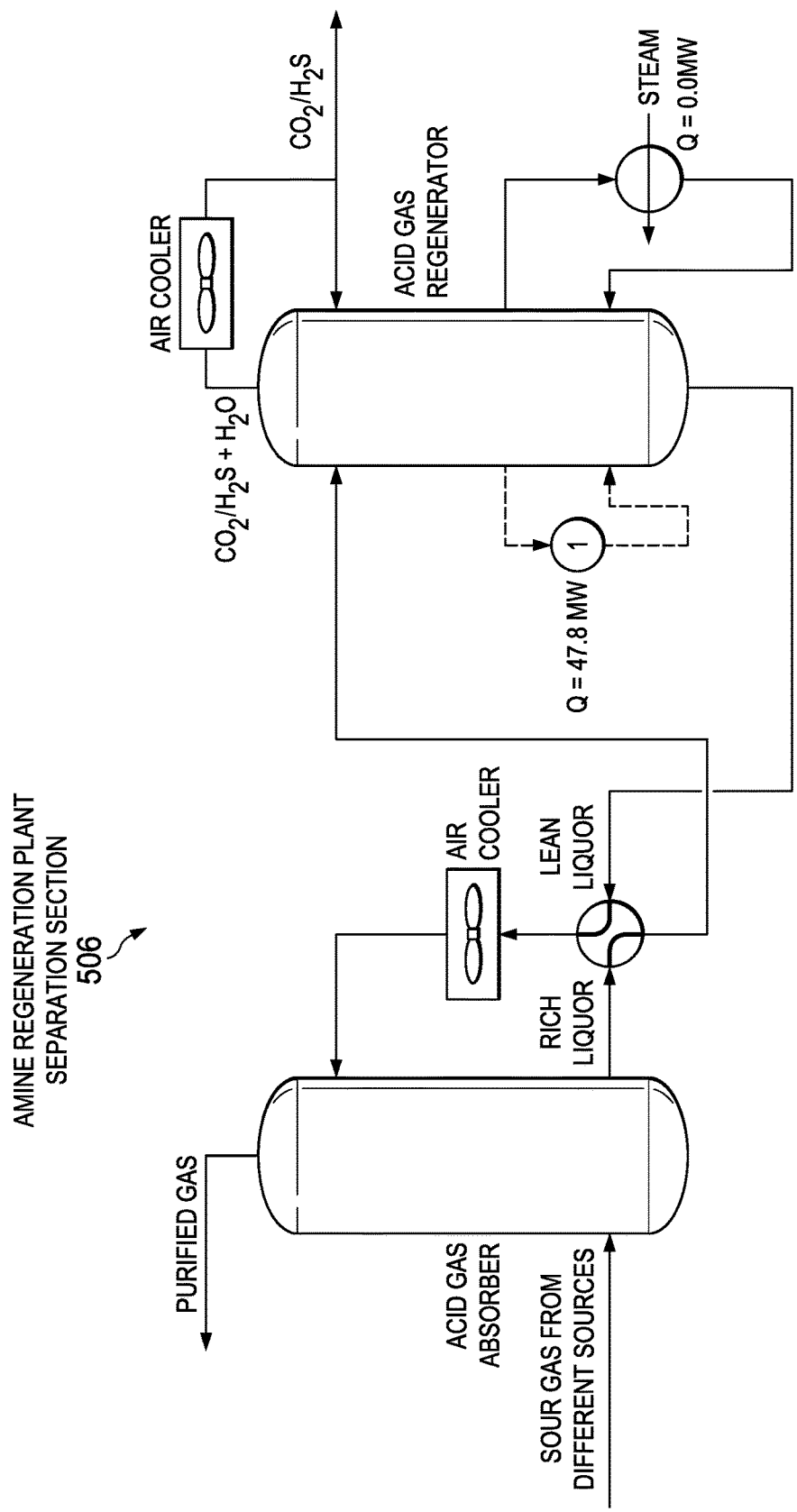
Figure 1A:
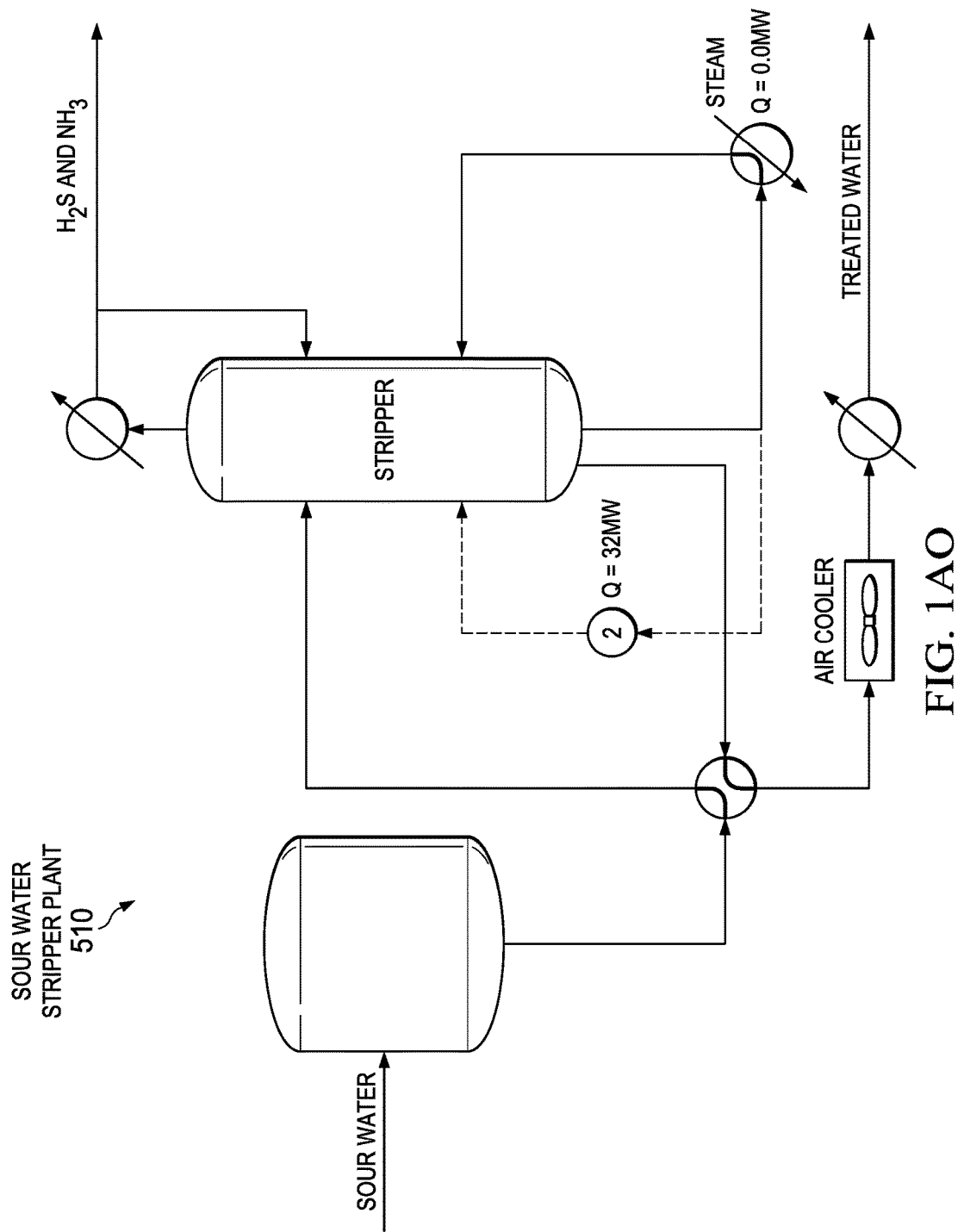
Figure 1A:
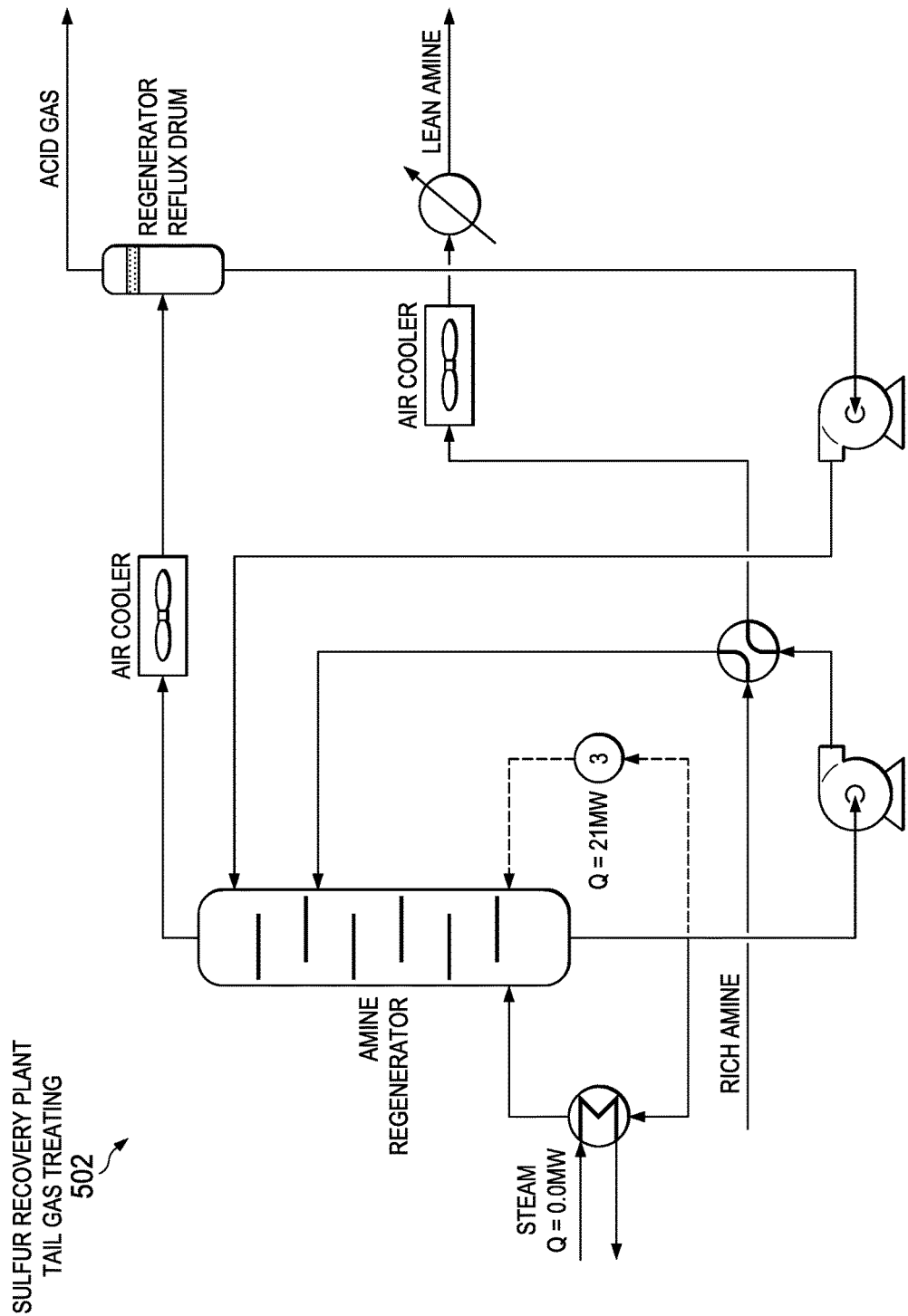
Figure 1A:
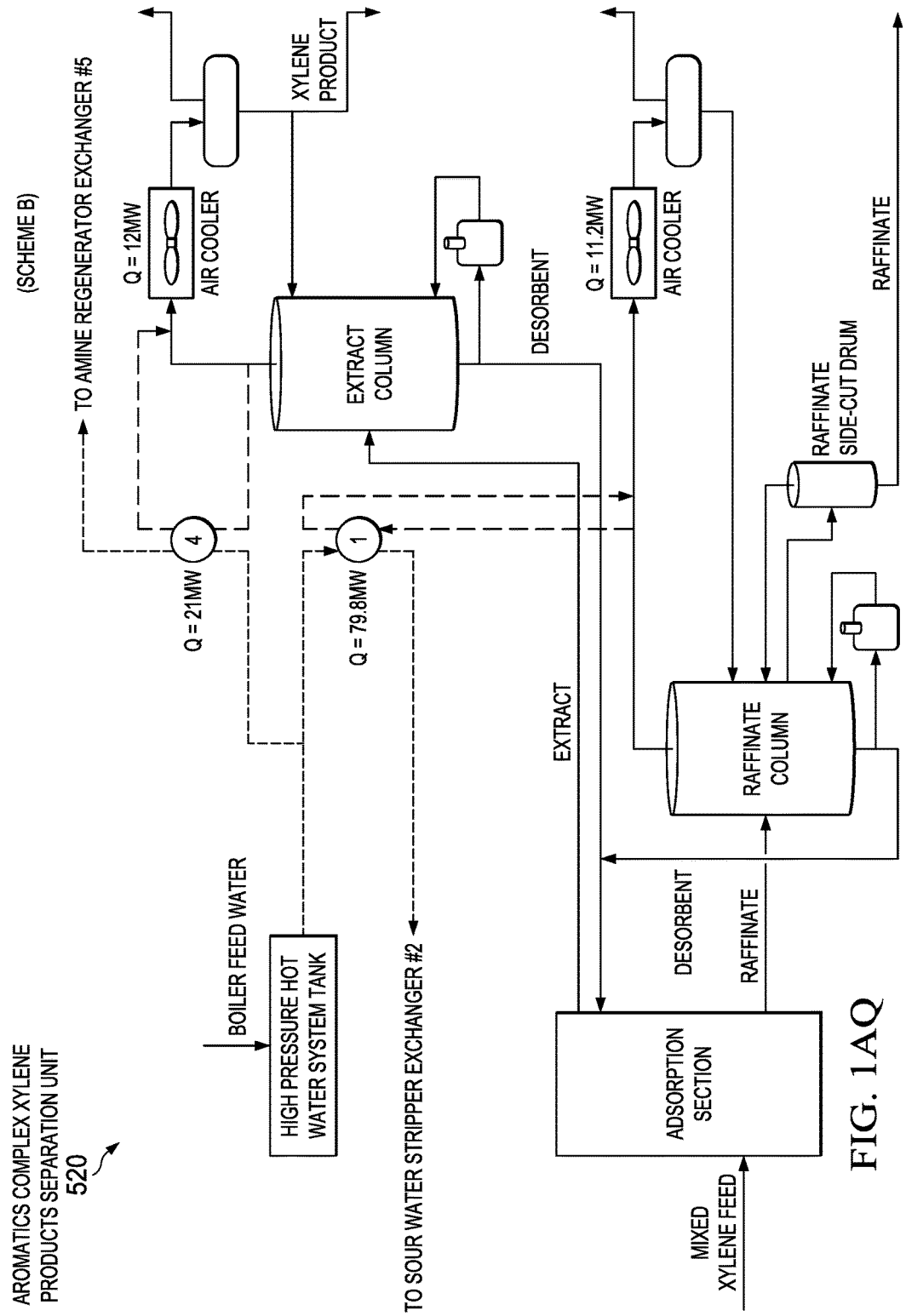
Figure 1A:
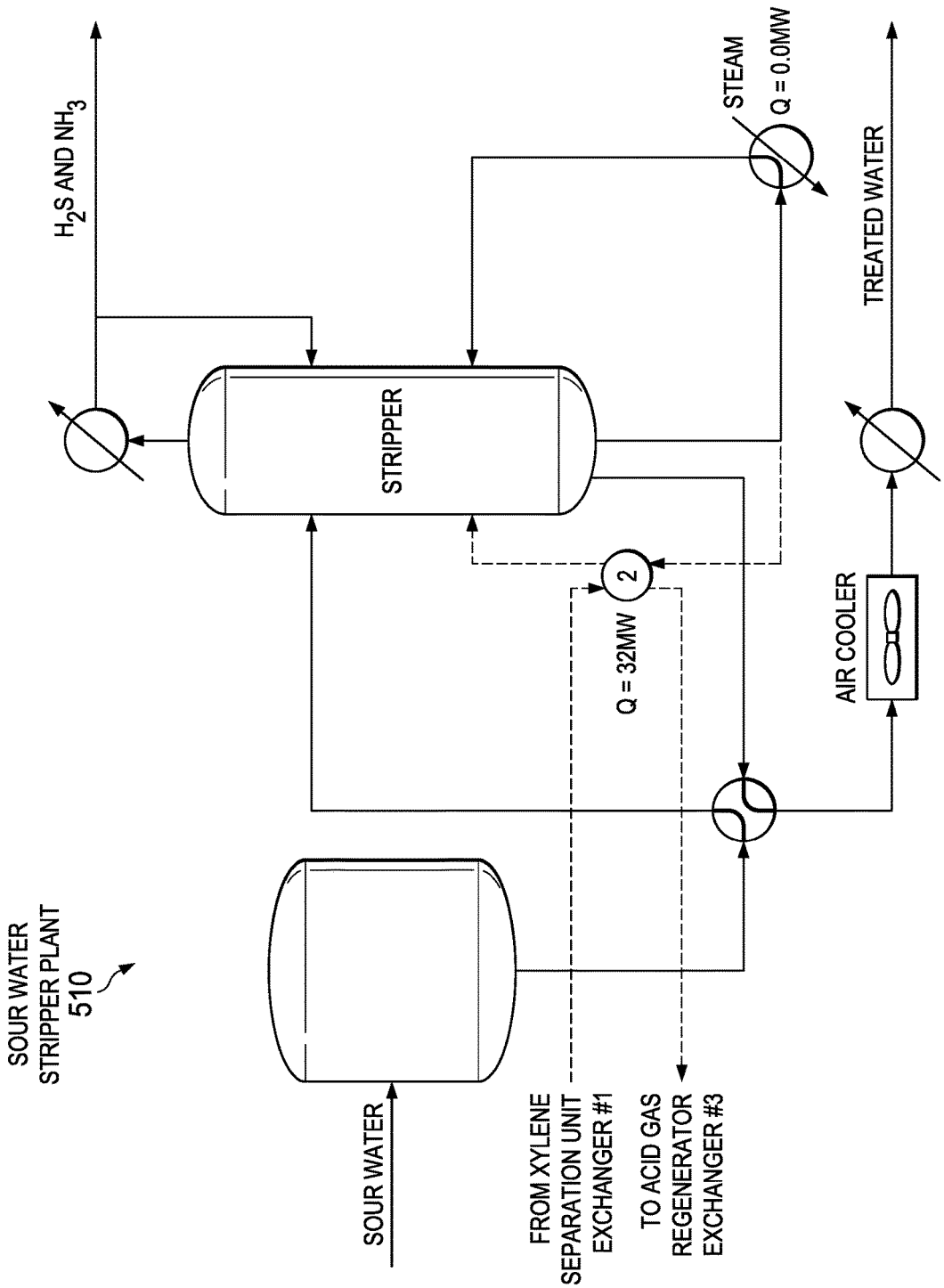
Figure 1A:
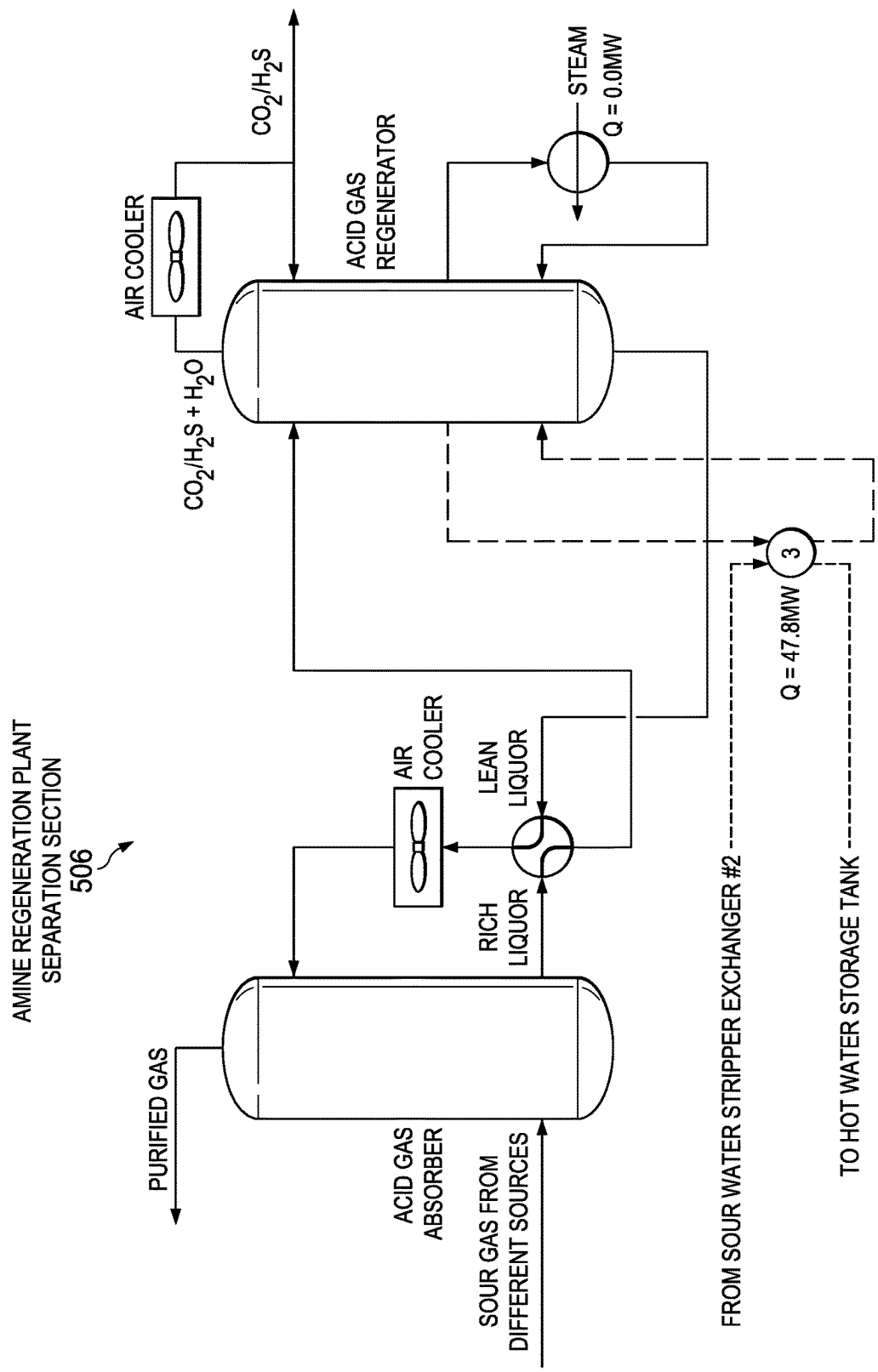
Figure 1A:
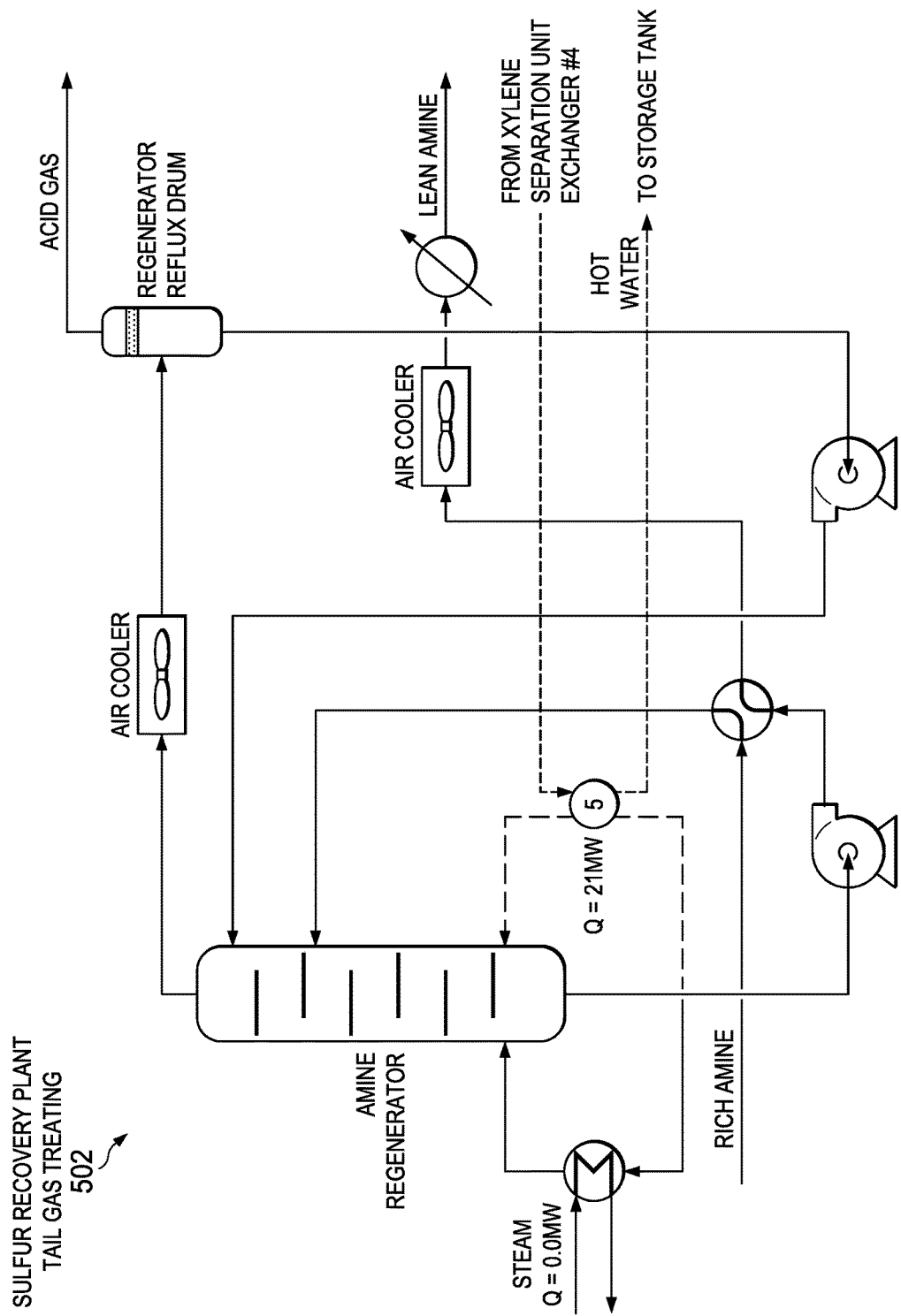

FIG. 1Z shows the sour water stripper plant 510 in a crude oil refinery facility. The second heated buffer fluid branch of the can be flowed to the sour water stripper plant 510. A sour water stripper bottom stream in the sour water stripper plant 510 can be heated using the second heated buffer fluid steam in a third heat exchanger with a thermal duty that can range between about 25 MW and 35 MW (for example, 32 MW). In this manner, the third heat exchanger is coupled to, in series with and is downstream of the first heat exchanger relative to the flow of buffer fluid. As shown in FIG. 1Z, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

The first heated buffer fluid stream exiting the second heat exchanger and the second heated buffer fluid stream passing from the third heat exchanger may recombine into a combined heated buffer fluid and flowed to the collection header or the buffer fluid tank for reuse. The combination of the second heat exchanger and the third heat exchanger can be coupled to, in series with and downstream of the first heat exchanger relative to the flow of the buffer fluid.

Such recovery and reuse of waste heat indirectly from the aromatics complex can result in decreasing or eliminating the heat energy to heat the sulfur recovery plant and the sour water stripper plant or combinations of them, such as by about 53 MW.

Configuration 5

FIGS. 1AA-1AF illustrate configurations and related scheme details for thermally integrating refining sub-units of an aromatics complex in the crude oil refining facility and other plants in the crude oil refining facility. In some implementations, the aromatics complex sub-units can include an aromatics complex xylene products separation unit. The other plants in the crude oil refining facility can include an amine regeneration plant and a sulfur recovery plant.

The thermal integration described in these configurations and illustrated in FIGS. 1AA-1AF can reduce the crude oil refining facility's energy consumption (for example, heating and cooling utilities). For example, a reduction in energy consumption by about 69 MW can translate to at least about 10% of the energy consumption in the crude oil refining facility. In certain schemes, a process stream (for example, a stream from one refining sub-unit of an aromatics plant or other process streams) can be used to directly heat another process stream (for example, a sulfur recovery plant stream or other process stream). In certain configurations, heat exchange between process streams can be implemented using an intermediate buffer fluid, for example, water, oil, or other buffer fluid.

Configuration 5—Scheme A

In some implementations, the streams in the amine regeneration plant and a sulfur recovery plant can be directly heated using one or more streams in the aromatics complex xylene separation unit. In some implementations, multiple first streams in first multiple plants plant can be directly heated using a second stream in a second plant. In some implementations, the first plants are the amine regeneration plant and the sulfur recovery plant; the multiple first streams are the acid gas regenerator bottoms and the amine regenerator bottoms streams; the second plant is the aromatics complex xylene separation unit and the second stream is the raffinate overheads column stream.

FIG. 1AA shows an aromatics complex xylene products separation unit 520. The raffinate overheads column stream can be flowed in the plant as a single stream and split into multiple streams or it can be flowed into the plant as multiple streams to facilitate heat recovery. The first raffinate column overhead stream can directly heat an acid gas regenerator bottoms stream in a first heat exchanger with a thermal duty that can range between about 45 MW and 55 MW (for example, 47.8 MW). The second raffinate column overheads stream can directly heat an amine regenerator bottom stream in a second heat exchanger with a thermal duty that can range between about 15 MW and 25 MW (for example, 21 MW). In this manner, the first heat exchanger and the second heat exchanger can be coupled to each other in parallel relative to the flow of raffinate column overhead stream. The transfer of heat directly to another process stream captures heat that would have otherwise been discharged to the environment. The branches of the raffinate column overheads streams are recombined and returned to the aromatics complex xylene product separation unit 520 for further processing.

FIG. 1AB shows the amine regeneration plant 506 in the crude oil refinery facility. The heated acid gas regeneration bottom stream can then be flowed to the amine regeneration plant separation section 506. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

FIG. 1AC shows the sulfur recovery plant 502 in the crude oil refinery facility. The heated amine regenerator bottom stream can then be flowed to the sulfur recovery plant 502. As shown in FIG. 1AC, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

Such recovery and reuse of waste heat directly from the aromatics complex xylene products separation unit can result in decreasing or eliminating the heat energy to heat the amine regeneration plant or the sulfur recovery plant or combinations of them, such as by about 69 MW.

Configuration 5—Scheme B

In some implementations, the multiple first streams in the multiple first plants in the crude oil refining facility can be indirectly heated using a second stream in a second plant. In some implementations, the multiple first plants include a sulfur recovery plant and an amine regeneration plant; the multiple first streams include an acid gas regenerator bottoms and an amine regeneration bottoms streams; the second plant includes an aromatics complex xylene separation unit; and the second stream includes raffinate column overheads stream.

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene products separation unit 520. The buffer fluid can be flowed into the plant as a single stream and split into multiple streams or it can be flowed into the plant as multiple streams.

FIG. 1AD shows an aromatics complex xylene products separation unit 520. A buffer fluid from a buffer fluid tank (for example, boiler feed water from a high pressure hot water system) can be flowed to an aromatics complex xylene product separation 520. The raffinate column overheads stream can be used to heat the buffer fluid in a first heat exchanger with a thermal duty that can range between about 65 MW and 75 MW (for example, 68.8 MW). The buffer fluid absorbs heat that would have otherwise been discharged to the environment. The raffinate column overhead stream is returned to the xylene products separation unit 520 for further processing.

The heated buffer fluid is directed to a collection header (or in some embodiments, a heated or insulated buffer fluid tank or storage unit that can hold heated collected buffer fluid for a period before use) and then can be flowed to either the sulfur recovery plant 502 and the amine regeneration plant 506.

FIG. 1AE shows the sulfur recovery plant 502 in a crude oil refinery facility. The heated buffer fluid can be flowed to the sulfur recovery plant 502. As shown in FIG. 1AE, an amine regenerator bottoms stream can be heated using the heated buffer fluid in a second heat exchanger with a thermal duty that can range between about 15 MW and 25 MW (for example, 21 MW). In this manner, the second heat exchanger is coupled to, in series with and is downstream of the first heat exchanger relative to the flow of heated buffer fluid. As shown in FIG. 1AE, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1AF shows the amine regeneration plant 506 in a crude oil refinery facility. The heated buffer fluid exiting the second heat exchanger can be flowed to the amine regeneration plant 506. As shown in FIG. 1AF, an acid gas regenerator bottom stream can be heated using the heated buffer fluid in a third heat exchanger with a thermal duty that can range between about 45 MW and 55 MW (for example, 47.8 MW). In this manner, the third heat exchanger is coupled to, in series with and is downstream of the first heat exchanger relative to the flow of heated buffer fluid. As shown in FIG. 1AF, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The heated buffer fluid branch exiting the third heat exchanger in the amine regenerator plant 506 can be flowed to the collection header or to the buffer fluid tank for reuse. In this manner, the second and the third heat exchangers are coupled to one another in series relative to the flow of the heated buffer fluid.

In some implementations, the heated buffer fluid can be flowed in series through the different plants. For example, the heated buffer fluid can be flowed first to the amine regeneration plant and then to the sulfur recovery plant. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly from the aromatics complex can result in decreasing or eliminating the heat energy to heat streams in both the sulfur recovery plant and the amine regeneration plant or combinations of them, such as by about 69 MW.

Configuration 6

FIGS. 1AG-1AL illustrate configurations and related scheme details for thermally integrating refining sub-units of an aromatics complex in the crude oil refining facility and other plants in the crude oil refining facility. In some implementations, the aromatics plant sub-units can include an aromatics complex xylene products separation unit. The other plants in the crude oil refining facility can include an amine regeneration plant and a sour water stripper plant.

The thermal integration described in these configurations and illustrated in FIGS. 1AG-1AL can reduce the crude oil refining facility's energy consumption (for example, heating and cooling utilities). For example, a reduction in energy consumption by about 80 MW can translate to at least about 12% of the energy consumption in the crude oil refining facility. In certain schemes, a process stream (for example, a stream from one refining sub-unit of an aromatics plant or other process streams) can be used to directly heat another process stream (for example, an acid gas regenerator bottom stream or other process stream). In certain configurations, heat exchange between process streams can be implemented using an intermediate buffer fluid, for example, water, oil, or other buffer fluid.

Configuration 6—Scheme A

In some implementations, the streams in the amine regeneration plant and the sour water stripper plant can be directly heated using one or more streams in the aromatics complex xylene separation unit. In some implementations, multiple first streams in first multiple plants plant can be directly heated using a second stream in a second plant. In some implementations, the first plants are the amine regeneration plant and the sour water stripper plant; the multiple first streams are the acid gas regenerator bottoms and the sour water stripper bottoms streams; the second plant is the aromatics complex xylene separation unit and the second stream is the raffinate overhead column stream.

FIG. 1AG shows an aromatics complex xylene products separation unit 520 in the crude oil refinery facility. The raffinate column overheads stream can be flowed in the plant as a single stream and split into multiple streams or it can be flowed into the plant as multiple streams to facilitate heat recovery. The first raffinate column overhead stream can directly heat an acid gas regeneration bottom stream in a first heat exchanger with a thermal duty that can range between about 45 MW and 55 MW (for example, 47.8 MW). The second raffinate column overhead stream can directly heat a sour water stripper bottom stream in a second heat exchanger with a thermal duty that can range between about 25 MW and 35 MW (for example, 32 MW). The transfer of heat directly to another process stream captures heat that would have otherwise been discharged to the environment. In this manner, the first heat exchanger and the second heat exchanger can be coupled to each other in parallel relative to the flow of raffinate column overhead stream. The raffinate column overheads streams are recombined and returned to the aromatics complex xylene product separation unit 520 for further processing.

FIG. 1AH shows the amine regeneration plant 506 in the crude oil refinery facility. The heated acid gas regenerator bottoms stream can then be flowed to the amine regeneration plant 506. As shown in FIG. 1AH, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

FIG. 1AH shows the sour water stripper plant 510 in the crude oil refinery facility. The heated sour water stripper plant bottoms stream can then be flowed to the sour water stripper plant 510. As shown in FIG. 1AI, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Such recovery and reuse of waste heat directly from the aromatics complex can result in decreasing or eliminating the heat energy to heat the sour water stripper plant or the amine regeneration plant or combinations of them, such as by about 80 MW.

Configuration 6—Scheme B

In some implementations, the multiple first streams in the multiple first plant in the crude oil refining facility can be indirectly heated using a second stream in a second plant. In some implementations, the multiple first plants include a sour water stripper plant and an amine regeneration plant; the multiple first streams include a sour water stripper bottoms and an acid gas regenerator bottoms streams; the second plant includes an aromatics complex xylene separation unit; and the second stream includes raffinate column overhead stream.

Indirectly heating the streams can include heating the streams through a buffer fluid, for example, oil, water, or other buffer fluid. A buffer fluid (for example, high pressure water) from a buffer fluid tank (for example, hot water tank) is flowed to the aromatics complex xylene products separation unit 520. The buffer fluid can be flowed into each plant as a single stream and split into multiple streams or it can be flowed into a plant as multiple streams.

FIG. 1AJ shows the aromatics complex xylene products separation unit 520 in a crude oil refinery facility. A buffer fluid from a buffer fluid tank (for example, boiler feed water from a high pressure hot water system) can be flowed to an aromatics complex xylene products separation unit 520. The raffinate column overheads stream can be used to heat the buffer fluid in a first heat exchanger with a thermal duty that can range between about 75 MW and 85 MW (for example, 79.8 MW). The buffer fluid absorbs heat that would have otherwise been discharged to the environment. The raffinate column overheads stream is returned to the xylene products separation unit 520 for further processing.

The heated buffer fluid is directed to a collection header (or in some embodiments, a heated or insulated buffer fluid tank or storage unit that can hold heated collected buffer fluid for a period before use) and then can be flowed to either the sour water stripper plant 510 or the amine regeneration plant 506.

FIG. 1AK shows the sour water stripper plant 510 in a crude oil refinery facility. The heated buffer fluid can be flowed to the sour water stripper plant 510. As shown in FIG. 1AK, a sour water stripper plant bottoms stream can be heated using the heated buffer fluid received in a second heat exchanger with a thermal duty that can range between about 25 MW and 35 MW (for example, 32 MW). In this manner, the second heat exchanger is coupled to, in series with and is downstream of the first heat exchanger relative to the flow of heated buffer fluid. As shown in FIG. 1AK, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1AL shows amine regeneration plant 506 in a crude oil refinery facility. The heated buffer fluid exiting the second heat exchanger can be flowed to the amine regeneration plant 506. As shown in FIG. 1AL, an acid gas regenerator bottom stream can be heated using the heated buffer fluid in a third heat exchanger with a thermal duty that can range between about 45 MW and 55 MW (for example, 47.8 MW). In this manner, the third heat exchanger is coupled to, in series with and is downstream of the first heat exchanger relative to the flow of heated buffer fluid. As shown in FIG. 1AL, in this configuration the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The heated buffer fluid branch exiting the third heat exchanger in the acid gas regenerator 506 can be flowed to the collection header or to the buffer fluid tank for reuse. In this manner, the second and the third heat exchangers are coupled to one another in series relative to the flow of the heated buffer fluid.

In some implementations, the heated buffer fluid can be flowed in series through the different plants. For example, the heated buffer fluid can be flowed first to the amine regeneration plant and then to the sour water stripper plant. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly from the aromatics complex can result in decreasing or eliminating the heat energy to heat streams in both the sour water stripper plant and the amine regeneration plant or combinations of them, such as by about 80 MW.

Configuration 7

FIGS. 1AM-1AT illustrate configurations and related scheme details for thermally integrating refining sub-units of an aromatics complex in the crude oil refining facility and other plants in the crude oil refining facility. In some implementations, the aromatics complex sub-units can include an aromatics complex xylene products separation unit. The other plants in the crude oil refining facility can include an amine regeneration plant, a sour water stripper plant and a sulfur recovery plant.

The thermal integration described in these configurations and illustrated in FIGS. 1AM-1AT can reduce the crude oil refining facility's energy consumption (for example, heating and cooling utilities). For example, a reduction in energy consumption by about 98 MW, which translates to at least about 15% of the energy consumption in the crude oil refining facility. In certain schemes, a process stream (for example, a stream from one refining sub-unit of an aromatics plant or other process streams) can be used to directly heat another process stream (for example, a sulfur plant stream or other process stream). In certain configurations, heat exchange between process streams can be implemented using an intermediate buffer fluid, for example, water, oil, or other buffer fluid.

Configuration 7—Scheme A

In some implementations, the streams in the amine regeneration plant, the sour water stripper plant and the sulfur recovery plant can be directly heated using one or more streams in the aromatics complex xylene products separation unit. In some implementations, multiple first streams in first multiple plants plant can be directly heated using multiple second streams in a second plant. In some implementations, the first plants are the amine regeneration plant, a sulfur recovery plant and the sour water stripper plant; the multiple first streams are the acid gas regenerator bottoms, the amine regenerator bottoms and the sour water stripper bottoms streams; the second plant is the aromatics complex xylene products separation unit; and the second streams are the raffinate column overheads and the extract column overheads streams.

FIG. 1AM shows an aromatics complex xylene products separation unit 520. The raffinate overheads column stream can be flowed in the plant as a single stream and split into multiple streams or it can be flowed into the plant as multiple streams to facilitate heat recovery. The first raffinate column overheads stream can directly heat an acid gas regenerator bottom stream in a first heat exchanger with a thermal duty that can range between about 45 MW and 55 MW (for example, 47.8 MW). The second raffinate column overheads stream can directly heat a sour water stripper bottom stream in a second heat exchanger with a thermal duty that can range between about 25 MW and 35 MW (for example, 32 MW). In this manner, the first heat exchanger and the second heat exchanger can be coupled to each other in parallel relative to the flow of raffinate column overheads stream. The transfer of heat directly to another process stream captures heat that would have otherwise been discharged to the environment. The raffinate column overheads stream can be recombined and returned to the aromatics complex xylene product separation unit 520 for further processing.

FIG. 1AM also shows an extract column overheads stream. The extract column overhead stream can directly heat an amine regenerator bottom stream in a third heat exchanger with a thermal duty that can range between about 15 MW and 25 MW (for example, 21 MW). The third exchanger captures heat that would have otherwise been discharged to the environment. The extract column overheads stream is returned to the aromatics complex xylene product separation unit 520 for further processing.

FIG. 1AN shows the amine regeneration plant 506 in the crude oil refinery facility. The heated acid gas regenerator bottoms stream can then be flowed to the amine regeneration plant 506. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

FIG. 1AO shows the sour water stripper plant 510 in the crude oil refinery facility. The heated sour water stripper bottoms stream can then be flowed to the sour water stripper plant 510. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1AP shows the sulfur recovery plant 502 in the crude oil refinery facility. The heated amine regenerator bottoms stream can then be flowed to the sulfur recovery plant 502. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

Such recovery and reuse of waste heat directly from the aromatics complex can result in decreasing or eliminating the heat energy to heat the amine regeneration plant, sour water stripper plant, the sulfur recovery plant or combinations of them, such as by about 98 MW.

Configuration 7—Scheme B

In some implementations, the multiple first streams in the multiple first plants in the crude oil refining facility can be indirectly heated using the multiple second streams in a second plant. In some implementations, the multiple first plants include a sulfur recovery plant, a sour water stripper plant and an amine regeneration plant; the multiple first streams include an acid gas regenerator bottoms, a sour water stripper bottoms and an amine regeneration bottoms streams; the second plant includes an aromatics complex xylene separation unit; and the second streams include a raffinate column overheads and an extract column overheads streams.

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene products separation unit 520. The buffer fluid can be flowed into the plant as a single stream and split into multiple streams or it can be flowed into the plant as multiple streams.

FIG. 1AQ shows an aromatics complex xylene products separation unit 520. A buffer fluid from a buffer fluid tank (for example, boiler feed water from a high pressure hot water system) can be flowed to an aromatics complex xylene product separation unit 520. The buffer fluid can be split into a first buffer fluid stream and a second buffer fluid stream. A raffinate column overhead stream can be used to heat the first buffer fluid stream in a first heat exchanger with a thermal duty that can range between about 75 MW and 85 MW (for example, 79.8 MW). An extract column overhead stream can be used to heat the second buffer fluid stream of the in a fourth heat exchanger with a thermal duty that can range between about 15 MW and 25 MW (for example, 21 MW). In this manner, the first heat exchanger and the fourth heat exchanger can be coupled to each other in parallel relative to the flow of buffer fluid. The buffer fluid absorbs heat that would have otherwise been discharged to the environment. The raffinate column overheads stream and the extract column overheads stream are returned to the xylene products separation unit 520 for further processing.

The heated buffer fluid can be directed to a collection header (or in some embodiments, a heated or insulated buffer fluid tank or storage unit that can hold heated collected buffer fluid for a period before use) and then can be flowed to the sulfur recovery plant 502, the sour water stripper plant 510 and the amine regeneration plant 506 in any particular order. In this embodiment, the first heated buffer fluid stream and the second heated buffer fluid stream, are maintained separately from one another and are not combined into a common heated buffer fluid collection header.

FIG. 1AR shows the sour water stripper plant 510 in a crude oil refinery facility. The first heated buffer fluid stream exiting the first heat exchanger can be flowed to the sour water stripper plant 510. A sour water stripper bottoms stream can be heated using the first heated buffer fluid in a second heat exchanger with a thermal duty that can range between about 25 MW and 35 MW (for example, 32 MW). In this manner, the second heat exchanger is coupled to, is downstream of and is in series with the first heat exchanger relative to the flow of heated buffer fluid. As shown in FIG. 1AR, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1AS shows the amine regeneration plant 506 in a crude oil refinery facility. The first heated buffer fluid stream exiting the second heat exchanger can be flowed to the amine regeneration plant 506. As shown in FIG. 1AS, an acid gas regenerator bottoms stream can be heated using the first heated buffer fluid branch in a third heat exchanger with a thermal duty that can range between about 45 MW and 55 MW (for example, 47.8 MW). In this manner, the third heat exchanger is coupled to, in series with and is downstream of the first heat exchanger relative to the flow of heated buffer fluid. As shown in FIG. 1AF, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

FIG. 1AT shows the sulfur recovery plant 502 in a crude oil refinery facility. The second heated buffer fluid stream exiting the fourth heat exchanger can be flowed to the sulfur recovery plant 502. As shown in FIG. 1AT, an amine regenerator bottoms stream can be heated using the second heated buffer fluid in a second heat exchanger with a thermal duty that can range between about 15 MW and 25 MW (for example, 21 MW). In this manner, the fifth heat exchanger is coupled to, in series with and is downstream of the fourth heat exchanger relative to the flow of buffer fluid. As shown in FIG. 1AT, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

The first heated buffer fluid stream exiting the third heat in the amine regeneration plant and the second heated buffer fluid stream exiting the fifth heat exchanger in the sulfur recovery plant can be flowed to the collection header or to the buffer fluid tank for reuse. In this manner, the second and the third heat exchangers are coupled to one another in series relative to the flow of the heated buffer fluid. As well, the set of the second and the third heat exchangers and the fifth heat exchanger are coupled in series relative to the flow of heated buffer fluid.

In some implementations, the heated buffer fluid can be flowed in series through the different plants. For example, the second heated buffer fluid can be flowed first to the amine regeneration plant then to the sour water stripper plant. The second heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly from the aromatics complex can result in decreasing or eliminating the heat energy to heat the sulfur recovery plant, the sour water stripper plant and the amine regeneration plant or combinations of them, such as by about 98 MW.

In summary, this disclosure describes configurations and related processing schemes of specific inter-plants and hybrid, intra- and inter-plants waste heat recovery schemes for thermal energy consumption reduction in integrated refining-petrochemical facilities synthesized for grassroots medium grade crude oil semi-conversion refineries to increase energy efficiency from specific portions of low grade waste heat sources. The disclosure also describes configurations and related processing schemes of specific inter-plants and hybrid, intra- and inter-plants waste heat recovery schemes for thermal energy consumption reduction in integrated refining-petrochemical facilities synthesized for integrated medium grade crude oil semi-conversion refineries and aromatics complex for increasing energy efficiency from specific portions of low grade waste sources.

The economics of industrial production, the limitations of global energy supply, and the realities of environmental conservation are concerns for all industries. It is believed that the world's environment has been negatively affected by global warming caused, in part, by the release of GHG into the atmosphere. Implementations of the subject matter described here can alleviate some of these concerns, and, in some cases, prevent certain refineries, which are having difficulty in reducing their GHG emissions, from having to shut down. By implementing the techniques described here, specific plants in a refinery or a refinery, as a whole, can be made more efficient and less polluting by recovery and reusing from specific portions of low grade waste heat sources.

Thus, particular implementations of the subject matter have been described. Other implementations are within the scope of the following claims.

The invention claimed is:

1. A system comprising:
an aromatics complex of a crude oil refining facility, the aromatics complex configured to perform at least one oil refining process, the aromatics plant included in a plurality of oil refining plants of the crude oil refining facility, a plurality of streams at respective temperatures flowing between the plurality of oil refining plants, wherein the aromatics complex comprises a plurality of aromatics complex sub-units comprising an aromatics complex xylene products separation unit and a benzene extraction unit;
a first oil refining plant included in the plurality of oil refining plants, the first oil refining plant being different from the aromatics complex, wherein the plurality of oil refining plants comprise a sulfur recovery plant, a gas separation plant through which a gas separation plant stream comprising at least one of C2 to C4 flows, a hydrogen plant, a sour water stripper plant, an amine regeneration plant through which an acid gas regenerator bottoms stream comprising a weak amine salt flows, and a diesel hydro-treating plant;
a flow control system connected to the plurality of oil refining plants, the flow control system configured to:
flow an aromatics complex stream comprising a raffinate overheads column stream in the aromatics complex to a first heat exchanger of a heat exchanger system comprising one or more heat exchangers, and
flow a first stream from the first oil refining plant to the first heat exchanger; and
the heat exchanger system comprising:
the first heat exchanger configured to transfer heat between the aromatics complex stream and the first stream from the first oil refining plant.

2. The system of claim 1, wherein the aromatics complex stream comprises a plurality of streams from one or more of the plurality of aromatics complex sub-units, and wherein the heat exchanger system is configured to directly heat the first stream from the first oil refining plant using the plurality of streams from the one or more of aromatics complex sub-units.

3. The system of claim 2, wherein the aromatics complex stream comprises the raffinate overheads column stream in the aromatics complex xylene products separation unit, and wherein, to directly heat the first stream, the heat exchanger system comprises:
the first heat exchanger configured to heat an amine regenerator bottoms stream in the sulfur recovery plant using a first branch of the raffinate overheads column stream,
a second heat exchanger configured to heat a C3/C4 splitter bottoms stream in the gas separation plant using a second branch of the raffinate overheads column stream,
a third heat exchanger configured to heat a de-ethanizer bottoms stream in the gas separation plant using a third branch of the raffinate overheads column stream, and
wherein the flow control system is configured to:
flow the heated amine regenerator bottoms stream to the sulfur recovery plant, and
flow the heated C3/C4 splitter bottoms stream and the heated de-ethanizer bottoms stream to the gas separation plant.

4. The system of claim 3, wherein the first heat exchanger, the second heat exchanger and the third heat exchanger are fluidically coupled to each other in parallel.

5. The system of claim 2, wherein the heat exchanger system comprises:
the first heat exchanger configured to heat a raffinate splitter bottom stream in the aromatics complex using a low temperature shift (LTS) hydrogen plant stream in the hydrogen plant,
a second heat exchanger configured to heat a first branch of a sour water stripper bottom cold stream in the sour water stripper plant using a diesel hydro-treating stripper overhead stream in the diesel hydro-treating plant, and
a third heat exchanger configured to heat a second branch of the sour water stripper bottom cold stream using a diesel hydro-treating stripper bottom product stream in the diesel hydro-treating plant,
wherein the flow control system is configured to:
flow the heated raffinate splitter bottom stream to the benzene extraction unit, and
flow the heated first branch and the heated second branch of the sour water stripper bottom cold stream to the sour water stripper plant.

6. The system of claim 5, wherein the second heat exchanger and the third heat exchanger are fluidically coupled to each other in parallel.

7. The system of claim 2, wherein the aromatics complex stream comprises the raffinate overheads column stream in the aromatics complex xylene products separation unit, and wherein, to directly heat the first stream, the heat exchanger system comprises:
the first heat exchanger configured to heat a sour water stripper bottom cold stream in the sour water stripper plant using a first branch of the raffinate overheads column stream,
a second heat exchanger configured to heat a C3/C4 splitter bottoms stream in the gas separation plant using a second branch of the raffinate overheads column stream, and
a third heat exchanger configured to heat a de-ethanizer bottoms stream in the gas separation plant using a third branch of the raffinate overheads column stream,
wherein the flow control system is configured to:
flow the heated sour water stripper bottom cold stream to the sour water stripper plant, and
flow the heated C3/C4 splitter bottoms stream and the heated de-ethanizer bottoms stream to the gas separation plant.

8. The system of claim 7, wherein the first heat exchanger, the second heat exchanger and the third heat exchanger are coupled to each other in parallel.

9. The system of claim 2, wherein the aromatics complex stream comprises the raffinate overheads column stream in the aromatics complex xylene products separation unit, and wherein, to directly heat the first stream, the heat exchanger system comprises:
the first heat exchanger configured to heat a sour water stripper bottom cold stream in the sour water stripper plant using a first branch of the raffinate overheads column stream, and
a second heat exchanger configured to heat an amine regenerator bottoms stream using a second branch of the raffinate overheads column stream,
wherein the flow control system is configured to:
flow the heated sour water stripper bottom cold stream to the sour water stripper plant, and
flow the heated amine regenerator bottoms stream to the sulfur recovery plant.

10. The system of claim 9, wherein the first heat exchanger and the second heat exchanger are fluidically coupled to each other in parallel.

11. The system of claim 2, wherein the aromatics complex stream comprises the raffinate overheads column stream in the aromatics complex xylene products separation unit, and wherein, to directly heat the first stream, the heat exchanger system comprises:
the first heat exchanger configured to heat the acid gas regenerator bottom stream in the amine regeneration plant using a first branch of the raffinate overheads column stream, and
a second heat exchanger configured to heat an amine regenerator bottoms stream using a second branch of the raffinate overheads column stream,
wherein the flow control system is configured to:
flow the heated acid gas regenerator bottom cold stream to the amine regeneration plant; and
flow the heated amine regenerator bottoms stream to the sulfur recovery plant.

12. The system of claim 11, wherein the first heat exchanger and the second heat exchanger are fluidically coupled to each other in parallel.

13. The system of claim 2, wherein the aromatics complex stream comprises the raffinate overheads column stream in the aromatics complex xylene products separation unit, and wherein, to directly heat the first stream, the heat exchanger system comprises:
the first heat exchanger configured to heat an acid gas regeneration bottom stream using a first branch of the raffinate overheads column stream, and
a second heat exchanger configured to heat a sour water stripper plant bottom stream using a second branch of the raffinate overheads column stream,
wherein the flow control system is configured to:
flow the heated acid gas regenerator bottom cold stream to the amine regeneration plant, and
flow the heated sour water stripper plant bottom stream to the sour water stripper plant.

14. The system of claim 13, wherein the first heat exchanger and the second heat exchanger are fluidically coupled to each other in parallel.

15. The system of claim 2, wherein the aromatics complex stream comprises the raffinate overheads column stream in the aromatics complex xylene products separation unit, and wherein, to directly heat the first stream, the heat exchanger system comprises:
the first heat exchanger configured to heat an acid gas regenerator bottom stream in the amine regeneration plant using a first branch of the raffinate overheads column stream,
a second heat exchanger configured to heat a sour water stripper plant bottom stream in the sour water stripper plant using a second branch of the raffinate overheads column stream, and
a third heat exchanger configured to heat an amine regenerator bottoms stream in the sulfur recovery plant using an extract column overhead stream in the aromatics complex,
wherein the flow control system is configured to:
flow the heated acid gas regenerator bottom cold stream to the amine regeneration plant,
flow the heated sour water stripper plant bottom stream to the sour water stripper plant, and
flow the heated amine regenerator bottoms stream to the sulfur recovery plant.

16. The system of claim 15, wherein the first heat exchanger and the second heat exchanger are fluidically coupled to each other in parallel.

17. The system of claim 1, further comprising a buffer fluid, wherein the heat exchanger system is configured to heat the first stream from the first oil refining plant indirectly through the buffer fluid using the aromatics complex stream.

18. The system of claim 17, wherein the buffer fluid comprises at least one of oil or water.

19. The system of claim 17, wherein, to indirectly heat the first stream from the first oil refining plant through the buffer fluid, the heat exchanger system comprises:
the first heat exchanger configured to heat the buffer fluid using a raffinate overheads column stream in the aromatics complex xylene products separation unit,
wherein the flow control system is configured to flow the heated buffer fluid exiting the first heat exchanger to the sulfur recovery plant, wherein the heat exchanger system comprises a second heat exchanger configured to heat an amine regenerator bottoms stream using the first branch of the heated buffer fluid, wherein the flow control system is configured to:
split the buffer fluid exiting the second heat exchanger into a first branch and a second branch, and
flow the first branch of the heated buffer fluid to the gas separation plant, wherein the heat exchanger system comprises a third heat exchanger configured to heat a de-ethanizer bottoms stream in the gas separation plant stream using the second branch of the heated buffer fluid, wherein the flow control system is configured to flow the second branch of the heated buffer fluid to the gas separation plant, and wherein the heat exchanger system comprises a fourth heat exchanger configured to heat a C3/C4 splitter bottoms stream in the benzene extraction unit using the third branch of the heated buffer fluid.

20. The system of claim 19, wherein the flow control system is configured to:
flow the second branch and the third branch in parallel to the gas separation plant;
combine the second branch and the third branch exiting the third heat exchanger and the fourth heat exchanger, respectively, resulting in a combined buffer fluid stream; and
flow the combined buffer fluid stream to a buffer fluid tank.

21. The system of claim 20, wherein the first heat exchanger and the second heat exchanger are coupled to each other in series, wherein the third heat exchanger is fluidically coupled to the second heat exchanger in series, wherein the fourth heat exchanger is fluidically coupled to the second heat exchanger in series.

22. The system of claim 17, wherein to indirectly heat the first stream from the first oil refining plant through the buffer fluid, the heat exchanger system comprises:
the first heat exchanger configured to heat a first branch of the buffer fluid using a low temperature shift (LTS) converter stream in the hydrogen plant,
a second heat exchanger configured to heat a second branch of the buffer fluid using a diesel hydro-treating stripper overhead stream in the diesel hydro-treating plant, and
a third heat exchanger configured to heat a third branch of the buffer fluid using a diesel hydro-treating stripper bottom product stream in the diesel hydro-treating plant, wherein the flow control system is configured to:
combine the heated first branch, the heated second branch and the heated third branch resulting in heated buffer fluid, and
flow the combined heated first branch, heated second branch and heated third branch to the sour water stripper plant, wherein the heat exchanger system comprises a fourth heat exchanger configured to heat a sour water stripper bottom stream using the combined heated first branch, heated second branch and heated third branch, wherein the flow control system is configured to flow the combined heated first branch, heated second branch and heated third branch exiting the fourth heat exchanger to a benzene extraction unit, and wherein the heat exchanger system comprises a fifth heat exchanger configured to heat a raffinate column stream in the benzene extraction unit using the combined heated first branch, heated second branch and heated third branch received from the fourth heat exchanger.

23. The system of claim 22, further comprising flowing the heated buffer fluid exiting the fifth heat exchanger to a buffer fluid tank.

24. The system of claim 22, wherein the first heat exchanger, the second heat exchanger and the third heat exchanger are fluidically coupled to each other in parallel, wherein the fourth heat exchanger is fluidically coupled in parallel with a combination of the first heat exchanger, the second heat exchanger and the third heat exchanger, wherein the fifth heat exchanger is fluidically coupled to the fourth heat exchanger in series.

25. The system of claim 17, wherein to indirectly heat the first stream from the first oil refining plant through the buffer fluid, the heat exchanger system comprises the first heat exchanger configured to heat the buffer fluid using a raffinate overheads column stream in the aromatics complex xylene products separation unit, wherein the flow control system is configured to flow the heated buffer fluid exiting the first heat exchanger to the sour water stripper plant, wherein the heat exchanger system comprises a second heat exchanger configured to heat a sour water stripper bottom cold stream in the sour water stripper plant using the first branch of the heated buffer fluid received from the first heat exchanger, wherein the flow control system is configured to:
split the heated buffer fluid received from the second heat exchanger into a first branch and a second branch, and
flow the first branch to the gas separation plant, wherein the heat exchanger system comprises a third heat exchanger configured to heat a de-ethanizer bottoms stream in the gas separation plant using the first branch, wherein the flow control system is configured to flow the second branch to the gas separation plant, and wherein the heat exchanger system comprises a fourth heat exchanger configured to heat a C3/C4 splitter bottoms stream in the benzene extraction unit using the second branch.

26. The system of claim 25, wherein the flow control system is configured to:
combine the first branch and the second branch exiting the third heat exchanger and the fourth heat exchanger, respectively, resulting in a combined buffer fluid stream; and
flow the combined buffer fluid stream to a buffer fluid tank.

27. The system of claim 25, wherein the first heat exchanger and the second heat exchanger are fluidically coupled to each other in series, wherein the second heat exchanger and the third heat exchanger are fluidically coupled to each other in series, wherein the third heat exchanger and the fourth heat exchanger are coupled to each other in parallel, wherein the second heat exchanger is fluidically coupled to a combination of the third heat exchanger and the fourth heat exchanger in series.

28. The system of claim 17, wherein, to indirectly heat the first stream from the first oil refining plant through the buffer fluid, the heat exchanger system comprises the first heat exchanger configured to heat the buffer fluid using a raffinate overheads column stream in the aromatics complex xylene products separation unit, wherein the flow control system is configured to:
  split the heated buffer fluid exiting the first heat exchanger into a first branch and a second branch, and
  flow the first branch to the sulfur recovery plant,
wherein the heat exchanger system comprises a second heat exchanger configured to heat an amine regenerator bottoms stream in the sulfur recovery plant using the first branch,
wherein the flow control system is configured to flow the second branch to the sour water stripper plant, and
wherein the heat exchanger system comprises a third heat exchanger configured to heat a sour water stripper bottom stream in the sulfur recovery plant using the second branch.

29. The system of claim 28, wherein the flow control system is configured to:
  flow the first branch and the second branch in parallel to the sour water stripper plant;
  combine the first branch and the second branch exiting the second heat exchanger and the third heat exchanger, respectively, resulting in a combined buffer fluid stream; and
  flow the combined buffer fluid stream to a buffer fluid tank.

30. The system of claim 28, wherein the second heat exchanger and the third heat exchanger are fluidically coupled to each other in parallel, and wherein the first heat exchanger and a combination of the second heat exchanger and the third heat exchanger are fluidically coupled to each other in series.

31. The system of claim 17, wherein, to indirectly heat the first stream from the first oil refining plant through the buffer fluid, the heat exchanger system comprises the first heat exchanger configured to heat the buffer fluid using a raffinate overheads column stream in the aromatics complex xylene products separation unit,
  wherein the flow control system is configured to flow the heated buffer fluid exiting the first heat exchanger to the sulfur recovery plant,
  wherein the heat exchanger system comprises a second heat exchanger configured to heat an amine regenerator bottoms stream in the sulfur recovery plant using the heated buffer fluid received from the first heat exchanger,
  wherein the flow control system is configured to flow the heated buffer fluid exiting the second heat exchanger to the amine regeneration plant,
  wherein the heat exchanger system comprises a third heat exchanger configured to heat an acid gas regenerator bottom stream in the amine regeneration plant using the heated buffer fluid received from the second heat exchanger.

32. The system of claim 31, wherein the first heat exchanger, the second heat exchanger and the third heat exchanger are coupled to each other in series, and wherein the flow control system is configured to flow the buffer fluid stream exiting the third heat exchanger to a buffer fluid tank.

33. The system of claim 17, wherein, to indirectly heat the first stream from the first oil refining plant through the buffer fluid, the heat exchanger system comprises the first heat exchanger configured to heat the buffer fluid using a raffinate overheads column stream in the aromatics complex xylene products separation unit,
  wherein the flow control system is configured to flow the heated buffer fluid exiting the first heat exchanger to the sour water stripper plant,
  wherein the heat exchanger system comprises a second heat exchanger configured to heat a sour water stripper plant bottom stream in the sour water stripper plant using the heated buffer fluid received from the first heat exchanger,
  wherein the flow control system is configured to flow the heated buffer fluid exiting the second heat exchanger to the amine regeneration plant, and
  wherein the heat exchanger system comprises a third heat exchanger configured to heat an acid gas regenerator bottom cold stream in the amine regeneration plant using the second branch of the heated buffer fluid received from the second heat exchanger.

34. The system of claim 33, wherein the first heat exchanger, the second heat exchanger and the third heat exchanger are coupled to each other in series, and wherein the flow control system is configured to flow the buffer fluid stream exiting the third heat exchanger to a buffer fluid tank.

35. The system of claim 17, wherein, to indirectly heat the stream from the first oil refining plant through the buffer fluid, the heat exchanger system comprises:
  the first heat exchanger configured to heat a first branch of the buffer fluid using a raffinate overheads column stream in the aromatics complex xylene products separation unit, and
  a fourth heat exchanger configured to heat a second branch of the buffer fluid using an extract column overhead stream in the aromatics complex,
  wherein the flow control system is configured to flow the first branch of the heated buffer fluid exiting the first heat exchanger to the sour water stripper plant,
  wherein the heat exchanger system comprises a second heat exchanger configured to heat a sour water stripper bottom stream in the sour water stripper plant using the first branch of the heated buffer fluid received from the first heat exchanger,
  wherein the flow control system is configured to flow the heated buffer fluid exiting the second heat exchanger to the amine regeneration plant,
  wherein the heat exchanger system comprises a third heat exchanger configured to heat an acid gas regenerator section stripper bottom stream using the heated buffer fluid received from the second heat exchanger,
  wherein the flow control system is configured to flow the second branch of the heated buffer fluid exiting the fourth heat exchanger to the sulfur recovery plant, and
  wherein the heat exchanger system comprises a fifth heat exchanger configured to heat an amine regenerator bottoms stream in the sulfur recovery plant using the second branch of the heated buffer fluid received from the fourth heat exchanger.

36. The system of claim 35, wherein the flow control system is configured to:
  combine the first branch exiting the third heat exchanger and the second branch exiting the fifth heat exchanger resulting in a combined buffer fluid stream; and
  flow the combined buffer fluid stream to a buffer fluid tank.

37. The system of claim 35, wherein the first heat exchanger and the fourth heat exchanger are fluidically coupled to each other in parallel, wherein the first heat exchanger and the second heat exchanger are fluidically coupled to each other in series, wherein the second heat exchanger and the third heat exchanger are fluidically coupled to each other in series, wherein the fifth heat exchanger and the fourth heat exchanger are fluidically coupled to each other in series.

* * * * *